US012806384B2

(12) United States Patent
Beeby et al.

(10) Patent No.: US 12,806,384 B2
(45) Date of Patent: Nov. 24, 2026

(54) DEVICES, SYSTEMS, AND METHODS FOR BLOOD FLOW CONTROL

(71) Applicants: Certus Critical Care, Inc., Salt Lake City, UT (US); Wake Forest University Health Sciences, Winston-Salem, NC (US)

(72) Inventors: Ruth Beeby, Santa Clara, CA (US); Cheng-wei Pei, Belmont, CA (US); Myra Fabro, San Francisco, CA (US); David Poisner, Carmichael, CA (US); Patrick Ryan Kolbay, Salt Lake City, UT (US); Daniel Fong, Sacramento, CA (US); Melanie McWade, Portland, OR (US); Timothy Williams, Winston-Salem, NC (US); Lucas Neff, Winston-Salem, NC (US); Michael Austin Johnson, Holladay, UT (US)

(73) Assignees: Certus Critical Care, Inc., Salt Lake City, UT (US); Wake Forest University Health Sciences, Winston-Salem, NC (US)

( * ) Notice: Subject to any disclaimer, the term of this patent is extended or adjusted under 35 U.S.C. 154(b) by 746 days.

(21) Appl. No.: 17/842,755

(22) Filed: Jun. 16, 2022

(65) Prior Publication Data

US 2022/0401709 A1 Dec. 22, 2022

Related U.S. Application Data

(60) Provisional application No. 63/244,689, filed on Sep. 15, 2021, provisional application No. 63/211,554, filed on Jun. 16, 2021.

(51) Int. Cl.
*A61M 25/10* (2013.01)
*A61B 17/12* (2006.01)

(52) U.S. Cl.
CPC ... *A61M 25/10182* (2013.11); *A61B 17/1204* (2013.01); *A61B 17/12109* (2013.01);
(Continued)

(58) Field of Classification Search
CPC ...... A61M 25/10182; A61M 25/10188; A61M 2205/0238; A61M 2205/3306;
(Continued)

(56) References Cited

U.S. PATENT DOCUMENTS 2,156,289 A 5/1939 Hoy
3,467,101 A 9/1969 Fogarty et al.
(Continued)

FOREIGN PATENT DOCUMENTS

AU 2015201978 A1 5/2015
AU 2015274743 B2 11/2016
(Continued)

OTHER PUBLICATIONS

International Search Report and Written Opinion for International Application No. PCT/US2022/049335 dated Mar. 15, 2023, 15 pages.
(Continued)

*Primary Examiner* — Kathleen S Holwerda
*Assistant Examiner* — Cherie M Poland
(74) *Attorney, Agent, or Firm* — COOLEY LLP

(57) ABSTRACT

Systems and methods for performing endovascular procedures are described herein. The systems may include various blood flow control devices, control systems, and/or fluid delivery devices. The methods may comprise advancing an expandable member of a blood flow control device to a target location in a blood vessel of a patient, and rotating a circular gear positioned at least partially within a housing of a controller via the controller communicably coupled to the blood flow control device. Rotating the circular gear may
(Continued)

translate a linear gear of a syringe pump fluidly coupled to the expandable member thereby adjusting a volume of the expandable member.

23 Claims, 43 Drawing Sheets

(52) U.S. Cl.
CPC . *A61B 17/12136* (2013.01); *A61M 25/10188* (2013.11); *A61M 2205/0238* (2013.01); *A61M 2205/3306* (2013.01); *A61M 2205/3327* (2013.01); *A61M 2205/502* (2013.01)

(58) Field of Classification Search
CPC .... A61M 2205/3327; A61M 2205/502; A61B 17/1204; A61B 17/12109; A61B 17/12136
See application file for complete search history.

(56) References Cited

U.S. PATENT DOCUMENTS

| | | | |
|---|---|---|---|
| 3,791,374 | A | 2/1974 | Guarino |
| 4,396,385 | A | 8/1983 | Kelly et al. |
| 4,464,172 | A | 8/1984 | Lichtenstein |
| 4,691,708 | A | 9/1987 | Kane |
| 4,713,888 | A | 12/1987 | Broselow |
| 4,777,951 | A | 10/1988 | Cribier et al. |
| 4,823,469 | A | 4/1989 | Broselow |
| 4,846,174 | A | 7/1989 | Willard et al. |
| 4,865,549 | A | 9/1989 | Sonsteby |
| 4,926,885 | A | 5/1990 | Hinkle |
| 4,983,166 | A | 1/1991 | Yamawaki |
| 5,047,045 | A | 9/1991 | Arney et al. |
| 5,087,246 | A | 2/1992 | Smith |
| 5,135,494 | A | 8/1992 | Engelson et al. |
| 5,152,776 | A | 10/1992 | Pinchuk |
| 5,158,529 | A | 10/1992 | Kanai |
| 5,169,386 | A | 12/1992 | Becker et al. |
| 5,217,456 | A | 6/1993 | Narciso, Jr. |
| 5,282,479 | A | 2/1994 | Havran |
| 5,320,605 | A | 6/1994 | Sahota |
| 5,344,398 | A | 9/1994 | Hara |
| 5,383,856 | A | 1/1995 | Bersin |
| 5,447,503 | A | 9/1995 | Miller |
| 5,486,192 | A | 1/1996 | Walinsky et al. |
| 5,505,702 | A | 4/1996 | Arney |
| 5,522,400 | A | 6/1996 | Williams |
| 5,558,644 | A | 9/1996 | Boyd et al. |
| 5,571,093 | A | 11/1996 | Cruz et al. |
| 5,607,394 | A | 3/1997 | Andersen et al. |
| 5,678,570 | A | 10/1997 | Manning |
| 5,718,678 | A | 2/1998 | Fleming, III |
| 5,738,652 | A | 4/1998 | Boyd et al. |
| 5,779,731 | A | 7/1998 | Leavitt |
| 5,911,702 | A | 6/1999 | Romley et al. |
| 5,925,018 | A | 7/1999 | Ungerstedt |
| 6,011,988 | A | 1/2000 | Lynch et al. |
| 6,013,019 | A | 1/2000 | Fischell et al. |
| 6,042,532 | A | 3/2000 | Freed et al. |
| 6,102,930 | A | 8/2000 | Simmons, Jr. |
| 6,113,579 | A | 9/2000 | Eidenschink et al. |
| 6,146,370 | A | 11/2000 | Barbut |
| 6,161,547 | A | 12/2000 | Barbut |
| 6,165,199 | A | 12/2000 | Barbut |
| 6,190,304 | B1 | 2/2001 | Downey et al. |
| 6,190,356 | B1 | 2/2001 | Bersin |
| 6,231,551 | B1 | 5/2001 | Barbut |
| 6,231,572 | B1 | 5/2001 | Hart et al. |
| 6,248,083 | B1 | 6/2001 | Smith et al. |
| 6,248,121 | B1 | 6/2001 | Nobles |
| 6,254,569 | B1 | 7/2001 | O'Donnell et al. |
| 6,280,434 | B1 | 8/2001 | Kinoshita et al. |
| 6,315,768 | B1 | 11/2001 | Wallace |
| 6,394,977 | B1 | 5/2002 | Taylor et al. |
| 6,423,031 | B1 | 7/2002 | Donlon |
| 6,453,572 | B2 | 9/2002 | Cross et al. |
| 6,565,552 | B1 | 5/2003 | Barbut |
| 6,575,932 | B1 | 6/2003 | O'Brien et al. |
| 6,579,221 | B1 | 6/2003 | Peterson |
| 6,592,557 | B2 | 7/2003 | Barbut |
| 6,602,270 | B2 | 8/2003 | Leschinsky et al. |
| 6,620,128 | B1 | 9/2003 | Simhambhatla |
| 6,635,046 | B1 | 10/2003 | Barbut |
| 6,656,153 | B1 | 12/2003 | Sakai et al. |
| 6,666,814 | B2 | 12/2003 | Downey et al. |
| 6,669,679 | B1 | 12/2003 | Savage et al. |
| 6,679,860 | B2 | 1/2004 | Stiger |
| 6,695,811 | B2 | 2/2004 | Samson et al. |
| 6,712,806 | B2 | 3/2004 | St. Germain et al. |
| 6,719,270 | B2 | 4/2004 | Ozawa |
| 6,719,720 | B1 | 4/2004 | Voelker et al. |
| 6,733,513 | B2 | 5/2004 | Boyle et al. |
| 6,735,532 | B2 | 5/2004 | Freed et al. |
| 6,736,790 | B2 | 5/2004 | Barbut et al. |
| 6,743,196 | B2 | 6/2004 | Barbut et al. |
| 6,746,462 | B1 | 6/2004 | Selmon et al. |
| 6,767,345 | B2 | 7/2004 | St. Germain et al. |
| 6,796,959 | B2 | 9/2004 | Davis et al. |
| 6,796,992 | B2 | 9/2004 | Barbut |
| 6,848,448 | B1 | 2/2005 | St. Germain et al. |
| 6,868,739 | B1 | 3/2005 | Krivitski et al. |
| 6,936,056 | B2 | 8/2005 | Nash et al. |
| 6,979,318 | B1 | 12/2005 | McDonald et al. |
| 7,166,097 | B2 | 1/2007 | Barbut |
| 7,229,403 | B2 | 6/2007 | Schock et al. |
| 7,341,571 | B1 | 3/2008 | Harris et al. |
| 7,434,326 | B2 | 10/2008 | Gifford |
| 7,468,027 | B2 | 12/2008 | Barbut et al. |
| 7,503,904 | B2 | 3/2009 | Choi |
| 7,503,909 | B2 | 3/2009 | Kusu et al. |
| 7,763,043 | B2 | 7/2010 | Goodin et al. |
| 7,867,195 | B2 | 1/2011 | Barbut et al. |
| 7,888,740 | B2 | 2/2011 | Tsutsumi et al. |
| 7,892,469 | B2 | 2/2011 | Lim et al. |
| 7,909,810 | B2 | 3/2011 | Noone |
| 7,927,346 | B2 | 4/2011 | Vancamp et al. |
| 7,951,186 | B2 | 5/2011 | Eidenschink et al. |
| 7,951,819 | B2 | 5/2011 | Niculescu-Duvaz et al. |
| 7,959,644 | B2 | 6/2011 | Shriver |
| 7,993,324 | B2 | 8/2011 | Barbut |
| 8,088,103 | B2 | 1/2012 | Teeslink et al. |
| 8,088,121 | B2 | 1/2012 | Nishide et al. |
| 8,162,879 | B2 | 4/2012 | Hattangadi et al. |
| 8,241,241 | B2 | 8/2012 | Evans et al. |
| 8,262,611 | B2 | 9/2012 | Teeslink et al. |
| 8,419,648 | B2 | 4/2013 | Corl et al. |
| 8,430,899 | B2 | 4/2013 | Dae et al. |
| 8,499,681 | B2 | 8/2013 | Kanner et al. |
| 8,545,382 | B2 | 10/2013 | Suzuki et al. |
| 8,628,461 | B2 | 1/2014 | Mohl |
| 8,655,798 | B2 | 2/2014 | Humphrey et al. |
| 8,672,868 | B2 | 3/2014 | Simons |
| 8,672,930 | B2 | 3/2014 | Wittenberger |
| 8,747,358 | B2 | 6/2014 | Trombley, III et al. |
| 8,790,297 | B2 | 7/2014 | Bromander et al. |
| 8,814,900 | B2 | 8/2014 | Fleming, III |
| 8,888,740 | B2 | 11/2014 | Barbut et al. |
| 8,900,214 | B2 | 12/2014 | Nance et al. |
| 8,948,848 | B2 | 2/2015 | Merhi |
| 8,951,565 | B2 | 2/2015 | McCarthy |
| 8,961,426 | B2 | 2/2015 | Martin et al. |
| 9,108,000 | B2 | 8/2015 | Kassab |
| 9,131,874 | B2 | 9/2015 | Eliason et al. |
| D748,257 | S | 1/2016 | Franklin |
| 9,393,384 | B1 | 7/2016 | Kapur et al. |
| 9,402,952 | B2 | 8/2016 | Beyersdorf |
| 9,414,843 | B2 | 8/2016 | Pavcnik et al. |
| 9,474,882 | B2 | 10/2016 | Franklin |
| 9,492,084 | B2 | 11/2016 | Behar et al. |
| 9,682,217 | B2 | 6/2017 | Franklin et al. |
| 9,687,333 | B2 | 6/2017 | Angel et al. |
| 10,004,622 | B2 | 6/2018 | Sanati et al. |

(56) References Cited

U.S. PATENT DOCUMENTS 10,111,669 B2 10/2018 Eliason et al.
10,143,789 B2 12/2018 Frost
10,149,962 B2 12/2018 Franklin et al.
10,188,345 B2 1/2019 Venkatraman et al.
10,232,142 B2 3/2019 Franklin
10,279,094 B2 5/2019 Williams et al.
10,279,152 B2 5/2019 Kapur et al.
10,335,152 B2 7/2019 Barbut et al.
10,368,872 B2 8/2019 Franklin et al.
10,569,062 B2 2/2020 Franklin
10,758,715 B2 9/2020 Kapur et al.
10,765,841 B2 9/2020 Zhadkevich
10,806,903 B2 10/2020 Franklin et al.
10,842,975 B2 11/2020 Kapur et al.
10,881,770 B2 1/2021 Tuval et al.
10,885,813 B2 1/2021 Krummenacher et al.
11,013,515 B2 5/2021 Zhadkevich
11,058,864 B2 7/2021 Frost
11,135,408 B2 10/2021 Schwartz et al.
11,154,690 B2 10/2021 Avneri et al.
11,253,264 B2 2/2022 Franklin et al.
11,311,365 B2 4/2022 Zhadkevich
11,464,703 B2 10/2022 Johnson et al.
11,596,411 B2 3/2023 Johnson et al.
11,602,592 B2 3/2023 Johnson et al.
11,633,192 B2 4/2023 Johnson et al.
11,672,951 B2 6/2023 Franklin et al.
11,857,737 B2 1/2024 Franklin et al.
12,251,111 B2 3/2025 Johnson
12,290,659 B2 5/2025 Johnson et al.
12,318,090 B2 6/2025 Johnson et al.
12,419,644 B2 9/2025 Johnson et al.
2002/0007146 A1 1/2002 Omaleki et al.
2002/0045854 A1 4/2002 Royo et al.
2002/0062119 A1 5/2002 Zadno-Azizi
2002/0072647 A1 6/2002 Schock et al.
2002/0115982 A1 8/2002 Barbut et al.
2002/0193735 A1 12/2002 Stiger
2003/0023200 A1 1/2003 Barbut et al.
2003/0032974 A1 2/2003 Leschinsky et al.
2003/0167038 A1 9/2003 Yozu et al.
2003/0226568 A1 12/2003 McKinley et al.
2004/0073162 A1 4/2004 Bleam et al.
2004/0082935 A1 4/2004 Lee et al.
2004/0097813 A1 5/2004 Williams
2004/0111006 A1 6/2004 Alferness et al.
2004/0111016 A1 6/2004 Casscells et al.
2004/0254483 A1 12/2004 Zdeblick et al.
2004/0254528 A1 12/2004 Adams et al.
2005/0015048 A1 1/2005 Chiu et al.
2005/0059931 A1 3/2005 Garrison et al.
2005/0148812 A1 7/2005 Nigroni et al.
2005/0234293 A1 10/2005 Yamamoto et al.
2005/0261725 A1 11/2005 Crawford et al.
2006/0064059 A1 3/2006 Gelfand et al.
2006/0100639 A1 5/2006 Levin et al.
2006/0217670 A1 9/2006 Cecchi et al.
2006/0287569 A1 12/2006 Schock et al.
2007/0043307 A1 2/2007 Raulerson et al.
2007/0043409 A1 2/2007 Brian, III et al.
2007/0106258 A1 5/2007 Chiu et al.
2007/0118095 A1 5/2007 Barbut
2007/0129466 A1 6/2007 Kagawa et al.
2007/0135830 A1 6/2007 Schaeffer
2007/0208291 A1 9/2007 Patel
2007/0219441 A1 9/2007 Carlin et al.
2007/0219466 A1 9/2007 Tremulis et al.
2007/0219488 A1 9/2007 Francescatti
2007/0270935 A1 11/2007 Newhauser et al.
2008/0027356 A1 1/2008 Chen et al.
2008/0051764 A1 2/2008 Dent et al.
2008/0082046 A1 4/2008 Kato et al.
2008/0082119 A1 4/2008 Vitullo
2008/0097300 A1 4/2008 Eskaros et al.
2008/0178882 A1 7/2008 Christopher et al.
2008/0188803 A1 8/2008 Jang
2008/0243067 A1 10/2008 Rottenberg et al.
2008/0243221 A1 10/2008 Arcand
2008/0262477 A1 10/2008 Djaladat
2009/0012467 A1 1/2009 Suzuki et al.
2009/0026595 A1 1/2009 Kadoi
2009/0062666 A1 3/2009 Roteliuk
2009/0156978 A1 6/2009 Faul et al.
2009/0171222 A1 7/2009 Valdes
2009/0171272 A1 7/2009 Tegg et al.
2009/0171293 A1 7/2009 Yang et al.
2009/0265951 A1 10/2009 Black
2009/0287079 A1 11/2009 Shriver
2009/0312807 A1 12/2009 Boudreault et al.
2010/0016735 A1 1/2010 Harpas et al.
2010/0041984 A1 2/2010 Shapland et al.
2010/0113939 A1 5/2010 Mashimo et al.
2010/0234915 A1 9/2010 Herlich et al.
2010/0262076 A1 10/2010 Rowe et al.
2010/0268017 A1 10/2010 Siess
2010/0280451 A1 11/2010 Teeslink et al.
2010/0292635 A1 11/2010 Sundar
2010/0312126 A1 12/2010 Williams et al.
2010/0318114 A1 12/2010 Pranevicius et al.
2011/0034768 A1 2/2011 Ozaki et al.
2011/0112442 A1 5/2011 Meger et al.
2011/0144742 A1 6/2011 Madrid et al.
2011/0196412 A1 8/2011 Levit et al.
2011/0230821 A1 9/2011 Babic
2011/0295177 A1 12/2011 Mohl
2011/0295301 A1 12/2011 Hoem et al.
2011/0295302 A1 12/2011 Mohl
2011/0301630 A1 12/2011 Hendriksen et al.
2012/0101413 A1 4/2012 Beetel et al.
2012/0108979 A1 5/2012 Franklin et al.
2012/0109057 A1 5/2012 Krolik et al.
2012/0116352 A1 5/2012 Rangi
2012/0130359 A1 5/2012 Turovskiy
2012/0172911 A1 7/2012 Welch
2012/0185267 A1* 7/2012 Kamen ................ A61B 5/0024
705/2
2012/0209176 A1 8/2012 Anderson
2012/0215166 A1 8/2012 Barki
2012/0220884 A1 8/2012 Yamashita et al.
2012/0271231 A1 10/2012 Agrawal
2012/0302994 A1 11/2012 Wilson et al.
2013/0060316 A1 3/2013 Sanati et al.
2013/0102926 A1 4/2013 Eliason et al.
2013/0102929 A1 4/2013 Haight et al.
2013/0172786 A1 7/2013 Olson et al.
2013/0178750 A1 7/2013 Sheehan et al.
2013/0190619 A1 7/2013 Nudel
2013/0190633 A1 7/2013 Dorando et al.
2013/0281787 A1 10/2013 Avneri et al.
2013/0281869 A1 10/2013 Barbut et al.
2013/0289607 A1 10/2013 Pedersen et al.
2013/0338637 A1 12/2013 Fischer, Jr. et al.
2014/0107410 A1 4/2014 Rosenberg
2014/0221898 A1 8/2014 Kurrus et al.
2014/0243873 A1 8/2014 Franklin
2014/0249504 A1 9/2014 Franklin et al.
2014/0249573 A1 9/2014 Arav
2014/0276042 A1 9/2014 Smith et al.
2014/0316012 A1 10/2014 Freyman et al.
2014/0323846 A1 10/2014 Niebel et al.
2014/0350523 A1 11/2014 Dehdashtian et al.
2014/0364835 A1 12/2014 Allen et al.
2014/0378869 A1 12/2014 Sela et al.
2015/0011900 A1 1/2015 Lu et al.
2015/0012031 A1 1/2015 Rago et al.
2015/0039012 A1 2/2015 Solar et al.
2015/0133892 A1 5/2015 Joe et al.
2015/0157326 A1 6/2015 Schiemanck et al.
2015/0165174 A1 6/2015 Helkowski et al.
2015/0245867 A1 9/2015 Gross
2015/0272732 A1 10/2015 Tilson et al.
2015/0290372 A1 10/2015 Muller et al.
2015/0327836 A1 11/2015 Stone et al.
2015/0367098 A1 12/2015 Aggerholm et al.

(56) References Cited

U.S. PATENT DOCUMENTS

| | | | |
|---|---|---|---|
| 2016/0000446 | A1 | 1/2016 | Eliason et al. |
| 2016/0029995 | A1 | 2/2016 | Navratil et al. |
| 2016/0166197 | A1 | 6/2016 | Venkatraman et al. |
| 2016/0206798 | A1 | 7/2016 | Williams et al. |
| 2016/0213893 | A1 | 7/2016 | Franklin |
| 2016/0262647 | A1 | 9/2016 | Berenfeld |
| 2016/0310103 | A1 | 10/2016 | Liu et al. |
| 2016/0375230 | A1 | 12/2016 | Lee et al. |
| 2017/0043123 | A1 | 2/2017 | Franklin |
| 2017/0049946 | A1 | 2/2017 | Kapur et al. |
| 2017/0100142 | A1 | 4/2017 | Look et al. |
| 2017/0106140 | A1 | 4/2017 | Teutsch et al. |
| 2017/0164876 | A1 | 6/2017 | Hyde et al. |
| 2017/0245794 | A1 | 8/2017 | Sharma et al. |
| 2017/0266379 | A1 | 9/2017 | Harrity |
| 2017/0348049 | A1 | 12/2017 | Vrba et al. |
| 2017/0368313 | A1 | 12/2017 | Franklin et al. |
| 2018/0064350 | A1 | 3/2018 | Thakur et al. |
| 2018/0146872 | A1 | 5/2018 | Shaknovich |
| 2018/0147375 | A1 | 5/2018 | Johnson et al. |
| 2018/0154129 | A1 | 6/2018 | Paul et al. |
| 2018/0193650 | A1 | 7/2018 | Srivastava et al. |
| 2018/0228951 | A1 | 8/2018 | Schwammenthal et al. |
| 2018/0236203 | A1 | 8/2018 | Franklin et al. |
| 2018/0243541 | A1 | 8/2018 | Kapur et al. |
| 2019/0015630 | A1 | 1/2019 | Franklin et al. |
| 2019/0046762 | A1 | 2/2019 | Rogers et al. |
| 2019/0046769 | A1 | 2/2019 | Avneri et al. |
| 2019/0076152 | A1 | 3/2019 | Franklin et al. |
| 2019/0126014 | A1 | 5/2019 | Kapur et al. |
| 2019/0290845 | A1* | 9/2019 | List ..................... A61M 5/3146 |
| 2019/0307462 | A1 | 10/2019 | Franklin et al. |
| 2019/0320911 | A1 | 10/2019 | Suh et al. |
| 2019/0336665 | A1 | 11/2019 | Frost |
| 2019/0378436 | A1 | 12/2019 | Krummenacher et al. |
| 2020/0016331 | A1 | 1/2020 | Lee et al. |
| 2020/0038566 | A1 | 2/2020 | Johnson et al. |
| 2020/0046364 | A1 | 2/2020 | Johnson et al. |
| 2020/0054520 | A1 | 2/2020 | Johnson et al. |
| 2020/0163707 | A1* | 5/2020 | Sliwa ..................... A61B 18/02 |
| 2020/0238018 | A1* | 7/2020 | Lee ................... A61M 5/31568 |
| 2020/0276419 | A1 | 9/2020 | Franklin et al. |
| 2020/0329995 | A1 | 10/2020 | Stone et al. |
| 2020/0375603 | A1 | 12/2020 | Parekh et al. |
| 2021/0030423 | A1 | 2/2021 | Starnes |
| 2021/0038229 | A1 | 2/2021 | Radl et al. |
| 2021/0045864 | A1 | 2/2021 | Pelssers et al. |
| 2021/0212697 | A1 | 7/2021 | Frost et al. |
| 2021/0236136 | A1 | 8/2021 | Mohl et al. |
| 2021/0275783 | A1 | 9/2021 | Johnson et al. |
| 2021/0290243 | A1 | 9/2021 | Franklin et al. |
| 2021/0322026 | A1 | 10/2021 | Johnson et al. |
| 2021/0330959 | A1 | 10/2021 | Frost |
| 2021/0338245 | A1 | 11/2021 | Johnson et al. |
| 2021/0353298 | A1 | 11/2021 | Williams et al. |
| 2021/0370025 | A1 | 12/2021 | Pickering et al. |
| 2022/0008090 | A1 | 1/2022 | Look et al. |
| 2022/0233264 | A1* | 7/2022 | Klem ..................... A61B 34/35 |
| 2022/0323083 | A1 | 10/2022 | Franklin et al. |
| 2023/0001141 | A1 | 1/2023 | Franklin et al. |
| 2023/0079117 | A1 | 3/2023 | Beeby et al. |
| 2023/0138661 | A1 | 5/2023 | Mohlin et al. |
| 2023/0270444 | A1 | 8/2023 | Fong et al. |
| 2023/0338037 | A1 | 10/2023 | Johnson |
| 2023/0355866 | A1 | 11/2023 | Johnson et al. |
| 2023/0380702 | A1 | 11/2023 | Poisner |
| 2023/0414220 | A1 | 12/2023 | Johnson et al. |
| 2023/0414221 | A1 | 12/2023 | Franklin et al. |
| 2024/0165380 | A1 | 5/2024 | Williams et al. |
| 2025/0235608 | A1 | 7/2025 | Johnson et al. |
| 2025/0249220 | A1 | 8/2025 | Ogawa et al. |
| 2025/0325789 | A1 | 10/2025 | Maslin et al. |
| 2026/0013741 | A1 | 1/2026 | Fabro |
| 2026/0013869 | A1 | 1/2026 | Johnson |

FOREIGN PATENT DOCUMENTS

| | | | | |
|---|---|---|---|---|
| AU | 2014223477 | B2 | 2/2017 | |
| AU | 2014223556 | B2 | 5/2017 | |
| AU | 2016232781 | B2 | 11/2017 | |
| AU | 2017272335 | B2 | 6/2018 | |
| AU | 2014317859 | B2 | 5/2019 | |
| CA | 2941438 | A1 | 12/2015 | |
| CA | 2980018 | A1 | 9/2016 | |
| CA | 2990479 | A1 | 12/2017 | |
| CN | 1216929 | A | 5/1999 | |
| CN | 102740906 | A | 10/2012 | |
| CN | 105339035 | A | 2/2016 | |
| CN | 105792879 | A | 7/2016 | |
| DE | 3424552 | A1 | 1/1986 | |
| EM | 0026882830001 | | 3/2019 | |
| EP | 0188467 | A1 | 7/1986 | |
| EP | 1094861 | B1 | 4/2005 | |
| EP | 1658808 | A1 | 5/2006 | |
| EP | 1911484 | A2 | 4/2008 | |
| EP | 2308541 | A1 | 4/2011 | |
| EP | 2347726 | A2 | 7/2011 | |
| EP | 2389974 | A1 | 11/2011 | |
| EP | 2716323 | A1 | 4/2014 | |
| EP | 2837402 | A2 | 2/2015 | |
| EP | 3148603 | B1 | 1/2018 | |
| EP | 3260158 | B1 | 11/2018 | |
| EP | 3270997 | B1 | 7/2019 | |
| EP | 3560416 | A1 | 10/2019 | |
| EP | 3424552 | B1 | 4/2020 | |
| EP | 2961464 | B1 | 5/2020 | |
| EP | 3549121 | B1 | 9/2021 | |
| FR | 2961464 | A1 | 12/2011 | |
| GB | 902441 | A | 8/1962 | |
| GB | 2297259 | A | 7/1996 | |
| GB | 90026882830001 | | 4/2015 | |
| IL | 240775 | B | 11/2018 | |
| JP | H03198868 | A | 8/1991 | |
| JP | H03280962 | A | 12/1991 | |
| JP | H09164208 | A | 6/1997 | |
| JP | H1080497 | A | 3/1998 | |
| JP | 2000217922 | A | 8/2000 | |
| JP | 2002505165 | A | 2/2002 | |
| JP | 2002505919 | A | 2/2002 | |
| JP | 2003079738 | A | 3/2003 | |
| JP | 2003535652 | A | 12/2003 | |
| JP | 2004533290 | A | 11/2004 | |
| JP | 2007014820 | A | 1/2007 | |
| JP | 2008237529 | A | 10/2008 | |
| JP | 2008546471 | A | 12/2008 | |
| JP | 2010538797 | A | 12/2010 | |
| JP | 2011055942 | A | 3/2011 | |
| JP | 2011245300 | A | 12/2011 | |
| JP | 2013042912 | A | 3/2013 | |
| JP | 2015120088 | A | 7/2015 | |
| JP | 2017516624 | A | 6/2017 | |
| JP | 6286564 | B2 | 2/2018 | |
| JP | 6343009 | B2 | 6/2018 | |
| JP | 6343290 | B2 | 6/2018 | |
| JP | 6345192 | B2 | 6/2018 | |
| JP | 2018523534 | A | 8/2018 | |
| JP | 6408176 | B2 | 10/2018 | |
| JP | 6472536 | B2 | 2/2019 | |
| WO | WO-9220398 | A1 | 11/1992 | |
| WO | WO-9713542 | A1 | 4/1997 | |
| WO | WO-9834670 | A2 | 8/1998 | |
| WO | WO-9924105 | A2 | 5/1999 | |
| WO | WO-9944666 | A2 | 9/1999 | |
| WO | WO-0078386 | A1 * | 12/2000 | ........ A61M 25/1018 |
| WO | WO-0197743 | A2 | 12/2001 | |
| WO | WO-02085443 | A1 | 10/2002 | |
| WO | WO-2004049970 | A2 | 6/2004 | |
| WO | WO-2006014631 | A1 | 2/2006 | |
| WO | WO-2006135853 | A2 | 12/2006 | |
| WO | WO-2007001701 | A1 | 1/2007 | |
| WO | WO-2007022592 | A1 | 3/2007 | |
| WO | WO-2008013441 | A1 | 1/2008 | |
| WO | WO-2009039203 | A2 | 3/2009 | |
| WO | WO-2010030882 | A1 | 3/2010 | |

(56) References Cited

FOREIGN PATENT DOCUMENTS

| | | | | |
|---|---|---|---|---|
| WO | WO-2010070685 A1 | 6/2010 | | |
| WO | WO-2011133736 A2 | 10/2011 | | |
| WO | WO-2013096548 A1 | 6/2013 | | |
| WO | WO-2013096713 A2 | 6/2013 | | |
| WO | WO-2014003809 A1 | 1/2014 | | |
| WO | WO-2014036530 A1 | 3/2014 | | |
| WO | WO-2014134215 A1 | 9/2014 | | |
| WO | WO-2014152191 A1 | 9/2014 | | |
| WO | WO-2014176668 A1 | 11/2014 | | |
| WO | WO-2015006828 A1 | 1/2015 | | |
| WO | WO-2015035393 A1 | 3/2015 | | |
| WO | WO-2015100393 A1 | 7/2015 | | |
| WO | WO-2015181167 A1 | 12/2015 | | |
| WO | WO-2015191685 A1 | 12/2015 | | |
| WO | WO-2016126369 A1 | 8/2016 | | |
| WO | WO-2016145163 A1 | 9/2016 | | |
| WO | WO-2016149653 A2 | 9/2016 | | |
| WO | WO-2016163465 A1 | 10/2016 | | |
| WO | WO-2016149653 A3 | 11/2016 | | |
| WO | WO-2016196837 A1 | 12/2016 | | |
| WO | WO-2017210584 A1 | 12/2017 | | |
| WO | WO-2018021180 A1 | 2/2018 | | |
| WO | WO-2018089837 A1 | 5/2018 | | |
| WO | WO-2018132623 A1 | 7/2018 | | |
| WO | WO-2018195507 A1 | 10/2018 | | |
| WO | WO-2018235655 A1 | 12/2018 | | |
| WO | WO-2019195323 A1 | 10/2019 | | |
| WO | WO-2020033372 A1 | 2/2020 | | |
| WO | WO-2020039083 A2 | 2/2020 | | |
| WO | WO-2020157648 A1 * | 8/2020 | ........ | A61M 25/0026 |
| WO | WO-2021178937 A1 | 9/2021 | | |
| WO | WO-2021188602 A2 | 9/2021 | | |
| WO | WO-2022266397 A2 | 12/2022 | | |
| WO | WO-2023043513 A1 | 3/2023 | | |
| WO | WO-2023086344 A1 | 5/2023 | | |
| WO | WO-2023224679 A2 | 11/2023 | | |
| WO | WO-2023225110 A1 | 11/2023 | | |
| WO | WO-2023230630 A1 | 11/2023 | | |
| WO | WO-2024030319 A1 | 2/2024 | | |
| WO | WO-2024228736 A2 | 11/2024 | | |

OTHER PUBLICATIONS

Invitation to pay additional fees for International Application No. PCT/US2023/011298, dated Jan. 23, 2024, 17 pages.

Tsoukalas et al., "A solid-state pressure-sensing microsystem for biomedical applications" Sensors and Actuators A: Physical (1997) 62(1-3):551-555.

International Search Report and Written Opinion for International Application No. PCT/US2022/033898, mailed on Dec. 16, 2022, 30 pages.

International Search Report and Written Opinion for International Application No. PCT/US2022/033896, mailed on Nov. 28, 2022, 25 pages.

Abid, Mustafa, et al., "Reperfusion repercussions: A review of the metabolic derangements following resuscitative endovascular balloon occlusion of the aorta", Journal of Trauma and Acute Care Surgery (Aug. 2020); 89(2S): S39-S44.

Adelson, P. David, et al., "Guidelines for the acute medical management of severe traumatic brain injury in infants, children, and adolescents. Chapter 1: Introduction", Pediatric Critical Care Medicine (Jul. 2003); 4(3 Suppl): S2-4.

[Author Unknown], "Technology Pipeline". Certus Critical Care Inc. (Retrieved on Jun. 17, 2022); [Online] Retrieved from the Internet, https://www.certuscriticalcare.com/technology-portfolio, 16 pages.

Beyer, Carl A., et al., "Resuscitative endovascular balloon occlusion of the aorta (REBOA) in a swine model of hemorrhagic shock and blunt thoracic injury", European Journal of Trauma and Emergency Surgery (2020); 46(6): 1357-1366. Epub: Oct. 1, 2019.

Beyer, Carl A., et al., "Resuscitative endovascular balloon occlusion of the aorta induced myocardial injury is mitigated by endovascular variable aortic control", Journal of Trauma and Acute Care Surgery (Sep. 2019); 87(3): 590-598.

Bonnici, Maximilian, et al., "Successfully Stifling Retroperitoneal and Pelvic Exsanguination by Resuscitative Endovascular Balloon Occlusion of the Aorta in a Rural Setting", Journal of Endovascular Resuscitation and Trauma Management (2022); 6(2): 110-115.

Borzelli, Antonio, et al., "Successful Endovascular Embolisation of an Unusual Giant Pseudoaneurysm of the Middle Colic Artery", Journal of Endovascular Resuscitation and Trauma Management (2022); 6(2): 84-90.

Borzelli, Antonio, et al., "Successful Endovascular Management of a Massive Hemoptysis due to a Rare Oncological Giant Pulmonary Artery Pseudoaneurysm", Journal of Endovascular Resuscitation and Trauma Management (2022); 6(2): 91-96.

Certus Critical Care Presentation, "Beyond REBOA: An experimental model of Endovascular Variable Aortic Control (EVAC) using an automated extracorporeal circuit", Society for Military Surgeons' Boston (Mar. 2, 2016), 21 pages.

Certus Critical Care Presentation, "New Endovascular Techniques for Trauma: NextGenREBOA", Vienna Endovascular Trauma Meeting (Feb. 2016), 46 pages.

Chieregato, Arturo, et al., "Cerebral Blood Flow in Traumatic Contusions Is Predominantly Reduced after an Induced Acute Elevation of Cerebral Perfusion Pressure", Neurosurgery (2007); 60(1): 115-123.

Curtis, Eleanor E., et al., "Resuscitative endovascular balloon occlusion of the aorta during non-ST elevation myocardial infarction: A case report", Trauma (2019); 21(2): 147-151.

Davidson, Anders J., et al., "Small Adjustments, Big Effects: Physiologic Considerations for the Clinical Implementation of Next Generation Resuscitative Balloon Occlusion of the Aorta (REBOA)", Journal of the American College of Surgeons (Oct. 2016); 223(4): e218-e219.

Davidson, Anders J., et al., "Potential benefit of early operative utilization of low profile, partial resuscitative endovascular balloon occlusion of the aorta (P-REBOA) in major traumatic hemorrhage", Trauma Surgery & Acute Care Open (2016); 1(1): 3 pages.

Davidson, Anders J., et al., "Potential benefit of early operative utilization of low profile, partial resuscitative endovascular balloon occlusion of the aorta (P-REBOA) in major traumatic hemorrhage", Trauma Surgery & Acute Care Open (Aug. 2016); 1(1): e000028.

Davidson, Anders J., et al., "A novel model of highly lethal uncontrolled torso hemorrhage in swine", Journal of Surgical Research (Oct. 2017); 218: 306-315.

Davidson, Anders J., et al., "Incremental balloon deflation following complete resuscitative endovascular balloon occlusion of the aorta results in steep inflection of flow and rapid reperfusion in a large animal model of hemorrhagic shock", Journal of Trauma and Acute Care Surgery (Jul. 2017); 83(1): 139-143.

Davidson, Anders J., et al., "The pitfalls of resuscitative endovascular balloon occlusion of the aorta: Risk factors and mitigation strategies", Journal of Trauma and Acute Care Surgery (Jan. 2018); 84(1): 192-202.

Detrano, Robert, et al., "Bayesian probability analysis: a prospective demonstration of its clinical utility in diagnosing coronary disease", (Mar. 1, 1984); Circulation 69(3): 541-547.

Dubose, Joe, "Evolving Paradigms in Vascular Injury Management", University of Maryland, Adams Crowley Shock Trauma Center (Mar. 17, 2016); 99 pages.

Extended European Search Report mailed on Dec. 18, 2020 for European Application No. 18788177.6, 8 pages.

Extended European Search Report mailed on Sep. 17, 2020 for European Application No. 18738917.6, 8 pages.

Fenton, Norman, et al., "Comparing risks of alternative medical diagnosis using Bayesian arguments", Journal of Biomedical Informatics (Aug. 2010); 43(4): 485-495.

Forte, Dominic M., et al., "Titrate to equilibrate and not exsanguinate! Characterization and validation of a novel partial resuscitative endovascular balloon occlusion of the aorta catheter in normal and hemorrhagic shock conditions", Journal of Trauma and Acute Care Surgery (Nov. 2019); 87(5): 1015-1025.

(56) References Cited

OTHER PUBLICATIONS

Forte, Dominic M., et al., "Validation of a novel partial resuscitative endovascular balloon occlusion of the aorta device in a swine hemorrhagic shock model: fine tuning flow to optimize bleeding control and reperfusion injury", Journal of Trauma and Acute Care Surgery (Jul. 2020); 89(1): 58-67.
Gantner, Dashiell, et al., "Intravenous fluids in traumatic brain injury: what's the solution?", Current Opinion in Critical Care (Aug. 2014); 20(4): 385-389.
Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010, 50 pages.
Hoareau, Guillaume L., et al., "Acute kidney injury following resuscitative endovascular balloon occlusion of the aorta: A systematic review", Journal of Endovascular Resuscitation and Trauma Management (2018); 2(2): 1-9.
Hoareau, Guillaume L., et al., "Endocrine Effects of Simulated Complete and Partial Aortic Occlusion in a Swine Model of Hemorrhagic Shock", Military Medicine (May-Jun. 2019); 184(5-6): e298-e302.
Hoareau, Guillaume L., et al., "Renal effects of three endoaortic occlusion strategies in a swine model of hemorrhagic shock", Injury (Nov. 2019); 50(11): 1908-1914.
Hoareau, Guillaume L., et al., "Automated partial versus complete resuscitative endovascular balloon occlusion of the aorta for the management of hemorrhagic shock in a pig model of polytrauma: a randomized controlled pilot study", Manuscript Draft submitted to Military Medicine on Mar. 6, 2020; 29 pages.
Hoareau, Guillaume L., et al., "Automated Partial Versus Complete Resuscitative Endovascular Balloon Occlusion of the Aorta for the Management of Hemorrhagic Shock in a Pig Model of Polytrauma: a Randomized Controlled Pilot Study", Military Medicine (Nov.-Dec. 2020); 185(11-12): e1923-e1930.
Holcomb, John B., et al., "Causes of Death in U.S. Special Operations Forces in the Global War on Terrorism: 2001-2004", Annals of Surgery (Jun. 2007); e245(6): 986-991.
Hoareau, Guillaume L., et al., "Esmolol reduces myocardial injury induced by resuscitative endovascular balloon occlusion of the aorta (REBOA) in a porcine model of hemorrhagic shock", Injury (Oct. 2020); 51(10): 2165-2171.
International Preliminary Report on Patentability for International Application No. PCT/US2021/022644, mailed Sep. 20, 2022, 17 pages.
Invitation to Pay Additional Fees for International Application PCT/US2022/033898, mailed Oct. 25, 2022, 21 pages.
Johnson, M. Austin, et al., "Partial resuscitative balloon occlusion of the aorta (P-REBOA): Clinical technique and rationale", The Journal of Trauma and Acute Care Surgery (Nov. 2016); 81(5 Suppl 2): S133-137.
Johnson, M. Austin, et al., "Small changes, big effects: the hemodynamics of partial and complete aortic occlusion to inform next generation resuscitation techniques and technologies", Journal of Trauma and Acute Care Surgery (Jun. 2017); 82(6): 1106-1111.
Johnson, M. Austin, et al., "The effect of resuscitative endovascular balloon occlusion of the aorta, partial aortic occlusion and aggressive blood transfusion on traumatic brain injury in a swine multiple injuries model", Journal of Trauma and Acute Care Surgery (Jul. 2017); 83(1): 61-70.
Johnson, M. Austin, et al., "Endovascular perfusion augmentation for critical care: partial aortic occlusion for treatment of severe ischemia-reperfusion shock", Shock (May 2019); 51(5): 659-666.
Johnson, M. Austin, et al., "Letter to the Editor Re: Titrate to equilibrate and not exsanguinate!", Journal of Trauma and Acute Care Surgery (Feb. 2020); 88(2): e107-e108.
Johnson, M. Austin, et al., "Letter to the editor: Response to letter from Dr. Martin et al.: Not ready for prime time: Intermittent versus partial REBOA for prolonged hemorrhage control in a highly lethal porcine injury model", Journal of Trauma and Acute Care Surgery (Jun. 2020); 88(6): e150-e151.
Johnson, M. Austin, et al., "Not ready for prime time: intermittent versus partial resuscitative endovascular balloon occlusion of the aorta for prolonged hemorrhage control in a highly lethal porcine injury model", Journal of Trauma and Acute Care Surgery (Feb. 2020); 88(2): 298-304.
Johnson, M. Austin, et al., "Response to the letter to the editor regarding: Titrate to equilibrate and not exsanguinate! Characterization and validation of a novel partial resuscitative endovascular balloon occlusion of the aorta catheter in normal and hemorrhagic shock conditions", Journal of Trauma and Acute Care Surgery (2020); 88(2): e108-e109.
Kalogeris, Theodore, et al., "Cell Biology of Ischemia/Reperfusion Injury", International Review of Cell and Molecular Biology (2012); 298: 229-317.
Kochanek, Patrick M., et al., "Guidelines for the acute medical management of severe traumatic brain injury in infants, children, and adolescents—second edition", Pediatric Critical Care Medicine (2012); 13(1 Suppl): S1-S2.
Kochanek, Patrick M., et al. "Guidelines for the Management of Pediatric Severe Traumatic Brain Injury, Third Edition: Update of the Brain Trauma Foundation Guidelines", Pediatric Critical Care Medicine (Mar. 2019); 20(3S): S1-S82.
Kuckelman et al. (2018). "Extending the golden hour for Zone 1 resuscitative endovascular balloon occlusion of the aorta: Improved survival and reperfusion injury with intermittent versus continuous resuscitative endovascular balloon occlusion of the aorta of the aorta in a porcine severe truncal hemorrhage model." J Trauma Acute Care Surg. 85(2): 318-326.
Leavesley, S. J. et al., "A device for performing automated balloon catheter inflation ischemia studies", Plos One (Apr. 25, 2014); 9(4): 9 pages.
Matsumura, Yosuke, et al., "Distal pressure monitoring and titration with percent balloon vol. feasible management of partial resuscitative endovascular balloon occlusion of the aorta (P-REBOA)", European Journal of Trauma and Emergency Surgery (Nov. 6, 2019); 47(4): 1023-1029.
Mcgreevy, David T, et al., "EndoVascular resuscitation and Trauma Management Specialists in Training—The Future of EVTM Education", Journal of Endovascular Resuscitation and Trauma Management (2022); 6(2): 77-78.
Mcgreevy, David T, et al., "The Use of a Single Proglide for Large Sheath Delivery Systems", Journal of Endovascular Resuscitation and Trauma Management (2022); 6(2): 116-118.
Mundasad, Smitha, "Balloon surgery stops fatal bleeding at roadside", BBC News, Jun. 17, 2014, [online], [retrieved on unknown]. Retrieved from the Internet URL: https://www.bbc.com/news/health-27868418, 3 pages.
Nieto-Calvache, Albaro Jose, et al., "Technical Considerations for the Use of REBOA in the Management of Placenta Accreta Spectrum", Journal of Endovascular Resuscitation and Trauma Management (2022); 6(2): 79-83.
Patel et al., "Bayesian Designs for Device Clinical Trials," MDG Forum, Waltham, MA., Nov. 3, 2010, downloaded from web page:http://www.cytel.com/pdfs/Pate1Bayes_Devices_Siides_11.18.10.pdf; 17 pages.
Patel, Nathan T. P., et al., "Endovascular Perfusion Augmentation for Critical Care Decreases Vasopressor Requirements while Maintaining Renal Perfusion", Shock: Injury, Inflammation, and Sepsis: Laboratory and Clinical Approaches 57(5); (May 1, 2022): 740-748.
PCT/US2018/013413, International Preliminary Report on Patentability, mailed Jul. 16, 2019, 18 pages.
PCT/US2018/013413, International Search Report and Written Opinion mailed Apr. 4, 2018, 20 pages.
PCT/US2018/028694, International Preliminary Report on Patentability, mailed Oct. 22, 2019, 10 pages.
PCT/US2018/028694, International Search Report and Written Opinion mailed Jul. 9, 2018, 11 pages.
PCT/US2021/021264, International Search Report and Written Opinion mailed Jun. 2, 2021, 17 pages.

(56) References Cited

OTHER PUBLICATIONS

PCT/US2021/021264, International Preliminary Report on Patentability, mailed Sep. 6, 2022, 16 pages.
PCT/US2021/022644, International Search Report and Written Opinion mailed Oct. 7, 2021, 28 pages.
PCT/US2021/022644, Invitation to Pay Additional Fees, mailed Aug. 16, 2021, 25 pages.
PCT/US2022/033896, Invitation to Pay Additional Fees, mailed Oct. 6, 2022, 18 pages.
Peiniger, Sigune, et al., "Balanced massive transfusion ratios in multiple injury patients with traumatic brain injury", Critical Care (Feb. 22, 2011); 15(1): 1-9.
Rasmussen, Todd E., et al., "Ahead of the curve: Sustained innovation for future combat casualty care", Journal of Trauma and Acute Care Surgery 79.4 (Oct. 2015): S61-S64.
Russo, Rachel, et al., "Emerging endovascular therapies for non-compressible torso hemorrhage", Shock (2016); 46(Supplement 1): 12-19.
Russo, Rachel M., et al., "Extending the golden hour: partial resuscitative endovascular balloon occlusion of the aorta in a highly lethal swine liver injury model", Journal of Trauma and Acute Care Surgery (Mar. 2016); 80(3): 372-380.
Russo, Rachel M., et al., "Partial resuscitative endovascular balloon occlusion of the aorta in swine model of hemorrhagic shock", Journal of the American College of Surgeons (Aug. 2016); 223(2): 359-368.
Russo, Rachel M., et al. "Two lives, one REBOA: hemorrhage control for urgent cesarean hysterectomy in a Jehovah's Witness with placenta percreta", Journal of Trauma and Acute Care Surgery (Sep. 2017); 83(3): 551-553.
Russo, Rachel M., et al., "A pilot study of chest tube versus pigtail catheter drainage of acute hemothorax in swine", Journal of Trauma and Acute Care Surgery (Dec. 2015); 79(6): 1038-1043.
Safe Study Investigators, "Saline or Albumin for Fluid Resuscitation in Patients with Traumatic Brain Injury", New England Journal of Medicine (Aug. 30, 2007); 357(9): 874-884.
Sam II, Albert, et al., "Blunt traumatic aortic transection: endoluminal repair with commercially available aortic cuffs", Journal of Vascular Surgery (Nov. 2003); 38(5): 1132-1135.
Sandgren, Thomas, et al. "The diameter of the common femoral artery in healthy human: Influence of sex, age, and body size", Journal of Vascular Surgery (Mar. 1999); 29(3): 503-510.
Screen capture from YouTube video clip entitled "Evolving Paradigms in Vascular Injury Management—Joseph DuBose—M.D.," 1 page, uploaded on Sep. 12, 2017; Presented on Mar. 22, 2016 by user "Surgery Grand Rounds 2016". Retrieved from Internet: https://www.youtube.com/watch?v=YfSYEM797Gg.
Shehab, Maysam, et al., "REBOA and the Open Abdomen", Journal of Endovascular Resuscitation and Trauma Management (2022); 6(2): 97-101.
Simon, Meryl A., et al., "A Case of Resuscitative Endovascular Balloon Occlusion of the Aorta (REBOA) Use in Penetrating Abdominal Aortic Injury", Journal of Endovascular Resuscitation and Trauma Management (2017); 1(1): 53-57.
Simon, Meryl A., et al., "Lower extremity cooling reduces ischemia-reperfusion injury following Zone 3 REBOA in a porcine hemorrhage model", Journal of Trauma and Acute Care Surgery (Sep. 2018); 85(3): 512-518.
Sohn, Vance Y., et al., "Demographics, treatment, and early outcomes in penetrating vascular combat trauma", Archives of Surgery (Aug. 18, 2008); 143(8): 783-787.
Spinella, Philip C., et al., "The Association of Blood Component Use Ratios With the Survival of Massively Transfused Trauma Patients With and Without Severe Brain Injury", Journal of Trauma and Acute Care Surgery (Aug. 2011); 71(2): S343-S352.
Sugiyama, Takuya, et al., "Transcatheter Arterial Embolization for Blunt Hepatic Trauma in a Preschooler", Journal of Endovascular Resuscitation and Trauma Management (2022); 6(2): 106-109.
Sumislawski, Joshua J, et al., "Resuscitative Endovascular Balloon Occlusion of the Aorta as a Bridge to Organ Donation after Blunt Trauma", Journal of Endovascular Resuscitation and Trauma Management (2022); 6(2): 102-105.
Tibbits, Emily M., et al., "Location is everything: the hemodynamic effects of REBOA in zone 1 versus zone 3 of the aorta", Journal of Trauma and Acute Care Surgery (Jul. 2018); 85(1): 101-107.
U.S. Appl. No. 63/277,428, inventors Fabro; Myra et al., filed Nov. 9, 2021.
Weingart, Scott, MD FCCM; "Podcast 170—the ER REBOA Catheter with Joe DuBose", EMCrit Blog (Mar. 21, 2016); [Online] Accessed on Aug. 30, 2022; Retrieved from the Internet, https://emcrit.org/emcrit/er-reboa/, 3 pages.
White, Joseph M., et al., "A new pressure-regulated, partial resuscitative endovascular balloon occlusion of the aorta device achieves targeted distal perfusion", Journal of Surgical Research (Dec. 2020); (256): 171-179.
Williams, Timothy K., et al., "Extending REBOA: endovascular variable aortic control (EVAC) in a lethal model of hemorrhagic shock", The Journal of Trauma and Acute Care Surgery (Aug. 2016); 81(2): 294-301.
Williams, Timothy K., et al., "Automated variable aortic control vs. complete aortic occlusion in a swine model of hemorrhage", The Journal of Trauma and Acute Care Surgery (Apr. 2017); 82(4): 694-703.
Williams, Timothy K., et al., ""What's in a Name?" A Consensus Proposal for a Common Nomenclature in the Endovascular Resuscitative Management and REBOA Literature", Journal of Endovascular Resuscitation and Trauma Management (2017); 1(1): 9-12.
Williams, Timothy K., et al., "A novel automated endovascular variable aortic control device to expand function of standard REBOA catheters", Journal of Endovascular Resuscitation and Trauma Management (2018); 2(3): 1-8.
Williams, Timothy K., et al., "Endovascular variable aortic control (EVAC) versus resuscitative endovascular balloon occlusion of the aorta (REBOA) in a swine model of hemorrhage and ischemia reperfusion injury", Journal of Trauma and Acute Care Surgery (2018); 85(3): 519-526.
Williams, Timothy Keith, et al., "Extending resuscitative endovascular balloon occlusion of the aorta: Endovascular variable aortic control in a lethal model of AQ1 hemorrhagic shock", Journal of Trauma and Acute Care Surgery (Apr. 30, 2016); 00(00): 1-8.
Non-Final Office Action mailed on Dec. 20, 2023, for U.S. Appl. No. 17/203,742, filed Mar. 16, 2021, 21 pages.
Chengod et al., "Selective left bronchial intubation and left-lung isolation in infants and toddlers: analysis of a new technique" J Cardiothorac Vasc Anesth. Oct. 2005;19(5):636-641.
Deaton, "Image-Guided Thrombectomy in Vascular Surgery" Endovascular Today Jul. 2005, 32-35.
Divani et al., "Blood Pressure Variability Predicts Poor In-Hospital Outcome in Spontaneous Intracerebral Hemorrhage" Stroke (2019) 50(8):2023-2029.
Extended European Search Report mailed on Mar. 25, 2024 for European Application No. EP23207427.8, 13 pages.
Final Office Action for U.S. Appl. No. 17/194,053 mailed Oct. 10, 2024, 27 pages.
Final Office Action for U.S. Appl. No. 17/203,742 mailed Oct. 16, 2024, 23 pages.
Final Office Action for U.S. Appl. No. 18/078,857 mailed Aug. 19, 2024, 7 pages.
Gerstenfeld et al., "Pulmonary vein isolation using a compliant endoscopic laser balloon ablation system in a swine model" J. Interv Card Electrophysiol (2010) 29:1-9.
Gu et al., "A new technique for sizing of atrial septal defects" Catheter Cardiovasc Interv. (1999) Jan. 46(1):51-57.
International Search Report and Written Opinion for International Application No. PCT/US2023/011298 dated Mar. 15, 2024, 23 pages.
Mathis et al., "Physical Characteristics of Balloon Catheter Systems Used in Temporary Cerebral Artery Occlusion" AJNR Am J Neuroradiol (1994) 15:1831-1836.
Non-Final Office Action for U.S. Appl. No. 18/078,857 dated Mar. 6, 2024, 9 pages.

(56) References Cited

OTHER PUBLICATIONS

Non-Final Office Action for U.S. Appl. No. 18/160,248 mailed on Oct. 9, 2024, 13 pages.
Non-Final Office Action for U.S. Appl. No. 18/193,369 mailed Jul. 2, 2024, 8 pages.
Notice of Allowance mailed on Sep. 11, 2024, for U.S. Appl. No. 18/078,857, filed Dec. 9, 2022, 9 pages.
Okell et al., "A theoretical framework for quantifying blood vol. flow rate from dynamic angiographic data and application to vessel-encoded arterial spin labeling MRI" Medical Image Analysis, vol. 17, Issue 8, pp. 1025-1036, Dec. 2013.
Owens et al., "Handbook of Endovascular Peripheral Interventions" Springer (2012), 462 pages.
Saab, "Applications of High-Pressure Balloons in the Medical Device Industry" Medical Device & Diagnostic Industry Magazine Sep. 2000, 18 pages.
Scott et al., "A novel fluoroscopy-free, resuscitative endovascular aortic balloon occlusion system in a model of hemorrhagic shock" J Trauma Acute Care Surg. Jul. 2013;75(1):122-128.
International Search Report and Written Opinion for PCT Application No. PCT/US2023/072764 mailed Dec. 20, 2024, 22 pages.
Mccarthy et al., "Automated Balloon Control in Resuscitative Endovascular Balloon Occlusion of the Aorta", IEEE Transactions on Biomedical Engineering, IEEE, USA (2019) 66(6):1723-1729.
Non-Final Office Action for U.S. Appl. No. 17/194,053 mailed on May 20, 2025, 24 pages.
Non-Final Office Action for U.S. Appl. No. 17/842,729 mailed Jun. 9, 2025, 18 pages.
Notice of Allowance for U.S. Appl. No. 17/203,742 mailed Jul. 2, 2025, 8 pages.
Notice of Allowance for U.S. Appl. No. 18/078,857, mailed on Jan. 7, 2025, 8 pages.
Notice of Allowance for U.S. Appl. No. 18/160,248 mailed on Feb. 6, 2025, 9 pages.
Notice of Allowance for U.S. Appl. No. 18/193,369 mailed Jan. 8, 2025, 7 pages.
"Blood Product: Essential Transfusions and Uses" (Date Unknown) [Retrieved from Internet on Mar. 20, 2026 at healthencyclopedeia.org/blood-product/]; 4 pages.
U.S. Appl. No. 18/454,673, Non-Final Office Action mailed Feb. 10, 2026; Inventor Williams, Timothy et al.; 23 pages.
U.S. Appl. No. 18/657,242, Non-Final Office Action mailed Mar. 12, 2026; Inventor Fabro; Myra et al.; 11 pages.

* cited by examiner (closed position)

(open position)

(open position)

(closed position)

- SINGLE "RE-USED" CONTROLLER SECTION THAT ATTACHES TO ONLY ONE CARTRIDGE
- IF NEED MORE THAN ONE CHANNEL, THEN JUST "STACK" THE CONTROLLERS
    - "LEGO BRICKS"
- EACH CONTROLLER HAS ITS OWN WIRELESS
    - TBD: WHEN STACKED, THEN CONTROLLER #2 WILL PROXY ITS WIRELESS TRAFFIC THROUGH CONTROLLER #1 TO AVOID CLOSE PROXIMITY ON TRANSCEIVERS

DEVICES, SYSTEMS, AND METHODS FOR BLOOD FLOW CONTROL

CROSS-REFERENCE TO RELATED APPLICATIONS

This application claims priority to U.S. Provisional Application Ser. No. 63/244,689, filed on Sep. 15, 2021, and U.S. Provisional Application Ser. No. 63/211,554, filed on Jun. 16, 2021, each of which is hereby incorporated by reference in its entirety.

GOVERNMENT SUPPORT

This invention was made with government support under grant FA8650-20-2-6116 and W81XWH-21-C-0058 awarded by the United States Air Force/Air Force Material Command. The government has certain rights in the invention.

TECHNICAL FIELD

This invention relates generally to the field of blood flow control systems, and in particular, to devices, systems, and methods for controlling blood flow and/or blood pressure within a blood vessel during endovascular procedures. The systems for blood flow control may include fluid delivery systems for the controlled delivery of fluids that may be configured to transition between various modes of operation, for example, automated and manual modes of operation. The fluid delivery systems may include various types of pumps configured to precisely meter fluids.

BACKGROUND

Over the years, there has been significant advancement in technologies to perform endovascular procedures. For example, endovascular catheters such as balloon catheters have been designed to be placed strategically in a blood vessel of a patient in order to partially and/or fully occlude a portion of a blood vessel. Occlusion may impede the blood flow (e.g., blood flow distal to the balloon) while augmenting blood pressure proximal to the balloon.

However, most existing endovascular catheters are controlled manually during an endovascular procedure. For instance, a user may manually inflate and/or deflate a balloon on the balloon catheter, using, for example, a syringe, to perform the procedure. The user may determine the amount of inflation and/or deflation by continuously monitoring the physiologic condition of the patient. The amount of inflation and/or deflation in turn may control the blood flow in the patient. However, relying solely on manual control (e.g., manual inflation and/or deflation) may make the procedure susceptible to human errors.

While automated balloon catheters that assist in controlling blood flow when placed in a patient's blood vessel have recently been developed, these automated balloon catheters are not capable of rapidly and easily switching between several modes of operation, for example, manually controlling the balloon volume with a syringe and manual mode control with a balloon volume controller and automatic modes with a controller. Additionally, existing automated balloon catheters do not provide precise feedback on pump position and movement, nor are they coupled with fluid delivery systems capable of providing precise control over balloon volume.

Accordingly, additional devices, systems, and methods for controlling blood flow in a blood vessel of a patient are needed. Furthermore, it would be beneficial to have new fluid delivery systems for the controlled delivery of various fluids, including fluids that may adjust the expansion/retraction of the blood flow control devices. It would also be useful for the new fluid delivery systems to be capable of controlling the delivery of fluids for other purposes such as the delivery of medication, intravenous fluids, and blood products.

SUMMARY

Systems for performing an endovascular procedure are described herein. The systems may comprise a blood flow control device, a syringe pump, and a controller. The blood flow control device may comprise an elongate body and an expandable member positioned at a distal end of the elongate body. The syringe pump may be in fluid communication with the expandable member. The syringe pump may comprise a cylindrical body and a plunger. The plunger may comprise an enlarged first end positioned within the cylindrical body and configured to move linearly therein. An elongate member extending from the enlarged first end may comprise a linear gear. The controller may be communicably coupled to the blood flow control device and releasably coupled to the syringe pump. The controller may comprise a housing and a circular gear positioned at least partially within the housing. The circular gear may be configured to engage the linear gear to actuate the syringe pump and adjust a volume of the expandable member.

In some variations, a system for an endovascular procedure comprises a blood flow control device, a syringe pump, and a controller. The blood flow control device may comprise an elongate body and an expandable member positioned at a distal end of the elongate body. The syringe pump may be in fluid communication with the expandable member. The syringe pump may comprise a linear gear and a mating feature. The controller may be communicably coupled to the blood flow control device. The controller may comprise a controller housing. The controller housing may comprise a recessed portion configured to receive the syringe pump, and a lever. The lever may have an open configuration in which an end of the lever is positioned away from the controller housing and a closed configuration in which the end of the lever engages with the mating feature on the syringe pump. The lever may be biased toward the open configuration. In the closed configuration, the lever may maintain an alignment between the linear gear on the syringe pump and a circular gear positioned at least partially within the controller housing and locks the syringe pump to the controller housing.

In some variations, a blood flow control device to control an expandable member in a blood vessel is described herein. The blood flow control device may comprise an elongate body, an expandable member positioned in a distal section of the elongate body, a first pressure sensor positioned proximal to the expandable member, and a second pressure sensor positioned distal to the expandable member. The proximal section of the elongate body may comprise an inner layer and an outer layer. A sensor wire associated with at least one of the first pressure sensor and the second pressure sensor may be routed between the inner layer and the outer layer.

In some variations, a blood flow control device to control an expandable member in a blood vessel is described herein. The blood flow control device may comprise an elongate body comprising a proximal portion with a first stiffness, a middle portion with a second stiffness, and a distal portion with a third stiffness, an expandable member positioned in the middle portion of the elongate body, a first pressure sensor positioned proximal to the expandable member and a second pressure sensor positioned distal to the expandable member, and an atraumatic tip positioned at the distal portion of the elongate body. The first stiffness may be greater than the second stiffness and the second stiffness may be greater than the third stiffness. The first pressure sensor and the second pressure sensor may be positioned in the middle portion of the elongate body.

In some variations, a method for performing an endovascular procedure is described herein. The method may comprise advancing an expandable member of a blood flow control device to a target location in a blood vessel of a patient, and rotating a circular gear positioned at least partially within a housing of a controller via the controller communicably coupled to the blood flow control device. Rotating the circular gear may translate a linear gear of a syringe pump fluidly coupled to the expandable member thereby adjusting a volume of the expandable member.

Also described herein are systems for the controlled delivery of fluids. The systems may be configured to deliver fluids in various modes, for example, a manual mode or an automated mode. In some variations, the systems may be configured to switch or transition between modes, for example, the automated mode may be switched to the manual mode of fluid delivery to allow a user or health care provider to intervene and manually control the size of an expandable member of a blood flow control device or the rate of fluid infusion to a patient. In further variations, the user may be able to temporarily override the automatic mode, and press a button on the system controller to manually adjust fluid delivery. After the manual adjustment, the system may revert to the automatic mode.

The fluid delivery systems may include one or more fluid delivery devices (e.g., one or more pumps) configured to precisely meter fluid therefrom to adjust the expansion of the expandable member of a blood flow control device, or to deliver fluids to a patient. The fluid delivery devices may be used in poorly resourced environments, for example, when there is minimal physician or other medical support, during interfacility patient transport, or during military field operations. In some instances, the fluid delivery devices may have a lower power demand than infusion pumps that employ peristaltic racks. The fluid delivery device may be a syringe pump that utilizes a rack and pinion system, a motor (e.g., a stepper motor), and a sensor such as a linear potentiometer, to track the position of the plunger and movement thereof during delivery of the fluid. Alternatively, the fluid delivery device may be a pressure differential pump that includes a flow restrictor and a pressure sensor that controls delivery of fluid from a fluid reservoir. Methods including fluid delivery using the syringe or pressure differential pumps are also described.

When the fluid delivery device is a syringe pump, the syringe pump may comprise a cylindrical body and a plunger partially disposed within the cylindrical body, where the plunger comprises a linear gear. A circular gear configured to linearly advance the plunger when engaged with the linear gear, a sensor configured to detect a position of the plunger within the cylindrical body and track movement of the plunger during delivery of a fluid therefrom, and a pump controller configured to control actuation of the circular gear based on the position of the plunger detected by the sensor may also be included in the fluid delivery system. The linear gear may include a plurality of teeth configured to engage the circular gear, which may be coupled to a motor (e.g., a stepper motor). Various types of sensors may be employed that detect the position of the plunger within the cylindrical body and track movement of the plunger. In one variation, the sensor is a linear potentiometer.

Additionally, the pump controller may comprise a housing configured for removable attachment to the cylindrical body. The housing may include a user interface. The user interface may be configured to adjust one or more parameters of the pump controller. In some variations, the housing may include a display that presents information related to a medication or other fluid being delivered.

The syringe pump may deliver various types of fluid. In some instances, the cylindrical body of the syringe pump may be prefilled with the fluid. In other instances, the cylindrical body may be filled with the fluid just prior to delivery. Exemplary fluids include without limitation, normal saline, lactated ringers solution, D5 W, a medication, blood, or a blood product.

When the fluid delivery system includes a pressure differential pump, the pressure differential pump may include a reservoir containing a fluid, a housing coupled to the fluid reservoir and comprising a flow restrictor and a first pressure sensor, and a pump controller configured to control opening of the flow restrictor based on a pressure measured by the first pressure sensor. The housing may include a user interface. The user interface may be configured to adjust one or more parameters of the pump controller. In some variations, the housing may include a display that presents information related to a medication or other fluid. In other variations, the housing may include a second pressure sensor.

The fluid reservoir of the pressure differential pump may be removably coupled to the housing. Similar to the syringe pump, examples of fluids that may be contained within and delivered from the fluid reservoir of the pressure differential pump include, but are not limited to, normal saline, lactated ringers solution, D5 W, a medication, blood, or a blood product.

In some variations, the fluid delivery systems may include a first pump, for example, a first syringe pump or a pressure differential pump for the automated delivery of a fluid to a patient. In addition to the first fluid pump or a pressure differential pump, the systems may include a blood flow control device comprising a second syringe pump or another pump that may be either a syringe pump or a second pressure differential pump. The blood flow control device may also comprise an expandable member. Fluid such as normal saline may be pumped from the syringe or pressure differential pump and used to expand the expandable member, e.g., an expandable balloon.

Methods for fluid delivery are further described herein. When a syringe pump is used, the method may comprise delivering a fluid to a patient from the syringe pump, where the syringe pump comprises a cylindrical body, a plunger partially disposed within the cylindrical body, a sensor, and a pump controller, detecting the position of the plunger, and tracking linear movement of the plunger during delivery of the fluid using the sensor. In this instance, the sensor may be a linear potentiometer, and the pump controller may control actuation of the plunger based on the position and/or linear movement of the plunger detected by the linear potentiometer. Instead of or in addition to tracking linear movement of the plunger, movement of the motor may be tracked during fluid delivery. Non-limiting examples of fluids that may be delivered using the syringe pump include normal saline, lactated ringers solution, D5 W, a medication, blood, or a blood product. In one variation, normal saline may be used to expand an expandable member of a blood flow control device. The methods may include delivering a fluid to treat a patient in a hospital or field care setting.

When a pressure differential pump is used, the method may comprise delivering a fluid from the pressure differential pump, where the pump comprises a reservoir containing the fluid, and a housing coupled to the fluid reservoir. The housing may include a flow restrictor, a first pressure sensor, and a pump controller. Opening of the flow restrictor may be controlled based on a pressure measured by the first pressure sensor. In some variations, the housing may include a second pressure sensor. Non-limiting examples of fluids that may be delivered using the syringe pump include normal saline, lactated ringers solution, D5 W, a medication, blood, or a blood product. In one variation, normal saline may be used to expand an expandable member of a blood flow control device. In some variations, the method may include delivering a fluid in a hospital or field care setting.

BRIEF DESCRIPTION OF THE DRAWINGS

In FIGS. 14A-14C, the magnets of the coupling and alignment mechanism face E/W (East or West). In FIGS. 14D-14F, the magnets face N/S (North or South).

FIG. 17C depicts an expanded perspective view of the lever; FIG. 17D is a perspective view of the system controller showing the lever in an open position; FIG. 17E is a perspective view of the system controller showing the lever in a closed position; and FIGS. 17F and 17G show cross-sectional views of FIGS. 17F and 17G, respectively.

FIG. 25A shows the syringe coupled to the pump housing; FIG. 25B shows the housing alone; and FIG. 25C provides a cross-sectional view of the syringe pump showing an exemplary rack and pinion system.

FIG. 29A is a graph showing the linear correlation between voltage output and fluid pressure from an IV bag; FIG. 29B is a graph showing the relationship between orifice diameter and flow rate of a fluid (saline); and FIG. 29C is a graph showing the relationship of flow rate and pressure differential based on the duty cycle.

DETAILED DESCRIPTION

Figure 1A:
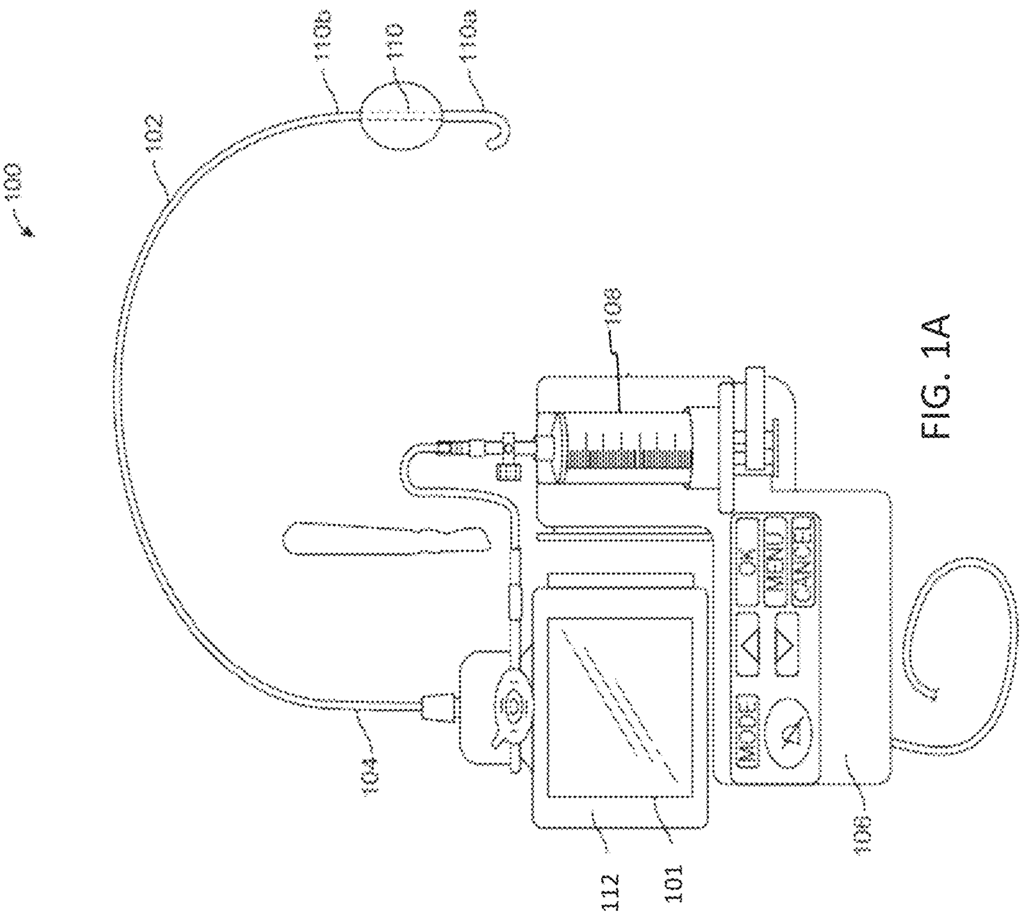
FIG. 1A illustrates an exemplary variation of a blood flow control system.

Balloon catheters are therapeutic devices to treat shock in patients. Balloon catheters may be strategically placed within a blood vessel (e.g. aorta) of a patient in need of hemodynamic support (e.g. hemorrhagic shock). An expandable member included on the balloon catheter may be inflated and/or deflated to partially or fully occlude the blood vessel. The amount of occlusion may regulate the blood flow to vital organs in the patient's body proximal to the balloon. This in turn may help maintain adequate oxygen delivery to the vital organs.

Conventionally, the inflation and/or deflation of the expandable member may be performed manually. For example, a fluid (e.g., saline, etc.) and/or a compressed gas (e.g., carbon dioxide, etc.) may be introduced into the expandable member such that the expandable member attains a specific volume that corresponds to an amount of occlusion in the blood vessel. A user (e.g., operator, surgeon, etc.) may use a syringe to inject or remove the fluid and/or the compressed gas from the expandable member in order to inflate or deflate the expandable member. The amount of fluid to be injected or removed may be determined by continuously monitoring the physiologic conditions of the patient. For example, one or more sensors may determine the blood pressure upstream from occlusion, downstream from occlusion, and/or at the site of the occlusion. The user may monitor the sensor data and may adjust the amount of fluid and/or compressed gas injected or removed from the expandable member accordingly. By adjusting the amount of fluid and/or compressed gas in the expandable member, the user adjusts the volume of the expandable member, thereby adjusting the amount of occlusion in the blood vessel. However, such continuous manual control of the expandable member may be prone to human errors.

To combat this, more recently, automated balloon catheters have been developed to automate the inflation and/or deflation of the expandable member. In automated balloon catheters, a syringe may be coupled to an actuator that may be used to automatically inject or remove fluid and/or compressed gas from the expandable member.

However, conventional automated balloon catheters do not allow a user to initially manually control the volume of the expandable member and easily transition to automatic control using the same pump, or to revert back to manual control of the volume of the expandable member during a procedure. For instance, during an endovascular procedure, as the balloon catheter is automatically controlled, there may be situations when it may be advantageous to allow the user to intervene and manually control the volume of the expandable member. For example, in some situations, it may be advantageous to allow the user to manually inject or remove fluid and/or compressed gas from the expandable member with the syringe.

Additionally, conventional automated balloon catheters do not allow for precise control of the volume of the expandable member. Furthermore, components of existing balloon catheter systems do not have reduced form factor. For example, the components of existing systems are often bulky, making them difficult to use and transport.

Described herein are improved blood flow control devices, systems, and methods that provide for automated and manual control of the expandable member as desired and easy transition between multiple modes of operation. The devices, systems, and methods provide for enhanced control of the volume of the expandable member. Moreover, the system and devices are designed to have a reduced form factor, allowing for compact integration of the components of the system and devices, thereby improving flexibility and maneuverability of parts of the system and devices during endovascular procedures.

Blood Flow Control System

Described herein are systems for controlling blood flow through a blood vessel of a patient, such as, for example, a patient suffering from stroke, cardiac arrest, or uncontrolled hemorrhage. Generally, the system may comprise a blood flow control device, a system controller, and a pump. Various types of pumps may be employed with the systems, as further described below. In some variations, the blood flow control system includes a syringe pump. The blood flow control device may comprise an elongate body and an expandable member positioned at a distal end of the elongate body and one or more sensors configured to measure physiologic conditions of the patient. The blood flow control device may also include a device controller to house electronic components.

The blood flow control device may be releasably and/or communicably coupled to the system controller. The system controller may comprise a housing. At least a portion of the housing may be configured to receive a pump, such as a syringe pump. The syringe pump may be releasably coupled to the housing of the system controller, for example, by means of a lever. The system may comprise various mechanisms for metering fluid, such as a rack and pinion, to expand and/or contract the expandable member. For example, the system controller may comprise an actuator (e.g., a circular gear or pinion) that may be configured to interact with a corresponding actuation element (e.g., linear gear or rack) on the pump, such that together, the actuator and actuation element may be used to expand and/or contract the expandable member (e.g., by delivering or removing fluid from the expandable member). In variations utilizing a syringe pump and a rack and pinion system, a circular gear may be positioned at least partially within the housing of the system controller and the plunger of the syringe pump may comprise the linear gear. The circular gear may be configured to engage with the linear gear to actuate the syringe pump and adjust a volume of the expandable member. In some variations, the system controller may include one or more controls (e.g., buttons) to enable a manual mode of operation (as further described below) for the system controller.

As discussed above, the pump may be releasably coupled to the system controller. In variations comprising a syringe pump, the syringe pump may comprise a plunger and a cylindrical body that is in fluid communication with the expandable member. In some variations, the system, and for example, the syringe pump, may include a sensor to track the position or movement of one or more components, including, for example, the plunger, the motor, any of the gearing in the system, etc.

In some variations, the blood flow control system may be manually operated (e.g., hand operated). For example, in some instances, such as when the controller of the blood flow control system shutdowns and when a user prefers to manually control a volume of the expandable member, the user may decouple the syringe pump from the system controller. The user may manually (e.g., by hand) operate the syringe pump without using the system controller, thereby manually inflating and/or deflating the expandable member.

Additionally, the system controller may be configured to operate the blood flow control system. In instances when the system controller operates the blood flow control system (i.e., when the pump is not being operated by hand), the blood flow control system may be configured to operate in two modes—an automatic mode and a manual mode. In the automatic mode, the system controller may control the actuator to control the movement of the pump to inflate and deflate the expandable member. Therefore, a volume of the expandable member may be controlled by the system controller. The system controller may control the actuator based on a comparison of target physiologic conditions and sensor data indicating the physiologic conditions of the patient received from the sensors during the procedure. In the manual mode, the system controller may not autonomously control the actuator of the system. Instead, the system controller may include one or more user controls (e.g., on the surface of the system controller, on a user interface with a touch screen, etc.) that may be operably and/or communicably coupled to the actuator, which may be coupled to the actuation element of the pump. A user may utilize the user controls to control the actuator so as to inflate and deflate the expandable member. Thus, the manual mode of the controller requires user input to adjust the volume of the expandable member.

It should be readily apparent that the manual mode of operation of the controller is different from a user "manually" (e.g., hand operated) controlling the pump without use of the system controller. In the manual mode of operation of the controller, the user may use the system controller to inflate and deflate the expandable member. In contrast, in instances in which the system controller may shutdown the operation of the blood flow control system or a user otherwise prefers to manually control the volume of the expandable member, a user may decouple the pump from the blood flow control system and may "manually" (e.g., by hand) inflate and deflate the expandable member without using the controller or a user interface of the blood flow control system.

Figure 1B:
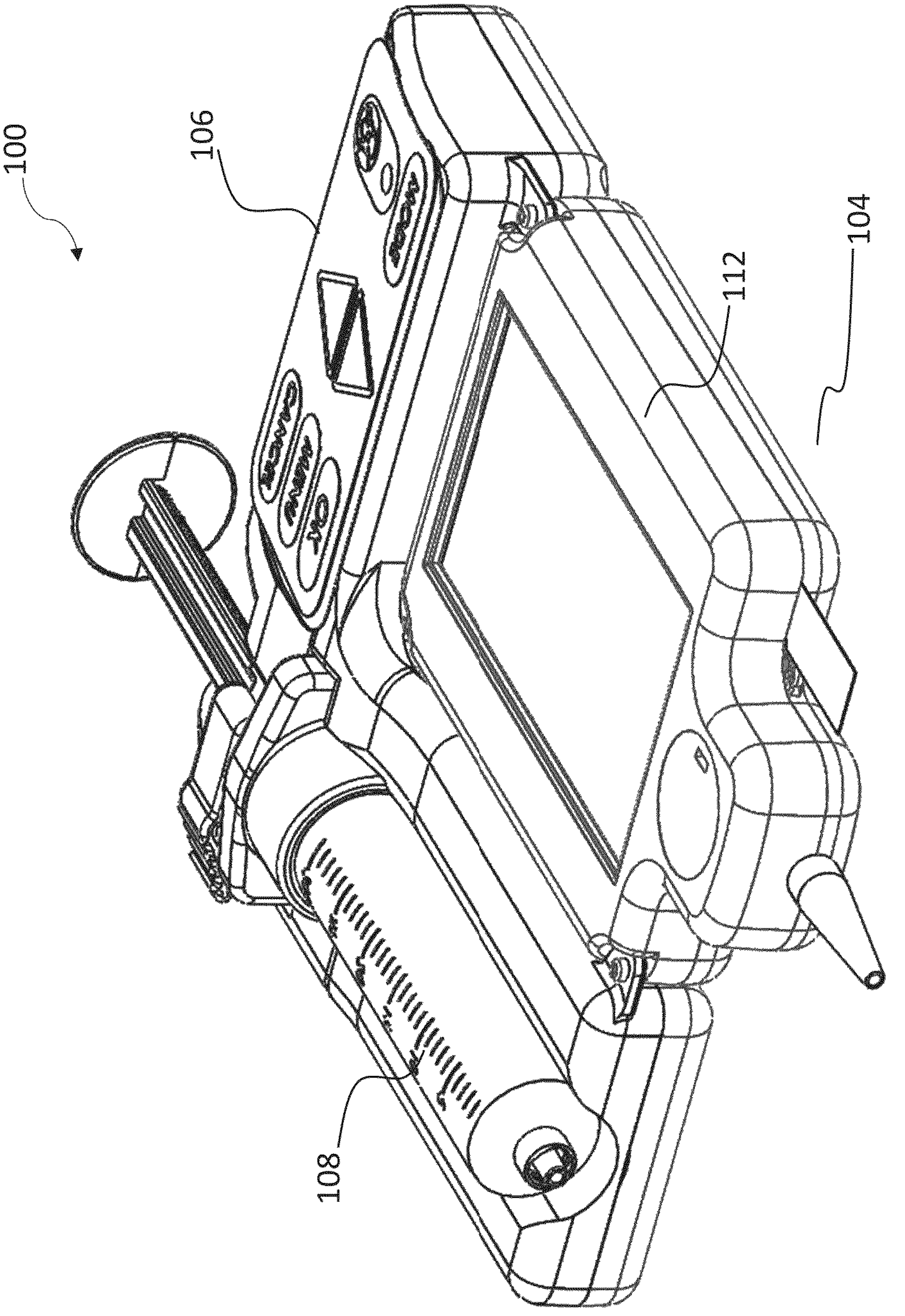
FIG. 1B illustrates another exemplary variation of a blood flow control system.

Turning now to the figures, FIG. 1A and FIG. 1B illustrate an exemplary variation of a blood flow control system 100. As shown there, the blood flow control system 100 may comprise a blood flow control device 104 and a system controller 106. The blood flow control device may comprise an elongate body 102, such as, for example, a catheter, an expandable member 110, such as, for example, a balloon, and a controller, such as, a device controller 112, which may comprise a user interface 101. The blood flow control device 104 may additionally comprise or otherwise be operably coupled to a pump 108. The expandable member 110 may be disposed on, coupled to, integrated with, attached to, or otherwise affixed to the elongate body 102. The blood flow control device 104 may also comprise one or more sensors 110*a* and 110*b*. In variations in which the blood flow control device 104 comprises one or more sensors, the sensors may be disposed on, coupled to, integrated with, attached to, or otherwise affixed to the elongate body 102. In other variations, one or more of the sensors may be external to or separate from the blood flow control device 104. The sensor(s) may be operably coupled to one or both of the device controller 112 and the system controller 106. In some variations, the sensor(s) and thereby the blood flow control device 104 may be communicably coupled to the system controller 106 (e.g., via the device controller 112). The expandable member 110 may be fluidly coupled to the pump 108. The system controller 106 may include an actuator, such as a circular gear (described in detail herein), to actuate the pump 108. The actuator may be controlled by a processor in one or more controllers (e.g., the system controller 106, the device controller 112). While described above as two controllers, a device controller 112 and a system controller 116, it should be appreciated that a single controller could be utilized to perform the functions of both the device controller 112 and the system controller 116 described herein, and/or any of the functions of the device controller 112 could be performed by the system controller 116 and vice versa. Accordingly, any of the components described herein as coupled to either the device controller 112 or the system controller 116 may be coupled to the other of the device controller 112 and the system controller 116, or to both controllers, as the case may be.

Blood Flow Control Device

As mentioned above, the blood flow control device may comprise an elongate body, an expandable member coupled to the elongate body, one or more sensors coupled to or integrated with a shaft of the elongate body, and a device controller. The blood flow control device may be configured to occlude blood vessels for indications such as stroke, cardiac arrest, hemorrhage control, and/or the like. For example, the blood flow control device (e.g., the elongate body of the blood flow control device) may be advanced to a desired location in a blood vessel and the expandable member may be inflated and/or deflated during the endovascular procedure to partially or fully occlude the blood vessel.

In some variations, blood flow control devices may be used during procedures for removal of a thrombus from an artery or vein. Some blood flow control devices may be used to support thrombectomy catheters that are advanced into the vasculature of the brain to remove a blood clot causing a stroke. An expandable member on the end of a support or guide catheter (e.g., elongate body) may be inflated to occlude a blood vessel to momentarily stop blood flow while the thrombus or blood clot is removed. In such variations, as discussed above, the blood flow control devices may have to precisely control the delivery of fluids into and removal of fluids from the expandable member.

Figure 2:
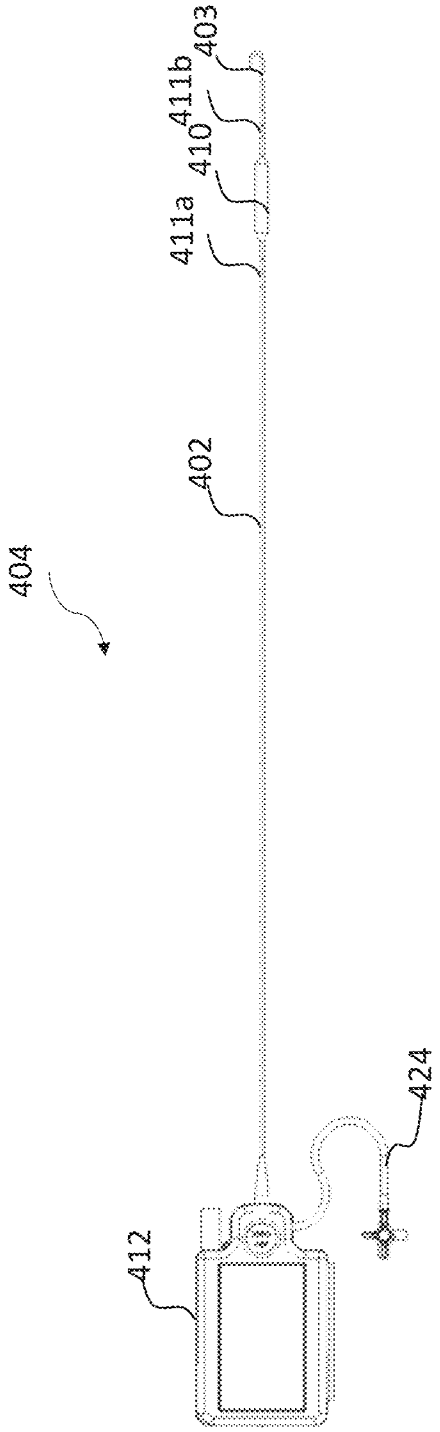
FIG. 2 illustrates an exemplary variation of a blood flow control device.

FIG. 2 illustrates an exemplary variation of a blood flow control device 404 (e.g., structurally and/or functionally similar to blood flow control device 104 in FIG. 1A and FIG. 1B). The blood flow control device 404 includes an elongate body 402 (e.g., structurally and/or functionally similar to elongate body 102 in FIG. 1A) with an expandable member 410 (e.g., structurally and/or functionally similar to expandable member 110 in FIG. 1A) at the distal end of the elongate body 402. The proximal end of the elongate body may be coupled to a device controller 412 (e.g., structurally and/or functionally similar to device controller 112 in FIG. 1A and FIG. 1B) that houses one or more electronic components. The device controller 412 may include a user interface to display and/or monitor the occlusion status of the blood vessel. In some variations, a fluidic path 424 may be used to connect the blood flow control device 404 to a syringe pump (e.g., pump 108 in FIG. 1A and FIG. 1B). The elongate body 402 may include one or more sensors to measure physiologic conditions of the patient. The sensors may be integrated with, attached to, or otherwise coupled to the elongate body 402. For example, the elongate body 402 may include a proximal sensor 411*b* and a distal sensor 411*a*. The terms "proximal" and "distal," as used herein in relation to sensor (s) and/or particular localized blood pressure readings, refer to blood flow directionality from the heart. That is, "proximal" is closer to the heart while "distal" is further from the heart. This is not to be confused with the reversed usage of the terms when described from the perspective of a medical device such as a catheter (e.g., elongate body 402), where the "distal end" of the medical device would commonly be understood as the end with the expandable member 110 furthest from the system controller 106 and the "proximal end" would be understood as the end closer to the user. The terms "proximal" and "distal" as used herein in relation to components of the blood flow control system other than the relative locations of the sensors and/or particular localized blood pressure readings, refer to the typical usage from the perspective of a medical device.

In some variations, the blood flow control device 404 may be used as a standalone device. For instance, the blood flow control device 404 may be uncoupled (communicably, electrically, and/or mechanically) from the system controller (e.g., system controller 106 in FIG. 1A and FIG. 1B) and the device controller may be used to adjust the volume of the expandable member, or the volume may be adjusted manually by a user via the pump (108) (i.e., without the use of a controller). The blood flow control device 404 may be configured to be in fluid communication with a pump, such as a syringe pump, via the fluidic path 424. The expandable member 410 may be manually inflated and/or deflated by injecting and/or removing fluid via the fluidic path 424 using the pump. The blood flow control device 404 may be coupled to the system controller as described further below to automatically control the inflation and deflation of the expandable member 410. In some variations, the distal end of the elongate body 402 may comprise an atraumatic tip 403 (e.g., a rounded or J-tip) to guide the elongate body 402 into the blood vessel of a patient.

Elongate Body

Referring back to FIG. 1A, the elongate body 102 may comprise a shaft sized and shaped for placement within a blood vessel (e.g., aorta, vein, etc.) of a patient. In some variations, the elongate body 102 may have a length sufficient to reach a patient's aorta via the femoral or radial artery. For example, in some variations, the elongate body 102 may be a catheter configured to be inserted into the femoral or radial artery and to extend through the patient's vasculature into the aorta. In some variations, the elongate body 102 may be steerable. For example, in some variations, the elongate body 102 may be mechanically coupled to knobs, levers, pullwires, and/or the like that may be used to steer or otherwise deflect a distal end of the shaft of the elongate body 102. In some variations, the elongate body 102 may include one or more lumens (not shown in FIG. 1A and FIG. 1B) therethrough. The lumen(s) may be partial lumen(s) (e.g., open on one end) and may be disposed within or lie within the movable shaft. Alternatively, the movable shaft may define one or more lumen(s). In some variations, the lumen(s) may include an intake or inflation lumen and an exhaust or deflation lumen to deliver fluid and/or compressed gas to the expandable member and to recover the fluid and/or compressed gas from the expandable member 110, respectively. In some variations, a single lumen may be used as both an intake or inflation lumen and an exhaust or deflation lumen such that a single lumen is used for delivering and recovering fluid and/or compressed gas from the expandable member.

As mentioned above, the elongate body 102 may be sized and shaped for advancement to and placement at least partially within a target location within a blood vessel. The elongate body may have any diameter and length suitable for advancement to the target location in the blood vessel.

For example, the elongate body may have a diameter between about 2 mm and about 36 mm. In some variations, the diameter may be for example between about 3 mm and about 25 mm, between about 4 mm and about 20 mm, and between about 5 mm and about 15 mm (including all values and sub-ranges therein). In some variations, the diameter may be for example between about 6 mm and about 10 mm. The elongate body may have a length between about 1 cm and about 110 cm. In some variations, the length may be for example between about 10 cm and about 105 cm, between about 20 cm and about 100 cm, between about 30 cm and about 90 cm, between about 40 cm and about 80 cm, and between about 50 cm and 70 cm (including all values and sub-ranges therein).

Figure 3:
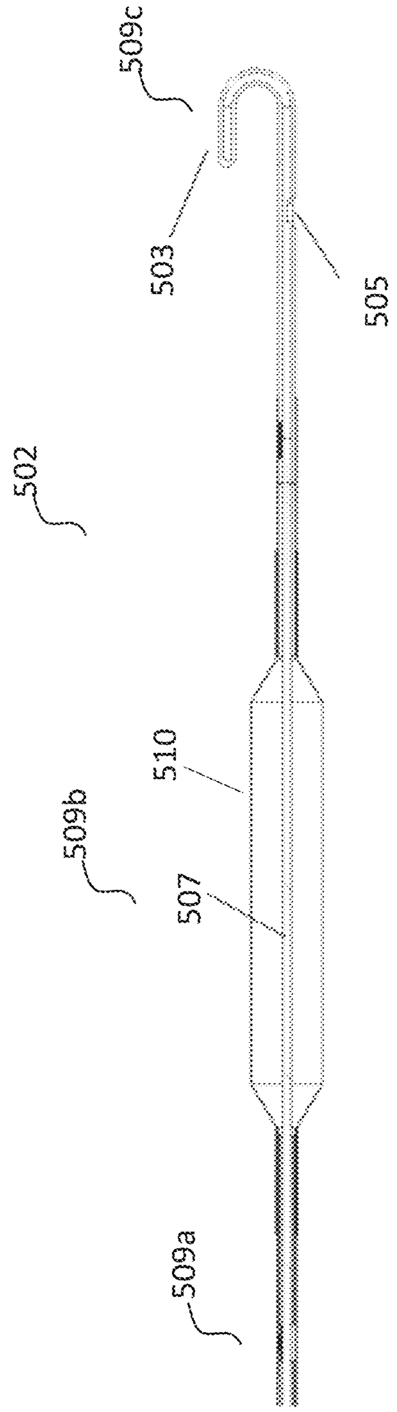
FIG. 3 illustrates an exemplary variation of an elongate body of a blood flow control device.

FIG. 3 illustrates an exemplary variation of an elongate body 502 (e.g., structurally and/or functionally similar to elongate body 102 in FIG. 1A). In some variations, the elongate body 502 may consist of segments with varying material properties, such as, for example, variable stiffness, and/or varying material layering. For instance, the elongate body 502 may comprise a proximal portion 509*a*, a middle portion 509*b*, and a distal portion 509*c*. The proximal portion 509*a* may be the portion closest to the device controller, the middle portion 509*b* may be between the proximal portion and the distal portion, and the distal portion 509*c* may comprise the atraumatic distal tip. The expandable member and the sensor(s) may be coupled to or otherwise positioned in the middle portion 590*c* of the elongate body. In some variations, the stiffness of the elongate body 502 may decrease from the proximal portion 509*a* to the distal portion 509*c*. In these variations, the proximal portion 509*a* may be the stiffest portion of the elongate body, the middle portion 509*b* may have a stiffness that is less than the stiffness of the proximal portion 509*a* but greater than a stiffness of the distal portion 509*c*, and the distal portion 509*c* may have the lowest stiffness. Put another way, the flexibility of the elongate body 502 may increase along a length of the elongate body 502 from the proximal end to the distal end. The middle portion 509*b* may be more flexible than the proximal portion 509*a*, and the most flexible portion of the elongate body 502 may be the distal portion 509*c* of the elongate body 502 with the atraumatic tip 503. The proximal portion 509*a* of the elongate body 502 may have a length between about 45 cm and about 55 cm such as for example, between about 49 cm and about 52 cm, between about 50 cm and 51 cm (including all values and sub-ranges therein), the middle portion 509*b* of the elongate body 502 may have a length between about 5 cm and about 10 cm, and the distal portion 509*c* of the elongate body 502 may have a length between about 5 cm and about 10 cm. The proximal portion 509*a* of the elongate body 502 may have a durometer between about 72 D and about 90 D, the middle portion 509*b* of the elongate body 502 may have a durometer between about 63 D and about 72 D, and/Or the distal portion 509*c* of the elongate body 502 may have a stiffness between about 40 D and about 55 D. The atraumatic tip 503 may further be composed of polymer segments of varying stiffness/durometer. The atraumatic tip 503 may have a durometer between about 30 D and about 40 D. In some variations, the layer of the portion of the elongate body may contribute to the stiffness of the portion of the elongate body. In some variations, the durometer of each layer, and the layering, may contribute to the stiffness of the portion of the elongate body.

As seen in FIG. 3, the elongate body 502 may include a core 507 that may increase the column strength of the elongate body 502 through all or a portion of the elongate body. In some variations, the core 507 may span the entire length of the elongate body 502, while in other variations, only a portion of the elongate body 502 may comprise the core 507 (e.g., only the proximal portion, only the middle portion, only the proximal portion and the middle portion). For example, in some variations, the proximal and middle portions of the elongate body 502 may comprise the core 507, but the core 502 may terminate at the distal portion of the elongate body 502 so as to permit transition to the atraumatic tip 503. The core 507 may be made of any material suitable to increase the column strength of the elongate body 502, such as, for example, a metal, a metal alloy (e.g., stainless steel, nitinol, etc.), a polymer, a combination thereof or the like.

Figure 4:
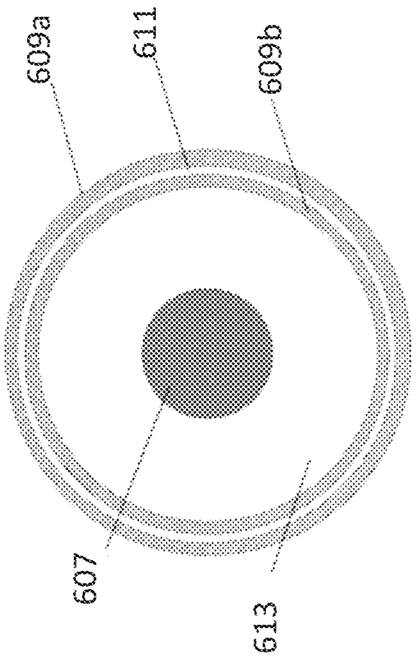
FIG. 4 illustrates an exemplary variation of a cross-section of a proximal portion of an elongate body of a blood flow control device.

One or more portions of the elongate body may comprise a plurality of layers (e.g., two, three, four, or more), and all portions of the elongate body may comprise the same layers, or the layers may differ between different portions of the elongate body. For example, in some variations, the proximal portion 509*a* of the elongate body 502 may comprise a plurality of layers. FIG. 4 illustrates an exemplary variation of a cross-section of the proximal portion 509*a* of the elongate body 502. As seen in FIG. 4, the proximal portion of the elongate body may include an inner layer 609*b* and an outer layer 609*a*. The inner layer 609*b* may be an inner shaft and the outer layer 609*a* may be an outer shaft such that the diameter of the outer shaft is greater than the diameter of the inner shaft. The elongate body may include an annular space 611 between the outer layer 609*a* and the inner layer 609*b*, and may comprise a lumen 613. The elongate body may also include a core 607 (e.g., structurally and/or functionally similar to core 507 in FIG. 5), which may, for example, comprise a metal alloy, and may be positioned within the lumen 613. A space between the core 607 and the inner layer 609*b* may form a lumen 613. In some variations, the core 607 may be coupled to (e.g., anchored and/or secured at) the proximal portion 509*a* of the elongate body (e.g., in a hub) and the distal portion 509*c* of the elongate body. The inner layer 609*b* may surround the lumen 613 (e.g., the lumen 613 may otherwise be formed from the inner layer 609*b*), and thus, in some variations, the lumen 613 may be formed between the core 607 and the inner layer 609*b*. In some embodiments, and as seen in FIG. 4, the elongate body may include only a single lumen 613, while in other embodiments, the elongate body may comprise a plurality of lumens (e.g., two, three, four or more). The lumen 613 may be configured to transfer fluid to and from the expandable member at the distal portion of the elongate body. Thus, the lumen 613 may be in fluid communication with a pump and with the expandable member of the blood flow control device. In some variations, the elongate body may include lumens at either side of the outer layer 609*a* spanning the length of the elongate body so as to transmit fluid for inflation and deflation of the expandable member. For example, the elongate body may include a first lumen at a first side of the outer layer to transmit fluid for inflation and a second lumen at a side opposite to the first side of the outer layer to transmit fluid for deflation of the expandable member.

The inner layer 609*b* may comprise any material suitable for transmitting fluid to the expandable member. For example, in some variations, the inner layer 609*b* may comprise one or more thermoplastic materials, such as, for example, Polytetrafluoroethylene (PTFE), polyimide, and Pebax®. In some variations, the inner layer 609*b* may be a composite of PTFE, polyimide, and Pebax®. In some variations, the inner layer 609*b* may be a high-strength dielectric material such as polyimide. The high-strength dielectric material may provide stiffness as well as insulating properties. In some variations, the innermost surface of the inner layer 609*b* may be hydrophobic (e.g., made from a hydrophobic material such as PTFE and/or coated with a hydrophobic coating). Accordingly, when fluid is transmitted to the expandable member, fluid absorption by the inner layer 609*b* may be advantageously reduced. In some variations, the outermost surface of the inner layer 609*b* may be configured to facilitate thermal and/or adhesive bonding with segments and/or components that may be adjacent to the outermost surface of the inner layer 609*b*. For example, in some variations, the inner layer 609*b* may comprise Pebax® or other nylon-blend materials that have favorable properties for thermal bonding and/or adhesive bonding. Additionally or alternatively, the outer layer 609*a* may be configured to facilitate thermal and/or adhesive bonding with the outermost surface of inner layer 609*b*. For example, the outer layer 609*a* may comprise a nylon-blend polymer with favorable properties for thermal and/or adhesive bonding.

In some variations, the outer layer 609*a* may also include a metallic or polymeric reinforcement, such as a stainless steel braid. The metallic or polymeric reinforcement may enhance the radial strength of the composite of polymers in a tubular form. This may prevent the elongate body from kinking when it is traversed through the blood vessel and may prevent the elongate body from collapsing under high deflation vacuum.

As discussed above, the elongate body may include one or more sensors, such as, for example, sensors proximal and distal to the expandable member. In some variations, one or more sensor wires associated with the sensors may be routed through the elongate body. For example, in some variations, one or more sensor wires may be positioned within or otherwise routed through the annular space 611. This may advantageously decrease the size and/or complexity of the elongate body by allowing for the elongate body to have a single lumen (i.e., within the inner layer 609*b*) (instead of a multi-lumen extrusion). Accordingly, this may contribute to reduced form factor of the elongate body. In other words, the elongate body may be designed to be compact without the need for extra lumens to route sensor wires. Additionally, routing the sensor wires through the annular space 611 may make the elongate body more kink-resistant. In some variations, sensor wires may be coupled alongside the core 607 and may be protected by a polymeric layer such as Polyethylene terephthalate (PET) for the entire span of the elongate body. This may assist in separating the sensor wires from the fluid transfer lumen. In some variations, the sensor wires may be disposed alongside the core 607 (e.g., the sensor wires may run parallel to the core 607). Additionally or alternatively, the sensor wires may surround and/or may be wrapped around the core 607. For example, the sensor wires may surround the core 607 by forming a helical shape.

Figure 5:
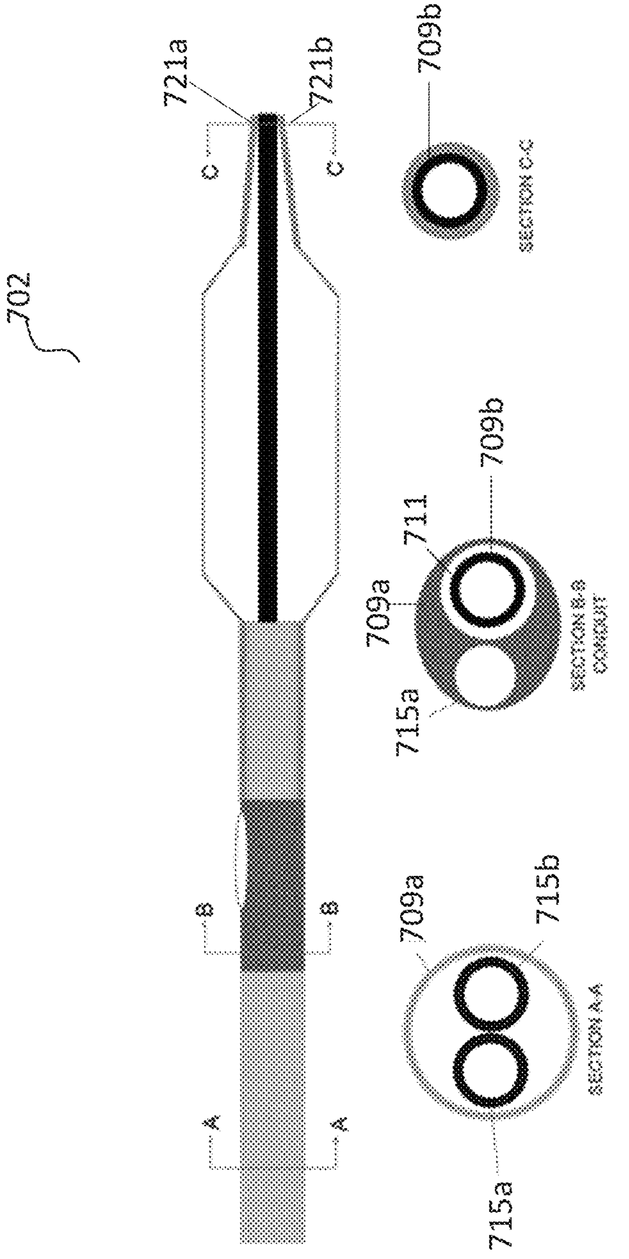
FIG. 5 illustrates an exemplary variation of different cross-sections of the elongate body.

FIG. 5 illustrates a variation of an elongate body for use in the blood flow control devices described herein with cross-sectional views at different portions of the elongate body. In particular, FIG. 5 illustrates three cross-sections—section A-A, section B-B, section C-C of the elongate body. In this variation, the elongate body comprises one or more bodies forming lumens. In some variations, the one or more bodies may be pressure sensing columns for measuring physiologic conditions of the patient. For example, the one or more bodies forming the lumens may be fluid columns that may enable measurement of blood pressure. More specifically, the one or more bodies forming the lumens may permit blood to be transmitted through the lumens. The lumens may be connected to the controller (e.g., blood device controller and/or system controller) to measure and/or monitor the blood pressure of the patient. For example, a first body forming a first lumen may have an opening on a distal end of the elongate body. This lumen may be coupled to a controller and/or other equipment to measure the blood pressure distal to the expandable member. A second body forming a second lumen may have an opening proximal to the expandable member. This lumen may be coupled to a controller and/or other equipment to measure the blood pressure proximal to the expandable member. In some variations, the bodies may be made from polymers and may be formed from an extrusion process.

As seen in FIG. 5, the blood flow control device may comprise an elongate body 702 comprising two bodies 715*a* and 715*b* positioned within an outer layer 709*a* (e.g., structurally and/or functionally similar to outer layer 609*a* in FIG. 4). Section A-A of the elongate body depicts the two bodies 715*a* and 715*b*.

An annular space 711 (e.g., structurally and/or functionally similar to annular space 611 in FIG. 4) may be formed between the outer layer 709*a* and the inner layer 709*b* (e.g., structurally and/or functionally similar to inner layer 609*b* in FIG. 4). In some variations, at section A-A the outer layer 709*a* may be thinner than at section B-B. Section B-B shows the annular space formed between the outer layer 709*a* and the inner layer 709*b*. The body 715*a* (e.g., body 715*a* forming a lumen) may be formed or positioned in the outer layer 709*a*.

Section C-C shows that the bodies 715*a* and 715*b* may be positioned alongside the inner layer 709*b*. For example, the bodies 715*a* and 715*b* may be formed alongside the inner layer 709*b* through an extrusion process (e.g., polymer extrusion). In some variations, the bodies 715*a* and 715*b* may be radially reinforced. The bodies 715*a* and 715*b* may be formed or positioned in the outer layer 709*a*, which may optionally be radially reinforced. In some variations, the body or bodies in which the lumens 715*a* and 715*b* are formed may be composed of high durometer material to achieve a balance between sufficient flexibility and kink resistance during navigation and to withstand rapid inflation and deflation of the expandable member. In some variations, the durometer of the material forming 715*a* and 715*b* may be between about 70 D and about 90 D, between about 72 D and about 85 D, between about 75 D and 80 D, or between about 72 D and about 75 D (including all values and sub-ranges therein). In some variations, the durometer may be about 70 D or about 72 D.

Referring back to FIG. 3, under certain physiological conditions (e.g., full occlusion, larger blood vessels, etc.), portions of the elongate body 502 may be susceptible to deformation. For example, the elongate body 502 and/or the expandable member 510 may be susceptible to buckling, collapsing, kinking, and/or migration of the expandable member 510. This may be hazardous for the patient and may cause damage to the blood flow control device itself. In some variations, such deformation may be potentially mitigated through use of a guidewire during navigation of the elongate body, which may provide additional support for the elongate body 502. In other variations, the blood flow control device described herein may utilize a stylet during insertion and/or navigation. In some variations, an introducer sheath may be used to introduce the elongate body 502 into the blood vessel. The introducer sheath may include a valve (e.g., a hemostatic valve) to minimize blood loss and stagnation of blood during the medical procedure. In some variations, the stylet may be introduced through a side hole 505 at the distal end of the elongate body 502 and may assist in advancing the atraumatic tip 503 through the valve of the introducer sheath. In some variations, when the introducer sheath is utilized, the stylet may assist in straightening the atraumatic tip 503. In some variations, a stylet may be inserted through the elongate body (e.g., through a side hole 505 at the distal end of the elongate body 502 (e.g., near the tip of the elongate body 502)) to assist in straightening the atraumatic tip 503 regardless of whether an introducer sheath is utilized. Use of a stylet during advancement may balance pushability and flexibility for navigation, while mitigating kinking of the elongate body 502 and/or the expandable member 510. In some variations, the stylet may be inserted during the endovascular procedure to assist in maintaining occlusion of the blood vessel. In some variations, the expandable member and distal portion of the elongate body may be housed within a peel-away sheath for insertion.

Expandable Member

Referring back to FIG. 1A, the expandable member 110 may be disposed on, coupled to, integrated with, attached to, and/or affixed to the shaft of the elongate body 102 and a size of the expandable member may be controllable by a controller or a user. For example, the expandable member may be configured to expand and contract and/or inflate and deflate such that the size (e.g., volume) of the expandable member may change during use of the blood flow control system. In some variations, the expandable member may be an inflatable/deflatable balloon, while in other variations the expandable member may comprise a shape memory material. In yet other variations, the expandable member may be connected to a mechanical linkage (e.g., wires, etc.) to change the size of the expandable member. The expandable member 110 may comprise any suitable elastomeric material (e.g., polyurethane, silicone, etc.). Additionally or alternatively, the expandable member 110 may comprise polyester, nylon, etc.

During use, blood flow may be regulated or otherwise controlled by changing a size of the expandable member 110, thereby altering the area of the blood vessel that is occluded by the expandable member 110. Fluid and/or compressed gas may be delivered through one or more lumens in the elongate body 102 in order to control and/or adjust the size (e.g., volume) of the expandable member 110. Thus, in some variations, the expandable member 110 may be strategically placed within the blood vessel (e.g., aorta retrograde from the femoral artery) of a patient and the size of the expandable member 110 may control blood flow through the blood vessel of the patient such that blood flow distal to expandable member 110 may be impeded to augment blood pressure proximal to expandable member 110. The outer surface of the expandable member 110 may be configured to contact or otherwise interface with the wall(s) of the patient's blood vessel (e.g., at complete occlusion). In some variations, the elongate body may be inserted through a radial or brachial artery so that the elongate body is inserted antegrade down the aorta. In such variations, the proximal sensor (e.g., proximal sensor 411*b* in FIG. 2) may be distal or downstream from the heart and the distal sensor (e.g., distal sensor 411*a* in FIG. 2) may be proximal or upstream to the heart. In such variations, the expandable member 110 may expand to impede blood flow to the distal sensor (e.g., distal sensor 411*a* in FIG. 2).

The expandable member 110 may have any suitable shape when inflated. In some variations, the expandable member 110 may have an oval cross-sectional shape along a longitudinal axis when inflated. This may optimize anchoring of the expandable member 110 with increased surface contact between the blood vessel wall and the expandable member 110 in comparison to a circular cross-sectional shape when inflated. In other variations, the expandable member 110 may have a spherical shape when inflated (e.g., may have a circular cross-sectional shape).

Although FIG. 1A illustrates one expandable member 110 configured to regulate blood flow through the aorta of a patient, it should be readily understood that the blood flow control device 104 may include any number of suitable expandable members 110. For instance, the blood flow control device 104 may include two expandable members 110 disposed on, coupled to, integrated with, attached to, and/or affixed to the elongate body 102 in series. Similarly, the blood flow control device may include three expandable members disposed on, coupled to, integrated with, attached to, and/or affixed to the elongate body 102 in series and spaced at equal distance from each other In some variations, the expandable member 110 may comprise a plurality of balloons (e.g., two, three, four, or more) positioned in series along the length of the elongate body 102 or disposed within each other. In variations comprising a plurality of balloons, the balloons may be configured to expand and contract individually or separately.

Sensor(s)

The blood flow control systems described herein may comprise one or more sensors (e.g., two, three, four, five, or more). In some variations, the blood flow control device may itself comprise one or more sensors, while in other variations, one or more sensors may be integrated into the system separately from the blood flow control device. In some variations, the blood flow control device may comprise one or more sensors, and one or more sensors may be integrated into the system separately from the blood flow control device. For example, one or more sensors (e.g., a distal sensor, a proximal sensor) may be integrated with and/or disposed on the elongate body 102 of the blood flow control device.

Figure 6:
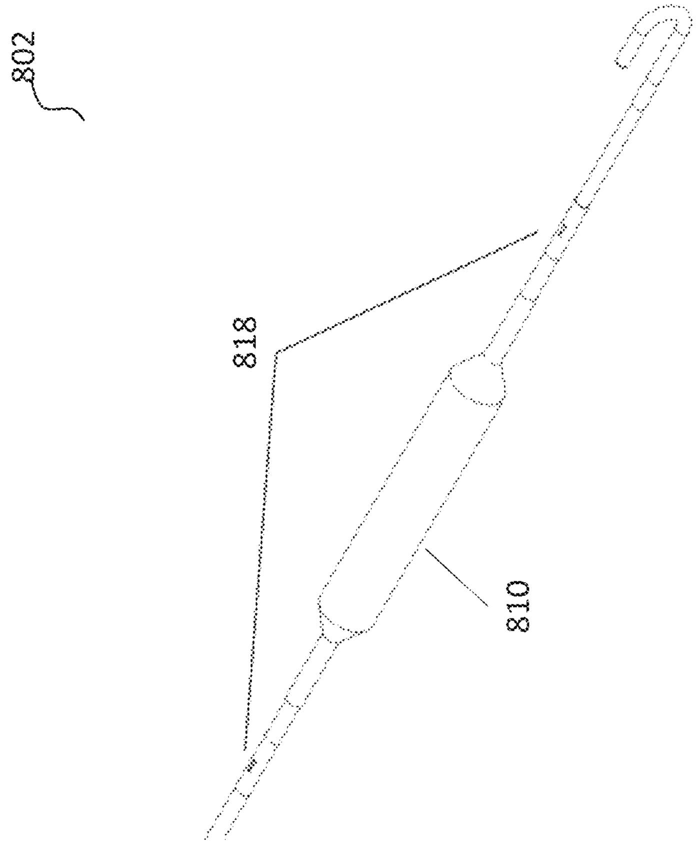
FIG. 6 is an exemplary variation of an elongate body with a proximal sensor and a distal sensor.

FIG. 6 is an exemplary variation of an elongate body 802 (e.g., structurally and/or functionally similar to elongate body 102 in FIG. 1A) comprising a plurality of sensors. As seen in FIG. 6, a proximal sensor and a distal sensor (collectively sensors 818) may be integrated with and/or disposed on the elongate body 102. In some variations, the distal sensor may be disposed and/or integrated proximal to the expandable member 810, while the proximal sensor may be disposed and/or integrated distal to the expandable member 810.

Figure 7:
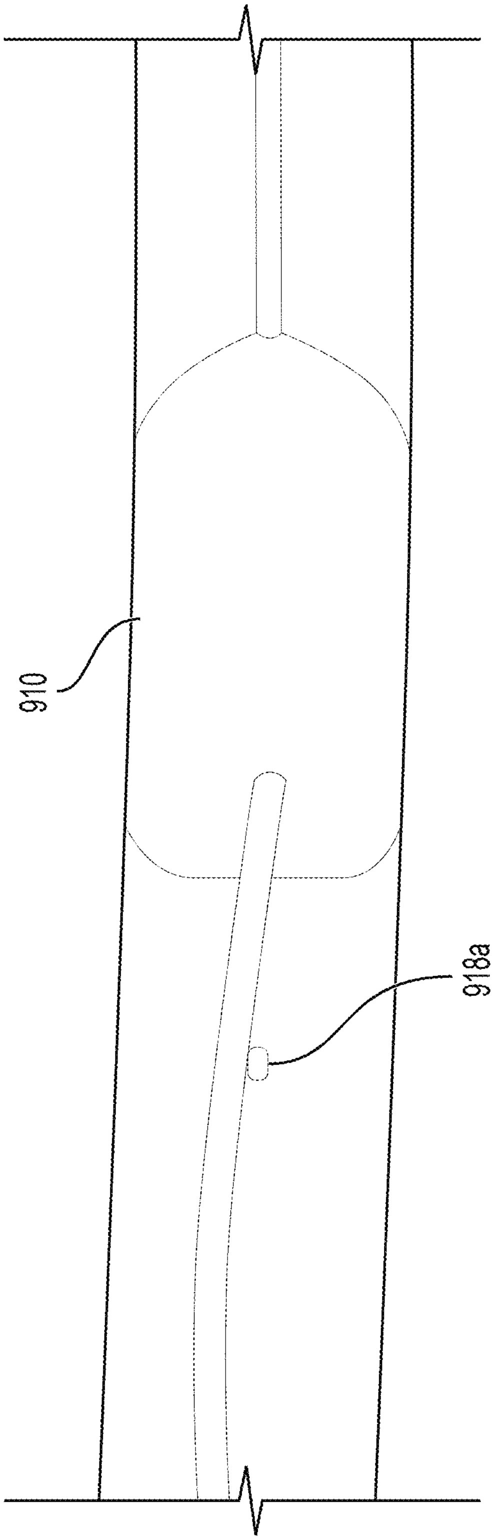
FIG. 7 illustrates an exemplary variation of placement of a distal sensor relative to an expandable member on an elongate body of a blood flow control device.

In some variations, the distal sensor located on the proximal side of the expandable member 810 may be placed at a distance from the expandable member 810 such that the physiologic data collected from the distal sensor may not be disrupted by the blood flow downstream of the expandable member 810. In some variations, the distal sensor may be placed at a distance between about 30 mm and about 10 mm, between about 25 mm and about 15 mm, between about 22 mm and about 18 mm from the expandable member 810. For instance, the distal sensor may be placed approximately 20 mm from the expandable member 810. FIG. 7 illustrates a distal sensor 918*a* placed at 20 mm from the expandable member 910. In some variations, the proximal sensor located on the distal side of the expandable member may be placed between about 30 mm and about 10 mm, between about 25 mm and about 15 mm, or between about 22 mm and about 18 mm from the expandable member 810. For instance, the proximal sensor may be placed approximately 20 mm from the expandable member 810. As discussed above, in some variations, sensors on the elongate body may be situated at a specific distance from the ends of the expandable member so as to acquire the physiologic data upstream and downstream of the expandable member. In some variations, the one or more sensors may be microelectrochemical system (MEMS) sensors. In some variations, the one or more sensors may be piezoelectric sensors.

In some variations, one or more sensors may be disposed on tubing that may be coupled to open ports in the elongate body 102. For example, one or more sensors (e.g., a proximal sensor, a distal sensor) may be connected via a saline-filled tube that may connect to open ports that are proximal or distal to the expandable member 110. Put differently, instead of being disposed on the elongate body 102, these sensors may be coupled to saline-filled tubes that are fluidly coupled to the elongate body 102 (e.g., at ports proximal or distal to the expandable member) via the saline-filled tube. In such variations, the pressure along the saline-filled tube may be measured by the proximal sensor and the distal sensor. In yet other alternative variations, the one or more sensors may be integrated into and/or disposed on the blood flow control system 100 via a combination of the saline-filled tube and via one or more wires.

Referring back to FIG. 1A, the elongate body 102 may comprise more than one sensor. In some variations, the one or more sensors may be positioned along the elongate body 102 surface along the same longitudinal line. Alternatively, the one or more sensors may be positioned along the elongate body 102 along different longitudinal lines. For example, a first sensor may be positioned along a first longitudinal line along the elongate body 102 and a second sensor may be positioned along a second longitudinal line along the elongate body 102. The first longitudinal line and the second longitudinal line may be parallel to each other. In other words, the first sensor may be positioned along a first line along the elongate body 102 and the second sensor may be positioned along a second line parallel to the first line along the elongate body 102.

As described above, the elongate body may comprise any suitable number of sensors (e.g., two, three, four, five, or more) and the sensors may be positioned in any suitable location for measuring a physiologic condition of the patient and/or a characteristic of the expandable member. For example, the blood flow control device may comprise a first, distal sensor, and a second, proximal sensor. The distal sensor, the position of which is indicated by reference numeral 110*b*, may be disposed between the distal tip of the elongate body 102 and the expandable member 110. A proximal sensor, the position of which is indicated by reference numeral 110*a*, may be disposed between the base of the elongate body 102 (where the elongate body 102 couples to device controller 112) and the expandable member 110. Each of the distal sensor and the proximal sensor may measure patient physiologic information, such as physiologic information indicative of blood pressure or blood flow through a blood vessel (e.g., the aorta), to determine the patient's underlying physiology. For example, the distal sensor and the proximal sensor may measure a local blood pressure of the patient at or around the position of the respective sensor. For example, the distal sensor may measure a blood pressure of the patient within the blood vessel at a region surrounding 110*b* and the proximal sensor may measure a blood pressure of the patient within the blood vessel at a region surrounding 110*a*. The data from the distal sensor may be used to measure the distal systolic pressure and the distal diastolic pressure of the patient. For instance, distal systolic pressure and distal diastolic pressure may be inferred from a waveform of the blood pressure. Distal systolic pressure may be measured by analyzing peaks of the waveform for a given time duration. Distal diastolic pressure may be measured by analyzing valleys of the waveform for the given time duration. Distal mean arterial pressure may be measured from the distal systolic pressure and the distal diastolic pressure. In a similar manner, the data from the proximal sensor may be used to measure the proximal systolic pressure and the proximal diastolic pressure of the patient. For instance, proximal systolic pressure and proximal diastolic pressure may be inferred from a waveform of the blood pressure. Proximal systolic pressure may be measured by analyzing peaks of the waveform for a given time duration. Proximal diastolic pressure may be measured by analyzing valleys of the waveform for the given time duration. Proximal mean arterial pressure may be measured from the proximal systolic pressure and the proximal diastolic pressure.

Although the proximal sensor and the distal sensor may measure a blood pressure of the patient, in some variations, the blood pressure may be used to calculate one or more of heart rate, respiratory rate, blood flow rate, cardiac output of the patient, and/or the like.

Note that the terms "proximal" and "distal," as used herein in relation to sensor(s) and/or particular localized blood pressure readings, refer to blood flow directionality from the heart. That is, "proximal" is closer to the heart while "distal" is further from the heart. This is not to be confused with the reversed usage of the terms when described from the perspective of a medical device such as a catheter, where the "distal end" of the medical device would commonly be understood as the end with the expandable element 110 furthest from the system controller 106 and the "proximal end" would be understood as the end closer to the operator.

In some variations, the blood flow control device may further comprise an expandable member sensor (not shown in FIGS. 1A and 1*n* FIG. 1B). In some variations, the expandable member sensor may be coupled to, integrated with and/or disposed on the expandable member 110 or on the elongate body 102 within the expandable member 110. In some variations, the expandable member sensor may be coupled to, integrated with and/or disposed on a controller (e.g., the device controller 112, system controller 106) and may be fluidly coupled to the expandable member.

The expandable member sensor may detect a characteristic of the expandable member, such as, for example, a pressure of fluid and/or compressed gas inside the expandable member 110. In some variations, the pressure and/or changes to the pressure of fluid and/or compressed gas inside the expandable member 110 may be analyzed to detect one or more errors. For instance, the expandable member sensor may detect when the pressure of the fluid and/or compressed gas inside the expandable member 110 is too high. In some variations, the expandable member sensor may detect an unexpected pressure change inside the expandable member 110. This may be indicative of a rupture in the expandable member 110. In some variations, if the trend of the change in pressure inside the expandable member 110 is dissimilar with the expected change based on the trend in proximal pressure or distal pressure, the expandable member sensor may detect this difference from expected change. In some variations, the expandable member sensor may detect spikes in the pressure inside the expandable member 110 during changes to the movement of the pump 108 in order to detect if the movement of the pump 108 corresponds to the expected pressure inside the expandable member 110. In some variations, the expandable member sensor may detect the amount (e.g., a volume) of fluid and/or compressed gas that has been added to or removed from the expandable member 110.

The blood flow control device may further optionally comprise a flow sensor (not shown in FIG. 1A and FIG. 1B). The flow sensor may be integrated with and/or disposed on the expandable member 110 and may measure the amount and/or rate of blood flowing past the expandable member 110. In variations in which a blood flow sensor is not included, the amount and/or rate of blood flowing past the expandable member 110 may be determined from measurements obtained from other sensors, such as, for example, one or more of the proximal sensor, the distal sensor, and the expandable member sensor.

In some variations, the blood flow control device may further comprise a barometer (not shown in FIG. 1A and FIG. 1B). The barometer may be integrated with and/or disposed within a housing of the device controller 112 and/or may be disposed within the elongate body 102 and may be communicatively coupled to the device controller 112. In some variations, the barometer may be electronically coupled to and/or may be integrated with one or more printed circuit board assemblies, for example, printed circuit board assembly 1247 in FIG. 8. In some variations, the barometer may be integrated with and/or disposed within a housing of the system controller 106 and may be communicatively coupled thereto. The system may also comprise a plurality of barometers, such as, for example, device controller barometer and a system controller barometer. The one or more barometers may measure ambient pressure at the location of the patient. For instance, the proximal sensor and the distal sensor may measure the absolute blood pressure. However, the barometer may measure the ambient pressure at the location of the patient. Accordingly, the blood pressure reported by the blood flow control system 100 may be blood pressure that is relative to the ambient pressure at the location of the patient (e.g., taking into consideration changes to ambient pressure as the patient is transported). Additionally or alternatively, the blood flow control device may include a gauge sensor to measure the relative pressure of the blood relative to the ambient air.

In some variations, an expandable member sensor may measure the expandable member pressure. For example, when the actuator translates the plunger to inflate or deflate the expandable member, spikes in the expandable member pressure may be detected. Conversely, an absence of spikes in the expandable member pressure may be used to infer that the actuator may be unable to inflate or deflate the expandable member.

Monitoring pressure inside the expandable member (e.g., using an expandable member sensor) and blood pressure of the subject may provide information on the amount of inflation and deflation of the expandable member. The expandable member pressure may be received in the form of waveforms. The controller may identify spikes (e.g., instantaneous ascent and/or instantaneous descent) in the expandable member pressure waveforms. Differentiating between the spikes in the expandable member pressure may help identify the amount of inflation and deflation of the expandable member. For instance, differentiating between the spikes may help identify whether the plunger has translated to either inject fluid and/or withdraw fluid from the expandable member.

Figure 22A:
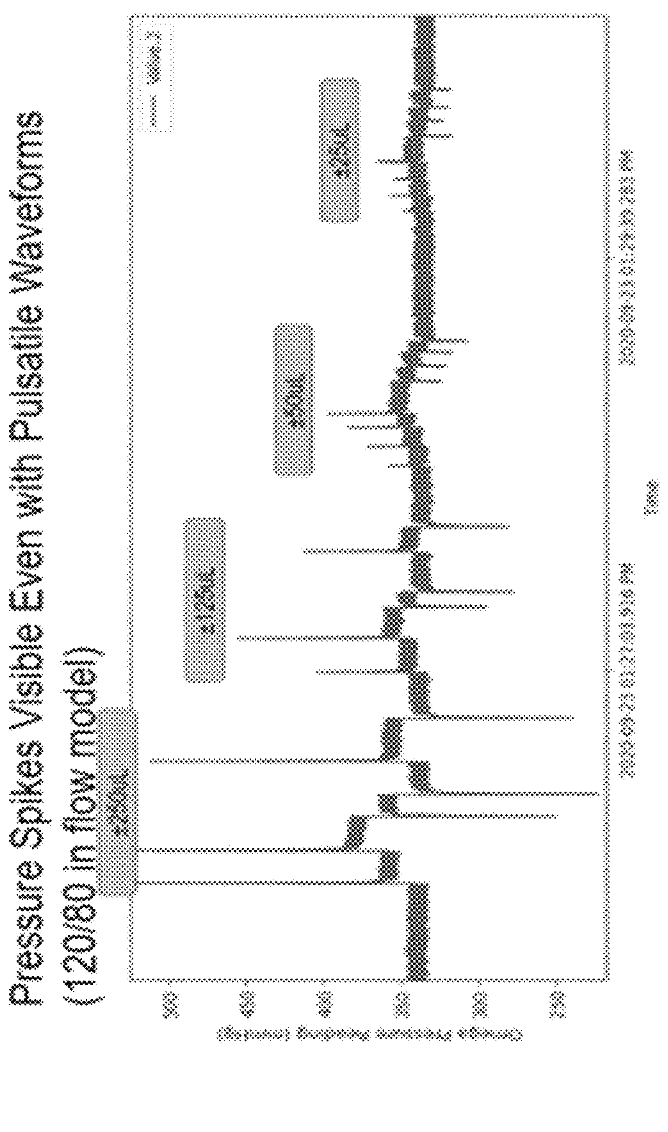
FIG. 22A illustrates a graph showing spikes in pressure for fluid movements of 100-200 μL to and from the expandable member.
Figure 22B:
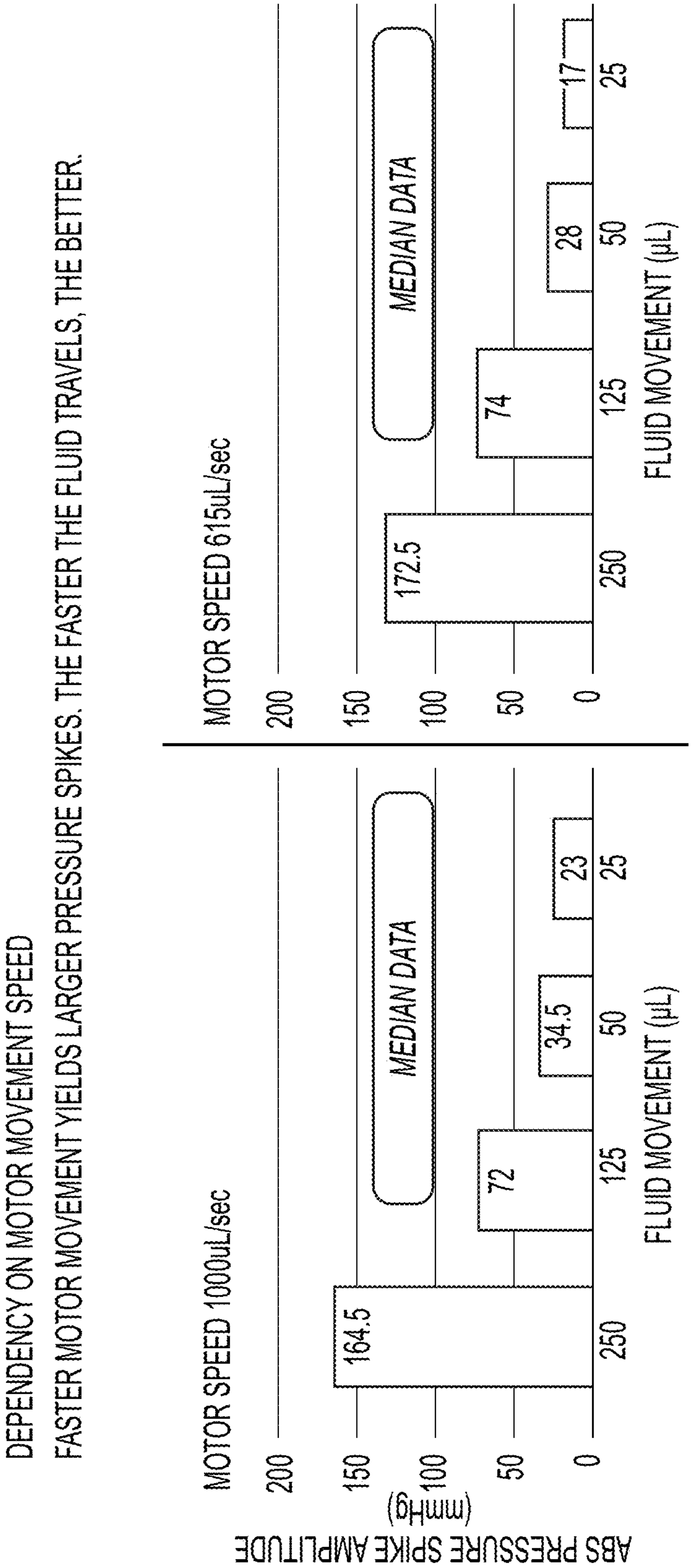
FIG. 22B illustrates expandable member pressure spikes for various actuation movements.
Figure 22C:
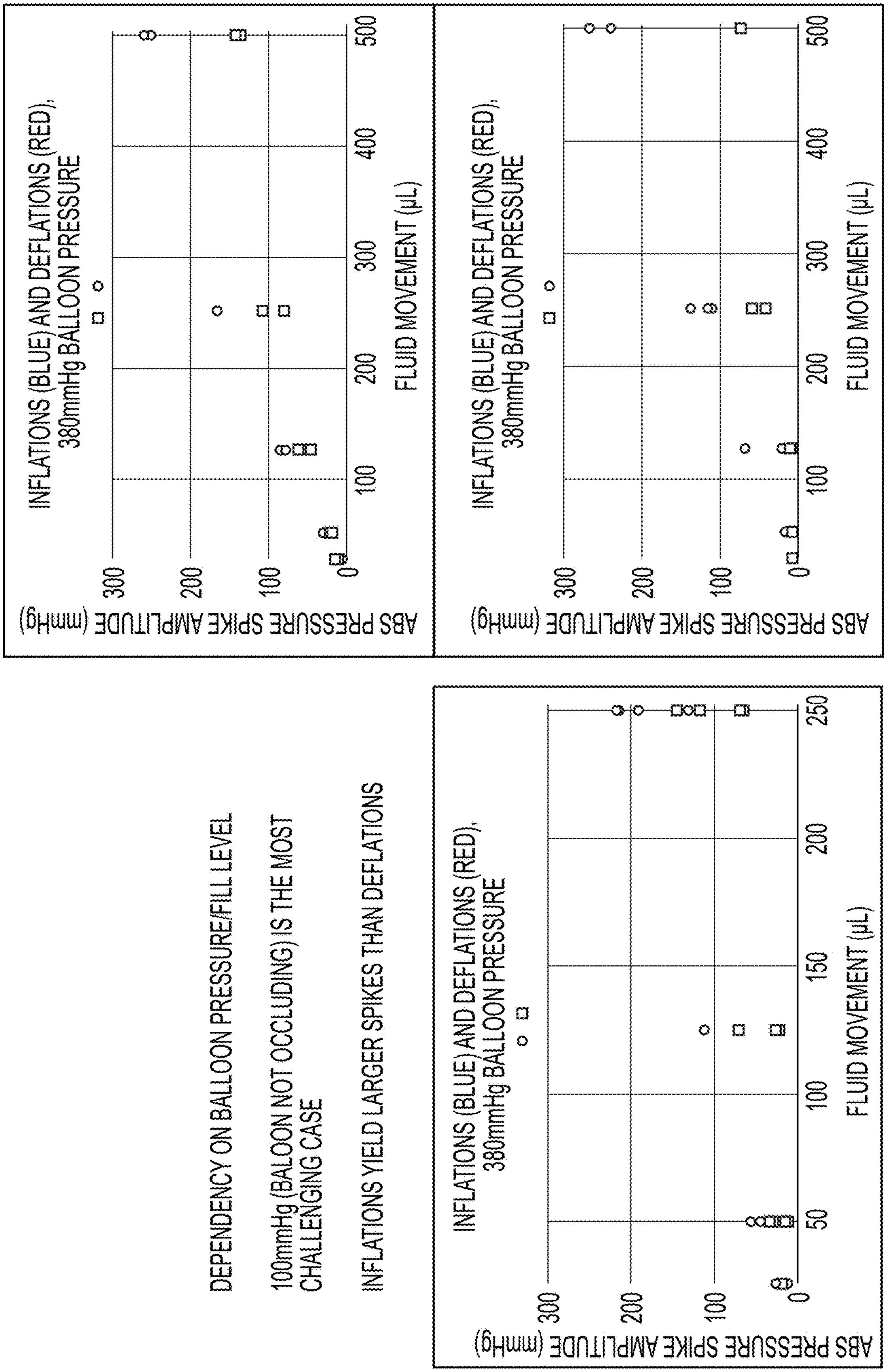
FIG. 22C illustrates expandable member pressure spikes for various fluid movements.

Referring to FIG. 22A, shown there is a plot depicting expandable membrane pressure waveforms. The plot in FIG. 22A shows that movements of 100-200 μL of fluid may be distinguishable from the baseline pressure waveforms in the expandable membrane pressure caused by the blood pressure exerting an effect on the external surface of the expandable membrane. When the plunger moves forward (injecting fluid) the pressure in the expandable member increases rapidly (e.g., instantaneously ascends) and then drops rapidly (e.g., instantaneously descends) as the fluid moves to the expandable member. Therefore, the controller may receive a spike in the expandable member pressure. Similarly, when the plunger is moved backwards (withdrawing fluid) the pressure in the expandable member decreases rapidly and then increases back to the new equilibrium pressure. The controller may receive sensor data (e.g., expandable member pressure data) at a faster rate (e.g., at least two times faster, at least 2.5 times fast, at least 3 times faster, or more) than the rate at which the expandable member pressure changes, and may then calculate the rate of change in the expandable member pressure. When the rate of change of expandable member pressure exceeds a threshold and/or the amplitude of the spike in the expandable member pressure waveforms exceeds a threshold, this may indicate that the plunger is moving. FIG. 22B indicates that faster actuation movements (e.g., faster movements of the motor coupled to an actuator such as circular gear) may yield larger expandable member pressure spikes. FIG. 22C indicates that an expandable member at near occlusion may be sensitive to fluid movements resulting in larger expandable member pressure spikes that are dependent both on the general range of pressure and volume within the expandable member as well as the specific volume added or removed from the expandable member by the controller.

Device Controller

The blood flow control device 104 may comprise a device controller 112, which may be coupled to a base of the elongate body 102. The device controller 112 may comprise a housing that may be coupled to a proximal end the elongate body and may contain electronic components (e.g., a processor (one or more printed circuit board assemblies (PCBA)), memory, a power source, and the like). In some variations, and as described in more detail below, the device controller 112 may further comprise a splitter configured to separate fluid and electrical pathways through the device controller housing. The device controller 112 may be communicatively coupled to one or more sensors, such as, for example, the proximal sensor, the distal sensor, and/or the expandable member sensor. For example, the device controller 112 may be electronically coupled to the proximal sensor, the distal sensor and/or the expandable member sensor via, for example, a wired connection.

In some variations, the device controller 112 may comprise a housing. The housing may be coupled to the elongate body 102 and may contain a number of electronic components, such as, for example, a biasing circuit, an optional amplifier, a filter, and an Analog-to-Digital Conversion (ADC) circuit. The ADC circuit may output the readings obtained from the sensors (e.g., the proximal sensor and the distal sensor), thereby indicating a physiologic condition of the patient. For example, in some variations, the proximal sensor and the distal sensor may each include three connection wires, a power wire and two output wires. The output wires may be connected to the biasing circuit and the power wire. The biasing circuit may provide power to the power wire and appropriate resistance to the two output wires. The two output wires may be coupled to the amplifier which may amplify the differential voltage created across the two output wires. The amplifier may be coupled to the filter which may reduce high frequency and/or low frequency noise from the output of the amplifier. The output of the filter may be coupled to the Analog-to-Digital Conversion (ADC). The output of the ADC may be at a variety of rates and sample sizes indicating a physiologic condition of the patient. The device controller 112 may include any of the components and/or features described with respect to the system controller 106 and/or pump controller described herein.

In some variations, and as discussed in more detail herein with respect to the system controller, the device controller 112 (e.g., the housing) may include a user interface. In some variations, the device controller 112 may be used primarily as a user interface (e.g., it may not provide a controlling capability for the blood flow control device). In any variation described herein, the user interface may be configured to display physiologic conditions of the patient during the endovascular procedure and/or target physiologic conditions for the patient. In some variations, the user interface may comprise an input device (e.g., touch screen) and/or an output device (e.g., display device), and may be configured to receive input data from one or more of the blood flow control device 104, communications device, system controller 106, pump 108, and the sensor(s). For example, the user interface may include widgets, capacitive buttons, resistive buttons, capacitive panels, resistive panels, a combination thereof, and/or the like (e.g., collectively referred to as "touchscreen buttons"). In some variations, during a manual mode of operation of the system controller (e.g., when the pump is coupled to the system controller and the system controller is in the manual mode), a user may press and/or touch the touchscreen buttons on the user interface of the device controller to control the pump. The touch screen may be configured to detect contact and movement on the touch surface. Pressing the touchscreen buttons may control the movement of the actuator (e.g., circular gear) positioned within the system controller. This in turn may cause the actuation element (e.g., linear gear) of the pump, which engages with the actuator, to move. Accordingly, by pressing the touchscreen buttons on the user interface of the device controller, the user may be able to move the pump, thereby changing a volume of the expandable member. While described above with respect to the touchscreen buttons, the device controller may additionally and/or alternatively include physical buttons (e.g., buttons, pins, lever, etc.) on a housing of the device controller to operate in the manual mode of operation.

In some variations, a user may input a target value, target range, expected value, expected range, threshold value, threshold range and/or the like for various sensor data via the user interface. In some variations, the user interface may display to the user blood flow state, graphs of one or more pressure waveforms, proximal pressure, distal pressure, expandable member volume, errors, etc. to the user as also explained in more detail herein with respect to the system controller. As discussed above, the device controller may be configured to receive user input and/or display output on the user interface. In some variations, the device controller may be configured to process sensor or other data (e.g., data received from a user interface). Accordingly, the electronics housed within the device controller housing may receive, send, and/or process sensor or other data. The device controller may comprise any of the components (e.g., electronic components) and may perform any of the functions of the system controller, as described in more detail herein with respect to the system controller.

While described above with respect to the device controller, it should be appreciated that in some variations in which a device controller and a system controller are used, or only a system controller is used, a user may utilize the user interface of the system controller for any of the features described above with respect to the device controller, such as, for example, to adjust the volume of the expandable member (e.g., via movement of the actuator and thus the pump).

Figure 8:
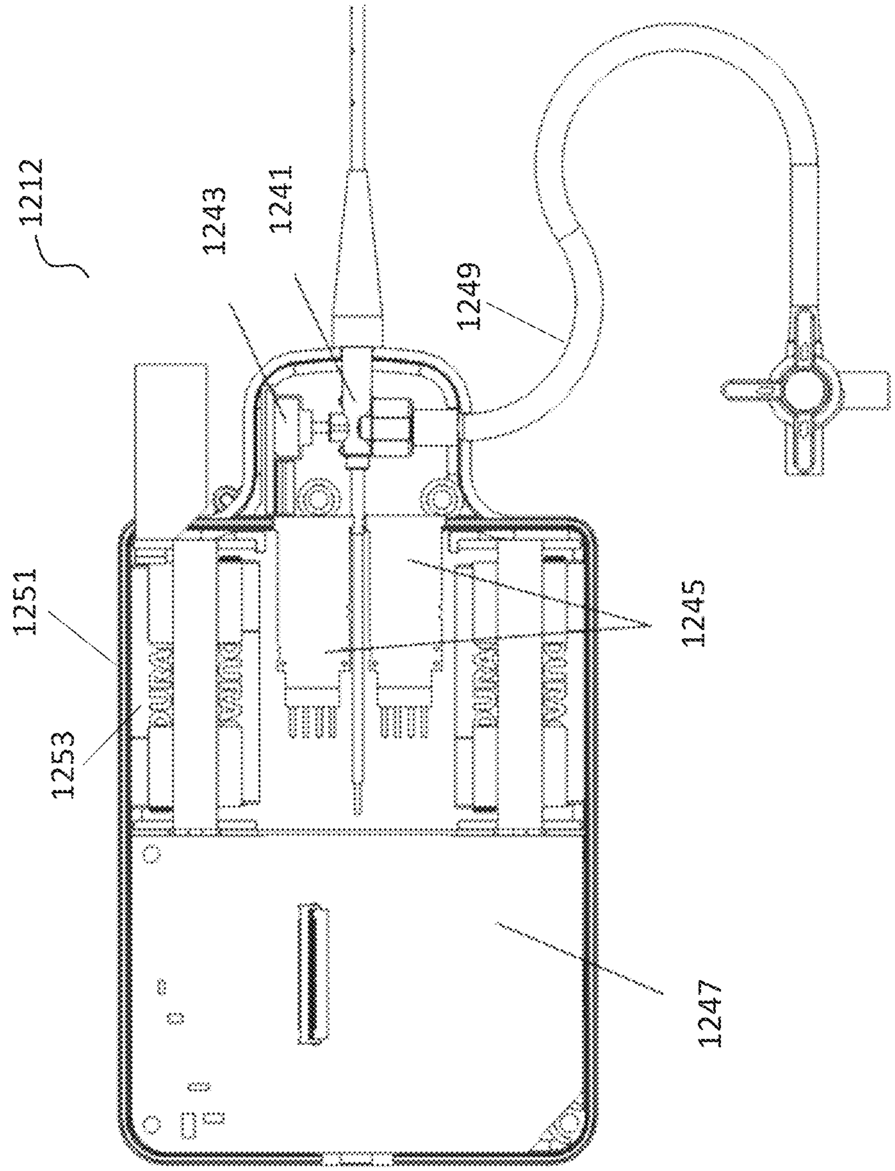
FIG. 8 illustrates a cutaway view of an exemplary variation of a device controller.

Turning now to FIG. 8, shown there is a bottom cutaway view of an exemplary variation of a device controller 1212 (e.g., structurally and/or functionally similar to the device controller 112 in FIG. 1A and FIG. 1B) comprising a splitter configured to provide separate electrical and fluid pathways. For example, in some variations, the device controller 1212 may include a housing 1251, one or more printed circuit board assemblies 1245 and 1247, a power supply 1253, and a splitter 1241. The splitter 1241 may split the fluid path and the electrical path thereby enabling a separate fluid path and a separate electrical path. For example, the fluid transfer lumen (e.g., the lumen formed between the core and the inner layer in FIG. 4) may be fluidly coupled to the sensor 1243 and a fluid extension line 1249. The printed circuit board assembly (PCBA) 1245 may be electrically coupled with the main PCBA 1247. In some variations the sensor PCBA 1245 and the main PCBA 1247 may be consolidated into a single PCBA. In this manner the elongate member with the lumen and sensor wires may be integrated into the device controller 1212 via the splitter 1241. In some variations, the printed circuit board assembly may include the wires for connecting all electronic components of the device controller 1212, including any sensors contained within or associated with the device controller 112.

In variations comprising both a device controller and a system controller, the device controller and the system controller may be coupled in a number of ways. For example, the device controller may be operably coupled to the system controller. For instance, the device controller may be communicably coupled to the system controller such that data (e.g., sensor data, user inputted data, commands, etc.) may be transferred between the two controllers. For example, the two controllers may be operably coupled via a wired and/or a wireless connection, as described in more detail herein with respect to the system controller. Additionally or alternatively, the housing of the device controller may be releasably coupled to a housing of the system controller (as further described in FIGS. 17A-17C and FIG. 18). For example, the device controller may be mechanically coupled to the system controller in any suitable manner. More specifically, the device controller may be mechanically coupled to the system controller via a coupling and/or alignment mechanism, such as, for example, a fastener, a latch, a mount, a joint, one or more magnets, a friction fit, a combination thereof, or the like. In some variations, the housing of the device controller may be coupled to the housing of the system controller via a plurality of coupling and/or alignment mechanisms (e.g., 2, 3, 4, 5, or more). For example, the device controller may be mechanically coupled to the system controller via one or more magnets and via one or more fasteners, or via two or more sets of fasteners. Additionally or alternatively, in some variations, the device controller may be electrically coupled to the system controller, such as, for example, via an electric connector, a cable, or the like.

Pump

The blood flow control systems described herein may include any type of pump suitable for delivering fluid to a blood flow control device to, for example, adjust the size (e.g., volume) of an expandable member of the device. Referring to FIG. 1, the blood flow control systems may comprise a pump 108, which may be operably (e.g., fluidly) coupled to the expandable member 110 to facilitate adjusting a size thereof. The pump 108 may be contained within (e.g., within an open or closed cavity or chamber) or otherwise carried by or coupled to the housing of the device controller 112 or the system controller 106, and may be communicably coupled to one or both of the device controller 112 and the system controller 106. It should be appreciated that in some variations the system controller may control the blood flow control device and the pump, and the device controller may serve as a user interface to, e.g., present data.

As discussed above, the pump 108 may be operated manually (e.g., actuated by a user by hand, without use of the device or system controllers), or by using the device controller 112 and/or the system controller 106 (e.g., in an automatic mode of operation and/or in a manual mode of operation). As discussed above, in some variations, the pump 108 may be operated automatically or autonomously using the system controller 106 (e.g., automatic mode of operation) and/or may be operated via a user interface (e.g., buttons) on the system controller 106 (e.g., manual mode of operation).

In some variations, at the beginning of the endovascular procedure, the pump 108 may be detached from or otherwise decoupled from the system controller 106, and may be operated manually to establish a position and initial inflation level or volume for the expandable member. Once this has been established, the pump may be releasably coupled to the system controller 106 (e.g., a housing of the system controller 106) so as to control the volume (e.g., inflation and deflation) of the expandable member automatically using the device controller 112 and/or system controller 106. Utilizing a single fluid reservoir (e.g., pump 108) for both manual and automatic actuation may advantageously reduce or prevent the introduction of air into the blood flow control system. Additionally, it may further streamline endovascular procedures.

The pump 108 may comprise or otherwise be coupled to an elongate member comprising a lumen (e.g., tubing), which may in turn be coupled to a lumen of the elongate body of the blood flow control device (e.g., a fluid transfer lumen). In this manner, the pump 108 may be in fluid communication with the expandable member 110.

In some variations, a set of one or more valves may be utilized to control the flow of a fluid and/or compressed gas, such as carbon dioxide. In some variations, the pump may be fluidly coupled to a valve (e.g., a stopcock valve) which may regulate the flow of fluid and/or compressed gas to the expandable member 110. In some variations, the expandable element may additionally or alternatively include a shape-change material (e.g., nitinol) configured to controllably expand and contract in response to applied electrical current, voltage, temperature, or pressure, for example. Such variations may include a frame formed from the shape-change material that is attached to one or more membranes to form a "sail" that may controllably open and close according to selective shape change of the frame. Such membranes may be made from a polymeric material suitable for contact with the aorta, for example.

The size (e.g., volume) of the expandable member may be adjusted using the system and/or device controller and the pump. For example, the system and/or device controller may determine an amount of fluid and/or compressed gas that is to be injected into or removed from the expandable member so as to adjust the size of the expandable member and thereby affect blood flow. The system and/or device controller may control (e.g., move, modify or control a position thereof) an actuator, which may be releasably coupled to the pump (e.g., to an actuation element on the pump). The actuator may engage and move the actuation element, thereby moving a portion of the pump such that the pump may inject or remove the fluid and/or compressed gas from the expandable member based on instructions from the system and/or device controller. For example, in some variations, the pump may include a plunger positioned within a cylindrical body containing the fluid and/or compressed gas (e.g., a syringe pump). The syringe pump may inject or remove fluid and/or compressed gas from the expandable member. In some variations, the actuator may inject the fluid and/or compressed gas into the expandable member using the normal action of syringe. In some variations, the actuator may comprise a pinion or circular gear, which may engage a corresponding actuation element on the pump, which may comprise a rack or linear gear, as will be described in more detail herein.

Figure 9:
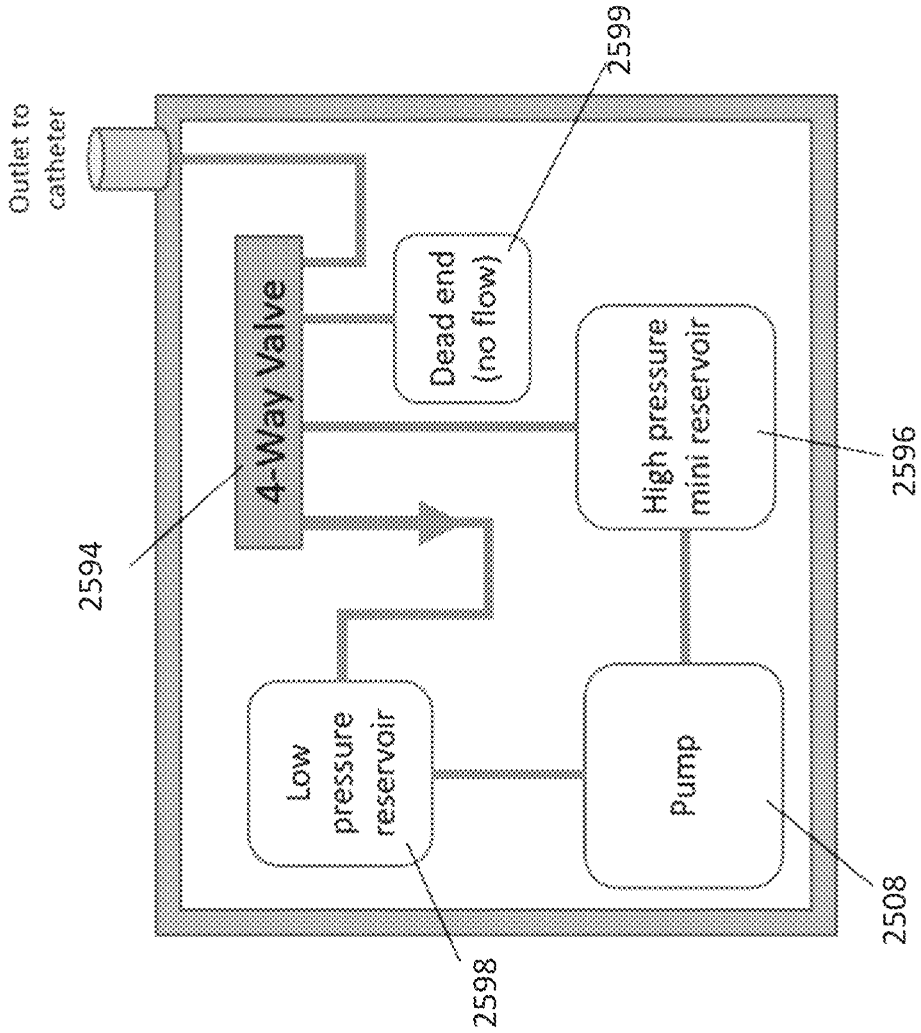
FIG. 9 illustrates an exemplary variation of a pump utilizing a four-way valve.

In some variations, removal of the fluid and/or compressed gas may be activated via a screw actuation. For example, the inflation may be accomplished by putting pressure on the end of the plunger so that it is inserted into the cylindrical body of the syringe, but, once pressure is released, a screw actuator may be engaged, and deflation may occur only by rotation of the screw mechanism, which may allow for greater precision in deflation. In some variations, the pump 108 may be a diaphragm, peristaltic, or other suitable pump. Referring to FIG. 9, FIG. 9 illustrates an exemplary variation of a pump 2508 utilizing a four-way valve 2594, which may assist in maintaining accuracy of the pump. The four-way valve 2594 may be connected to a high-pressure reservoir 2596 and a low-pressure reservoir 2598. The high-pressure reservoir 2596 may cause the pump 2508 to transmit fluid to an expandable member. The four-way valve 2594 may be opened for a precise amount of time allowing a controlled amount of fluid to be released to the expandable member. The low-pressure reservoir 2598 may relieve the fluid from the expandable member as needed. The final position of the four-way valve 2594 may be an "off position" 2599 allowing no flow to the expandable member. Alternately, the off position may be removed and a three-way valve or a combination of two-way valves could be used to achieve the same effect.

Although the above paragraph describes specific variations of the pump 108, it should be readily apparent that pump 108 may be any suitable pump operably and/or communicatively coupled to an actuator so as to inject and/or remove the fluid and/or compressed gas from the expandable member 110. In some variations, the pump 108 may be coupled to or otherwise used with one or more of a position sensor and/or a motion sensor, which may provide information on the position of a portion or component of the pump 108 (e.g., actuation element (linear gear), plunger generally, etc.) or other part of the blood flow control device (actuator (e.g., circular gear), actuation mechanism (e.g., motor)), and thus how much fluid has been delivered to the expandable member 110, as further described herein.

In some variations, the pump may comprise a motor (e.g., a stepper motor) and/or a controller arm. In these variations, the syringe may be operably coupled to the motor and/or the controller arm, and the motor and/or the controller arm may move a portion of the syringe (e.g., the plunger) thereby delivering or removing fluid or compressed gas from the expandable member. Additionally or alternatively to serving as an actuation mechanism for the pump 108, in some variations, the motor and/or the controller arm may provide additional means to further adjust the volume of the expandable member 110. For instance, one or more wires may be wound around the expandable member 110 and the motor and/or the controller arm may be configured to tighten or loosen the wires relative to a point on the elongate body 102 so as to further adjust the volume of the expandable member 110. That is, the tightening and loosening of the wires may further adjust the expansion and/or contraction of the expandable member 110.

Figure 10:
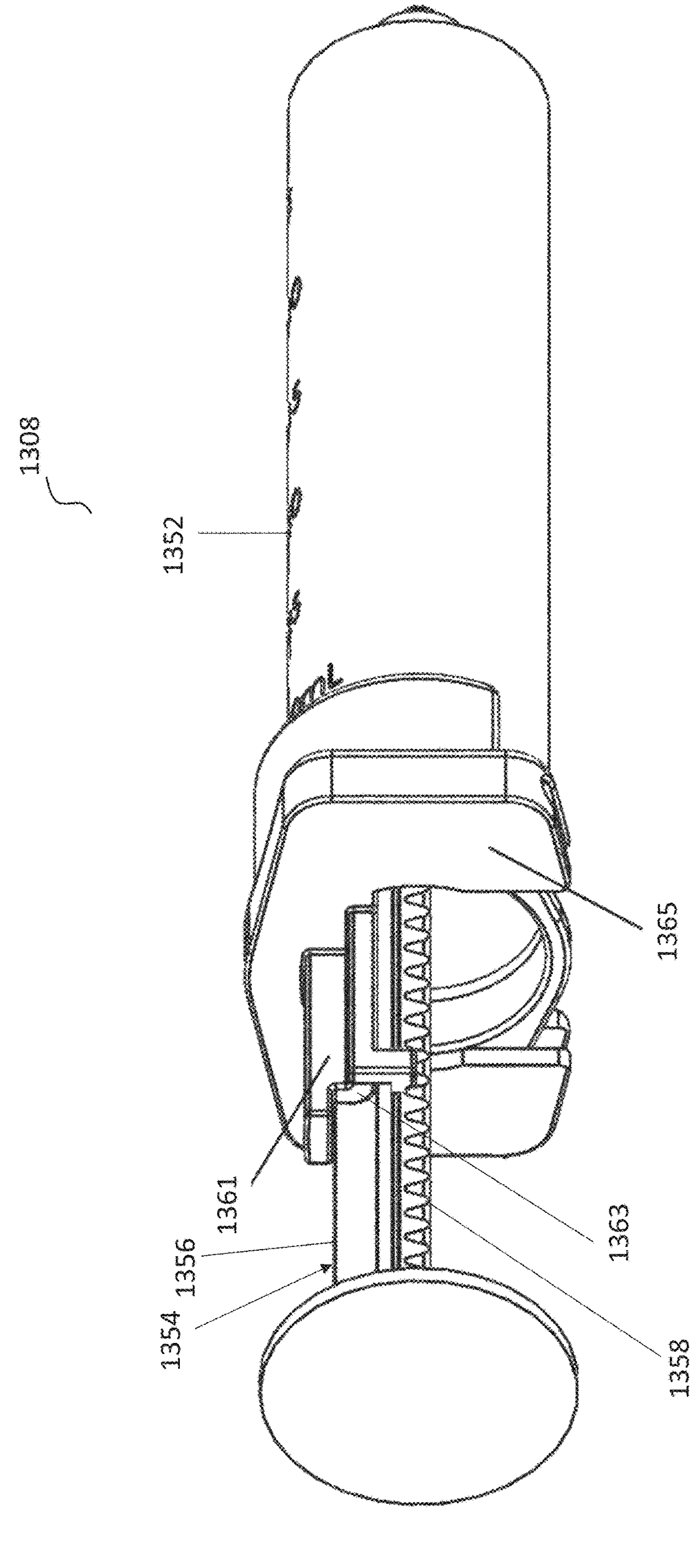
FIG. 10 illustrates an exemplary variation of a pump.

FIG. 10 illustrates an exemplary variation of a pump 1308 (e.g., structurally and/or functionally similar to pump 108 in FIG. 1A and FIG. 1B) configured for both manual usage and engagement with an actuator (e.g., a circular gear) for automatic control. The pump 1308 may comprise a cylindrical body 1352 and a plunger 1354. The plunger may comprise an enlarged end or head (not shown in FIG. 10 but shown in FIG. 11A as enlarged end 1462) and an elongate member 1356 coupled to and extending from the enlarged end. The enlarged end may be slidably positioned within the cylindrical body 1352, and both the enlarged end and the elongate member 1356 may be configured to move linearly within and/or relative to the cylindrical body 1352. The plunger, and more specifically, the elongate member 1356, may comprise an actuation element configured to engage with an actuator of a controller (e.g., system controller, device controller). For example, in some variations, the actuation element may be linear gear 1358. The linear gear 1358 may be configured to engage with a circular gear (not shown in FIG. 10) partially or fully positioned within a housing of the system or device controller so as to actuate the pump 1308.

In some variations, the syringe pump (e.g., pump 1308) may be coupled to and/or integrated with one or more sensors to identify and track a position of the plunger. The one or more sensors may be employed on or used with the plunger and/or other components of the syringe pump and/or the syringe pump controller to determine a position of, and/or track movement of, one or more components and/or to detect and/or determine the amount of fluid that has been removed from or received within the cylindrical body. For example, one or more sensors may be employed to detect the position of the plunger within the cylindrical body and/or track movement of the plunger, each of which may be used to inform syringe pump movements and/or to determine the amount of fluid delivered from or received in the cylindrical body. Additionally or alternatively, one or more sensors may be employed to detect the position of and/or track movement of one or more of the motor, one or more gears in a gearbox, and the actuator (e.g., circular gear) in the controller, which may be used to inform syringe pump movements and/or to determine the amount of fluid delivered from or received in the cylindrical body. The one or more sensors may be position sensors, motion sensors, or contact sensors, as will be described in more detail herein. In some variations, the syringe pump (e.g., the plunger) may comprise one or more sensors, the controller (e.g., device controller, system controller) may comprise one or more sensors, or both. The sensors may be communicably coupled to a processor, such as a processor in the controller (device controller, system controller). In some variations, the one or more sensors may include optical sensors, such as, for example, optical encoders, magnetic sensors, such as, for example, magnetic encoders, and/or contact sensors, such as, for example, linear potentiometers.

As mentioned above, in some variations, the one or more sensors, such as for example, linear potentiometers, optical sensors, and the like, may be employed on or used with the plunger to detect the position of the plunger within the cylindrical body and/or track movement of the plunger. The plunger (e.g., the elongate member of the plunger) may include one or more fiducial markers (fiducials) that may be configured to interact with a sensor to detect the position of the plunger and/or track plunger movement. For example, in some variations, the plunger (e.g., elongate member of the plunger) may comprise one or more engagement pins that may be detected (e.g., via contact) by the sensor, which may be housed in the housing of the controller (e.g., device controller, pump controller and/or system controller). In some variations, the sensor (e.g., a linear potentiometer) may comprise a slider with one or more channels configured to engage with the fiducial markers. The interaction between the slider and the fiducial markers may inform the controller of the position and/or movement of the plunger and thus a volume of fluid within the cylindrical body of the syringe pump.

The fiducial markers may be any suitable marker configured to be detected (e.g., via contact, optically, magnetically) by a sensor. For instance, the fiducial marker may be an engagement pin of any suitable shape (e.g., triangular, circular, cylindrical, elliptical, etc. cross-sectional shape). In some variations, the plunger may include a single fiducial marker to detect the position of the plunger and/or to track plunger movement. In some such variations, the sensor (e.g., slider of the linear potentiometer) may be configured to contact the entire length of the plunger. In other words, the linear potentiometer (e.g., the slider with one or more channels) may be configured to span the entire length of the plunger such that the single fiducial marker contacts at least a portion of the linear potentiometer at all times. A change in voltage and/or a change in resistance caused due to the single fiducial marker contacting the linear potentiometer may be indicative of the position of the plunger and thus volume of fluid in the syringe pump. In some variations, the plunger may comprise a plurality of fiducial markers (e.g., two, three, four, five, six, seven, eight, nine, ten or more) and/or a plurality of pairs or sets of fiducial markers (e.g., two, three, four, five, six, seven, eight, nine, ten or more). In some variations, the fiducial markers may be positioned along a single line, while in other variations the fiducial markers may be positioned along two or more lines. For example, in some variations, the fiducial markers may be spaced asymmetrically along two or more lines. In some variations, the distance between two fiducial markers on the plunger may be unique (e.g., the distances between each fiducial marker and each adjacent fiducial marker may be different).

In some variations, the fiducial markers may be offset from one another and/or may be spaced asymmetrically along the elongate member, such that when the fiducial markers contact/engage with the sensor (e.g., a linear potentiometer), they may provide a unique indicator or "code" for every position along the elongate member of the plunger. In some variations, the fiducial markers may additionally or alternatively assist the controller in determining an initial volume of the syringe. For example, the syringe may be inserted into or positioned within the controller (e.g., device controller, pump controller and/or system controller) housing at any volume suitable for a particular procedure. Since the volume may be different at different times and/or for different subjects, the controller may determine the initial volume of the syringe based on the interaction between the fiducial marker(s) and the sensor (e.g., interaction between the fiducial marker(s) and slider of the linear potentiometer). The interaction may inform a system (e.g., a blood flow control system) comprising the syringe of the total volume of fluid within the cylindrical body of the syringe upon coupling to (e.g., insertion or placement in) the controller housing.

Figure 26A:
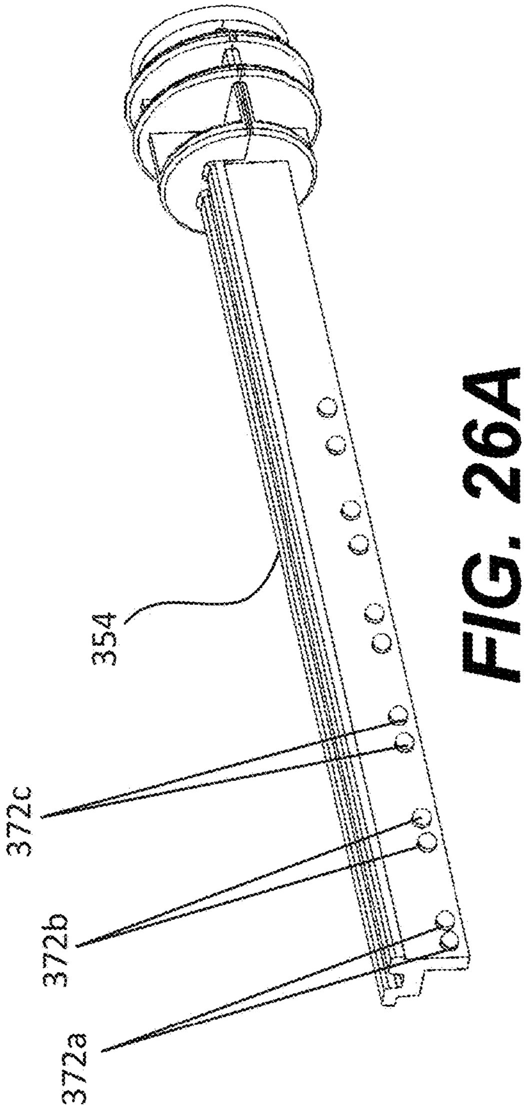
FIG. 26A illustrates an exemplary variation of fiducial markers along a plunger of a syringe of the blood flow control device.

FIG. 26A illustrates an exemplary variation of a plunger of a syringe included in a syringe pump comprising fiducial markers. As shown there, the elongate member of the plunger 354 may comprise a plurality of fiducial markers 372*a*, 372*b*, 372*c* (collectively referred to as fiducial markers 372) in the form of cylindrical pins. The plurality of fiducial markers 372 may have any suitable cross-sectional shape, such as, for example, circular, triangular, elliptical, square, a combination thereof, and the like, and any height suitable to contact or otherwise interact with a sensor. The fiducial markers 372 may be positioned along the length of the elongate member and may be grouped in pairs, although need not be. In some variations, the fiducial markers 372 may be non-linearly spaced. For instance, the spacing between each fiducial marker may be unique. Additionally or alternatively, the spacing between two fiducial markers in each pair of fiducial markers may be unique. For example, the distance between the two fiducial markers of the pair 372*a* may be different from the distance between the two fiducial markers of the pair 372*b*. In some variations, the distance between each pair of fiducial markers may be unique. For example, in FIG. 26A, the distance between the pair 372*a* and the pair 372*b* may be different from the distance between the pair 372*b* and the pair 372*c*. In some variations, the spacing between the fiducial markers may ensure that no more than two markers may engage with the linear potentiometer at a time. In some variations, the fiducial markers may be positioned on a single track (i.e., along a line) along the length of the elongate member of the plunger, and/or along a plurality of tracks (e.g., two, three, or more).

Figure 26B:
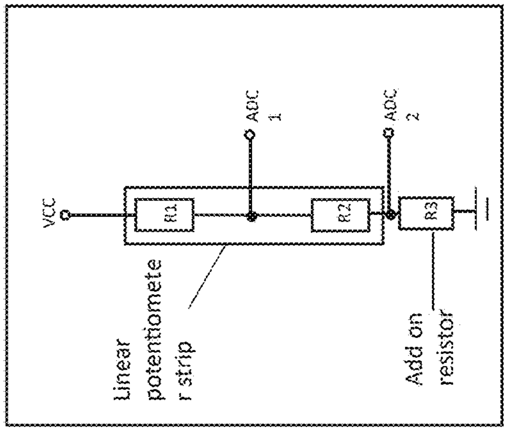
FIG. 26B illustrates an exemplary variation of an electrical circuit created when one fiducial marker is engaged with a linear potentiometer.
Figure 26C:
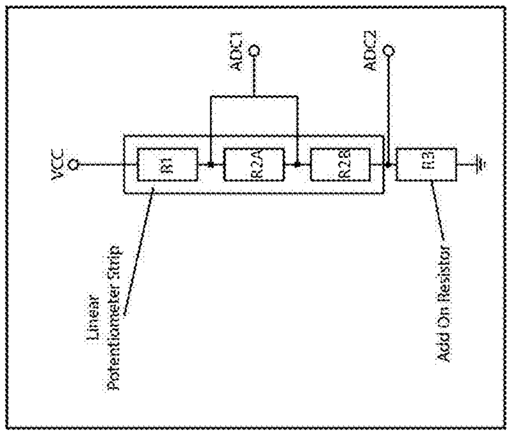
FIG. 26C illustrates an exemplary variation of an electrical circuit created when two fiducial markers are engaged with a linear potentiometer.

FIG. 26B illustrates an exemplary variation of an electrical circuit created when one fiducial marker is engaged with a linear potentiometer. FIG. 26C illustrates an exemplary variation of an electrical circuit created when two fiducial markers are engaged with a linear potentiometer. In some instances, it may be advantageous to utilize linear potentiometers to monitor the position and/or movement of the plunger because linear potentiometers provide precise measurements and generally have low power consumption. As depicted in FIG. 26B and in FIG. 26C, a linear potentiometer may generally comprise a slider with one or more channels. To create an electrical circuit, the linear potentiometer may also comprise a resistive element (e.g., resistive strip, resistor, etc.) with two or more terminals. The terminals of the resistive element may be connected such that when the slider of the linear potentiometer engages with fiducial marker(s), a voltage divider may be created.

For example, a total resistance of the linear potentiometer may be a fixed value. In FIG. 26B and FIG. 26C, the linear potentiometer may have three terminals. A resistance between a first terminal and a second terminal of the linear potentiometer is depicted as R1, and the resistance between the second terminal and a third terminal of the linear potentiometer is depicted as R2. When a single fiducial marker engages with the slider of the linear potentiometer, the total resistance of the linear potentiometer may be split into two resistances, such as for example, R1 and R2. Accordingly, a position of the fiducial marker that engages with the linear potentiometer in FIG. 26B may be determined from a ratio between the resistance R1 and R2. That is, the ratio between R1 and R2 in FIG. 26B may correlate to a position of the fiducial marker that engages with the linear potentiometer.

FIG. 26C illustrates an exemplary variation of an electrical circuit created when two fiducial markers are engaged with a linear potentiometer. In FIG. 26C, the second fiducial marker of the two fiducial markers may split the resistance R2 into R2A and R2B. The second fiducial marker may create a short around R2A. Therefore, the resistance between the first terminal and the second terminal may still be R1. The resistance between the second terminal and the third terminal may be R2B and the resistance between the first terminal and the third terminal may be the sum of R1 and R2B.

For both FIG. 26B and FIG. 26C, an additional resistor R3 may connected between the third terminal of the linear potentiometer and the circuit's ground. Accordingly, when a voltage is applied to the first terminal VCC, the voltage at the second terminal may be measured by ADC1 and the voltage at the third terminal may be measured by ADC2. If one fiducial marker is engaged with the linear potentiometer, such as in FIG. 26B, then the voltage measured by ADC2 may be a constant value based on the sum of resistances R1 and R2 (the sum may be constant since the total resistance of the potentiometer is constant and is split into R1 and R2) and resistance R3. The voltage measured at ADC1 may vary based on the position of the fiducial marker. Therefore, voltage ADC1 may be indicative of the position of the fiducial marker. In some variations, the voltage ADC1 may be transmitted to a controller (e.g., system controller, device controller, and/or pump controller). The position of the plunger determined from ADC1 may be used to calculate a position of the plunger and/or may be used to track a movement of the plunger.

However, if two fiducial markers are making contact with the linear potentiometer, such as in FIG. 26C, then R2 may decrease because of the shorting around R2A. The voltage measured at ADC2 may be correlated to the distance between the two fiducial markers while the voltage measured at ADC1 may be correlated to the position of a first fiducial marker of the two fiducial markers that may be engaged with the linear potentiometer. Therefore, an absolute position of the plunger may be derived from voltages measured at ADC1 and ADC2.

For instance, the spacing of the fiducial markers may be key to determining specifically which pair of fiducial makers may be currently engaged with the linear potentiometer. In addition, because the entire span and spacing between fiducial markers is known, it may be possible to determine the position of the plunger when even a single fiducial marker engages with the potentiometer. For example, since the entire span and the distances between the fiducial markers are known, a look up table may be generated to associate the voltage/resistance when each of the fiducial marker engages with the potentiometer, and the look up table may be used to determine the position (e.g., absolute position) of the plunger.

Since the variation in FIG. 26A comprises pairs of fiducial markers spaced across the length of the plunger, the length of the linear potentiometer may be an order of magnitude shorter than the length of the plunger. This is because when a plunger comprises only a single fiducial marker, the potentiometer (e.g., the slider of the potentiometer) may need to span the length of the plunger so that for every movement of the plunger at least some portion of the potentiometer (e.g., slider of the potentiometer) engages with the single fiducial marker. However, since in FIG. 26A, pairs of fiducial markers are spaced across the length of the plunger, even with a potentiometer of a shorter length, the potentiometer may engage with one or more fiducial markers for every movement of the plunger. The result of this design is that the overall form factor may be decreased, and the resolution of movement sensing may be substantially increased.

FIGS. 27A-27D illustrate another exemplary variation of fiducial markers interacting with a linear potentiometer. In this variation, the fiducial markers may be spaced asymmetrically along multiple tracks instead of a single track (e.g., single line). As discussed above, in some variations, the fiducial markers may be offset from one another and/or may be spaced asymmetrically along the elongate member, such that when the fiducial markers contact/engage with the sensor (e.g., linear potentiometer), they may provide a unique indicator or "code" for every position along the elongate member of the plunger.

In some variations, the sensor may be a multitrack linear potentiometer. That is, the sensor may comprise multiple channels to engage with the fiducial markers. More specifically, the sensor may be a linear potentiometer comprising a slider with two or more channels. Each channel may be configured to engage with one or more fiducial markers. For example, if the fiducial markers are placed on two tracks along the length of the plunger, then a first channel of the linear potentiometer may engage with fiducial markers on a first track and a second channel of the linear potentiometer may engage with fiducial markers on a second track.

Figure 27A:
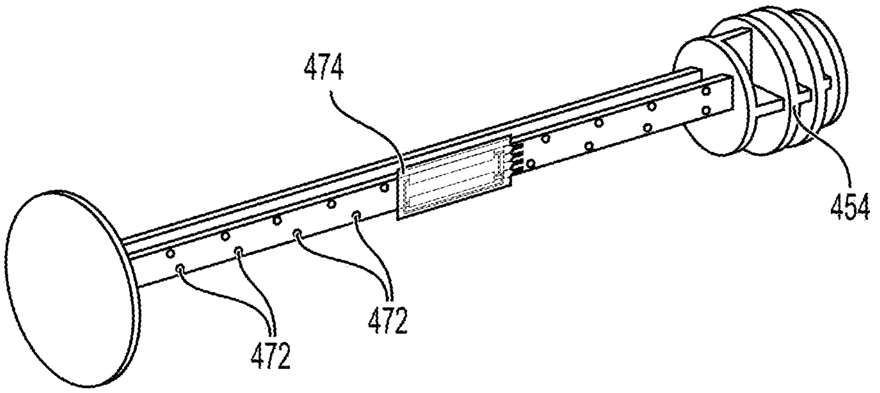
FIGS. 27A-27D illustrate another exemplary variation of fiducial markers interacting with a linear potentiometer of a plunger of a syringe.
Figure 27B:
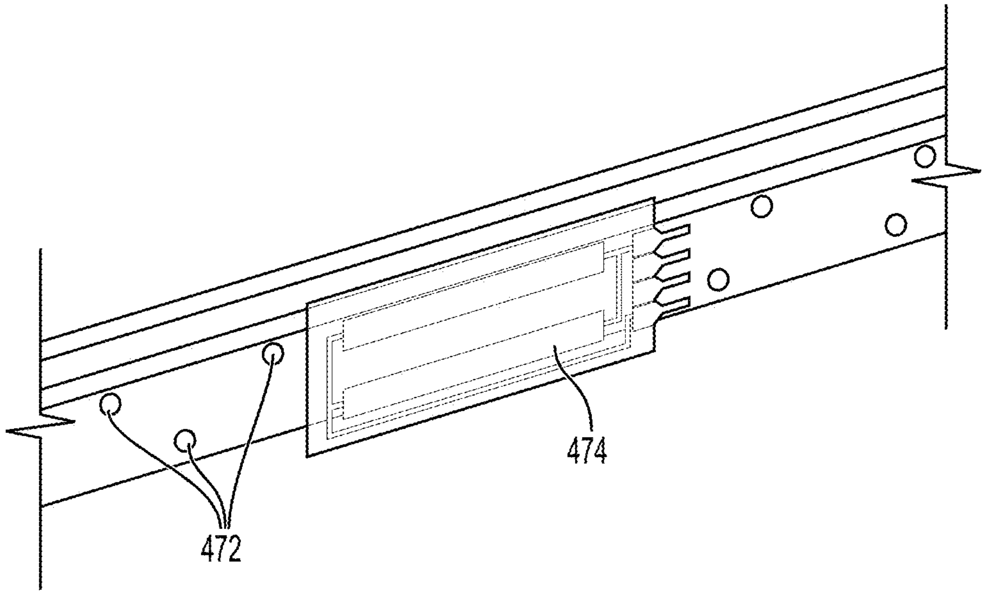
Figure 27C:
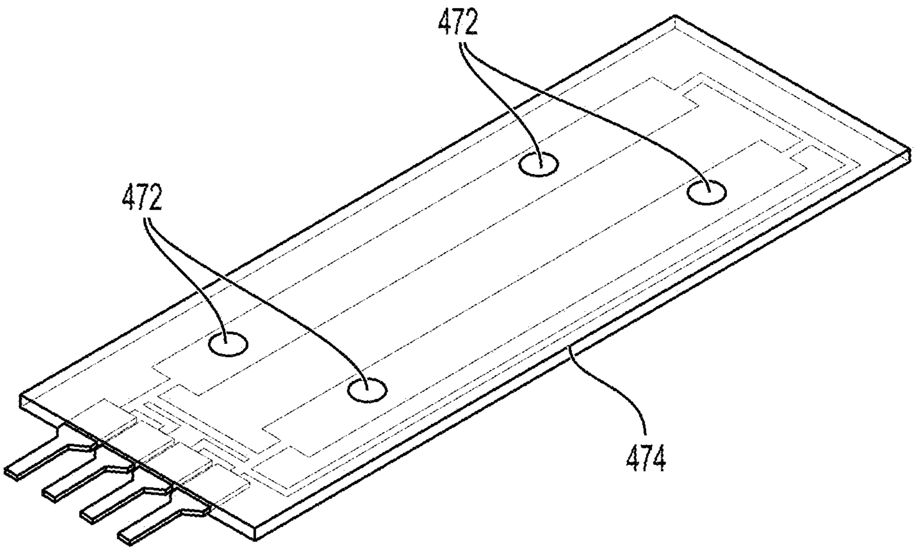
Figure 27D:
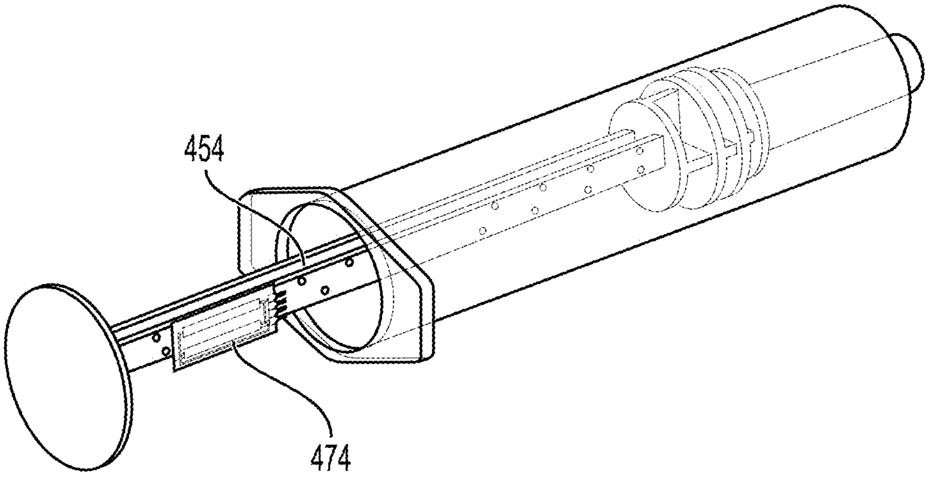

FIGS. 27A and 27B depict a linear potentiometer 474 engaging with engagement pins 472 positioned on multiple tracks (e.g., two). As seen in FIG. 27B, the linear potentiometer 474 comprises a slider with two channels (e.g., a multitrack potentiometer). When a multitrack linear potentiometer 474 is provided in or on the controller (e.g., system controller, device controller, and/or pump controller) housing to engage or otherwise interact with fiducial markers on the elongate member of the plunger 454, as shown in FIGS. 27A and 27B, engagement pins (fiducial markers) 472 on the side of the plunger 454 may contact the multitrack linear potentiometer 474 and provide precise measurements of actual syringe movement. Referring to FIGS. 27C and 27D, a series of offset engagement pins (fiducial markers) spaced asymmetrically along the length of the elongate member of the plunger may connect with the channels on the linear potentiometer to thereby provide a "code" for every position along the syringe. More specifically, the engagement pins 472 may be spaced in multiple lines along the length of elongate member. When a multi-channel potentiometer engages with one or more fiducial markers, the unique spacing between the fiducial markers may cause the linear potentiometer to generate a unique code indicative of the position of the plunger. In this manner, the movement of the plunger and/or the position of the plunger may be determined.

In some variations, the resistive element of the linear potentiometer described above may be a part of a resonator circuit that changes frequency in proportion to the change in the resistance. A controller (e.g., system controller, device controller, and/or pump controller) may measure the frequency of the resonator circuit to determine a position and/or movement of the plunger. In some variations, instead of the resistive element, the linear potentiometer may include a capacitive element that may change capacitance based on the engagement of the linear potentiometer with the fiducial markers. In such variations, the change in capacitance may change the frequency of the resonator circuit. The controller may measure the frequency of the resonator circuit to determine a position and/or movement of the plunger. In some variations, instead of the resistive element, the linear potentiometer may include one or more indicators that may change inductance based on the engagement of the linear potentiometer with the fiducial markers. In such variations, the change in inductance may change the frequency of the resonator circuit. The controller may measure the frequency of the resonator circuit to determine a position and/or movement of the plunger. In some variations, in addition to the fiducial markers above, a second set of fiducial markers and a second linear potentiometer may be positioned such that the second linear potentiometer and the second set of fiducial markers may provide an indication as to the position of the plunger relative to the cylindrical body.

Figure 12:
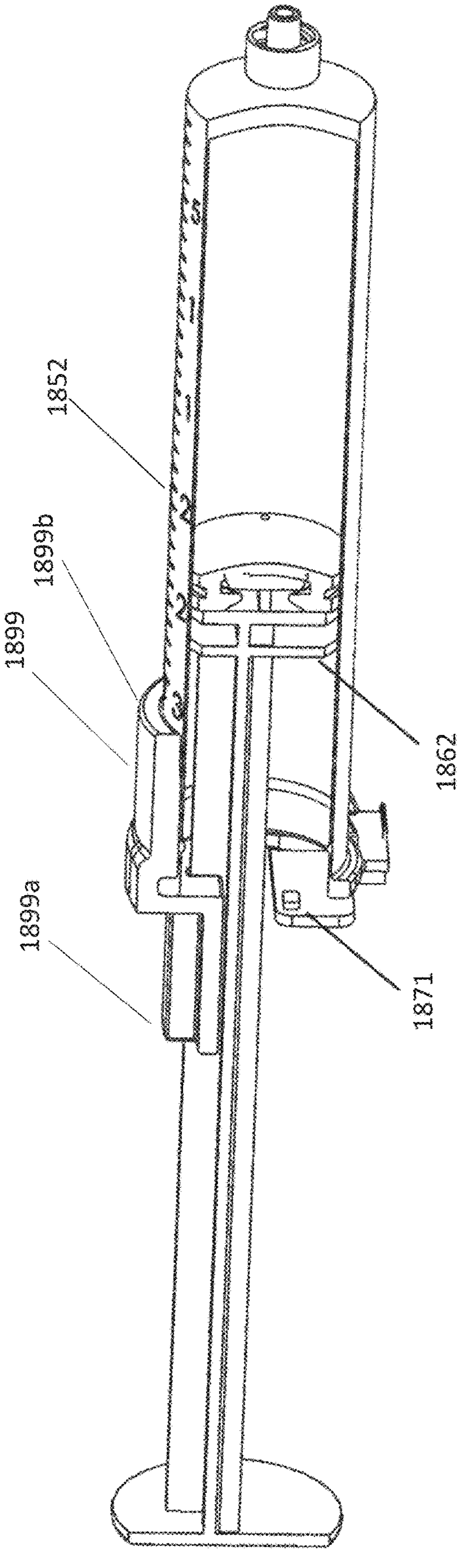
FIG. 12 illustrates an exemplary variation of a pump comprising an optical sensor.

In some variations, as mentioned above, optical sensors may be used to detect the position of the plunger within the cylindrical body and/or to track movement of the plunger. For example, referring back to FIG. 12, an exemplary variation of an optical sensor 1371 configured to detect the position of the plunger and/or to track the movement of the plunger is illustrated. In some variations, the optical sensor 1371 may be coupled directly to the pump as shown in FIG. 12. For instance, the optical sensor 1371 may be coupled to and/or integrated with a proximal end of the cylindrical body 1852. In some variations, the syringe pump may further comprise a sleeve 1899 coupled to or formally integrally with the proximal end of the cylindrical body, and the sensor may be attached to the sleeve. For example, in some variations, the sleeve 599 (e.g., a distal portion 1899*b*) may be configured to receive the proximal end of the cylindrical body and may be coupled to the proximal end of the cylindrical body in any suitable manner, such as, for example via snap-fit connectors or other mechanical connectors (e.g., screws, pins, etc.), an interference fit, adhesive, plastic welding, and/or the like. In some variations, a portion (e.g., a proximal portion 1899*a*) of the sleeve 1899 may be configured to contact and/or support a portion of the plunger. The optical sensor 1871 may be positioned on the sleeve 1899 such that the optical sensor 1871 may face towards the cylindrical body and towards the enlarged end 1862 of the plunger. As the plunger and consequently the enlarged end 1862 translates within the cylindrical body, light reflected from the enlarged end 1862 may be received by the optical sensor 1871. The volume of the fluid in the pump may be determined based on the detected reflected light. For instance, the sensor 1871 may transmit an amount of reflected light to a controller (e.g., system controller and/or device controller) that may determine a position of the enlarged end 1862 based on the amount of reflected light. The controller may use the position of the enlarged end 1862 to determine a volume of fluid in the pump. The volume of fluid in the pump may be used to determine the amount of fluid received in or delivered from the cylindrical body and/or to track the position and/or movement of the plunger.

Figure 13:
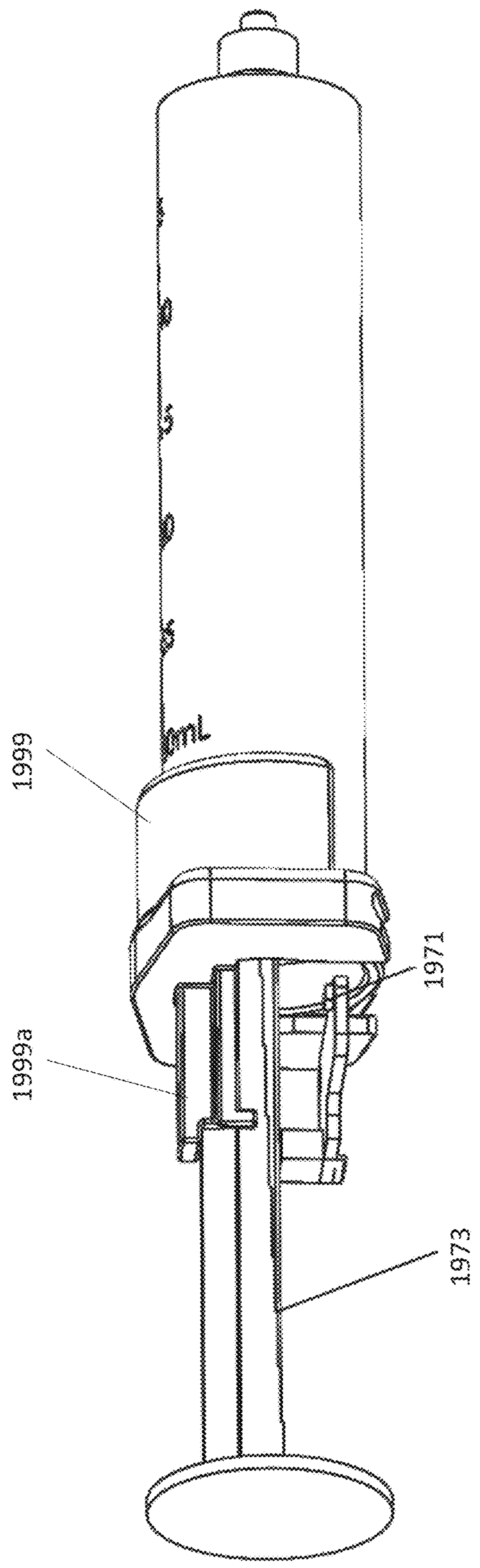
FIG. 13 illustrates an exemplary variation of a pump comprising an optical sensor.

FIG. 13 illustrates another exemplary variation of an optical sensor 1971 configured to detect the position of the plunger and/or to track the movement of the plunger. In FIG. 13, the optical sensor 1971 may be positioned on a sleeve 1999 such that the optical sensor 1971 may be oriented to face towards the plunger. A proximal end of the cylindrical body may be configured to receive the sleeve 1999. Additionally or alternatively, the sleeve may be attached to the proximal end of the cylindrical body in any manner described with respect to FIG. 12. As discussed, the optical sensor 1971 may be positioned on the sleeve 1999 such that the optical sensor faces the plunger. For instance, the optical sensor 1971 may face a bottom surface of the plunger. The plunger may include a marker 1973 configured to reflect light in a manner that allows the optical sensor 1971 to determine the position of the plunger based on the reflected light. In some variations, the marker 1973 may be a step-shaped marker spanning the length of the plunger. For instance, the step-shaped marker may include inclined surfaces spanning the length of the plunger such that light may reflect off the marker differently based on the position of the marker relative to the optical sensor 1971. The optical sensor 1971 may detect the light reflected from different portions of the step-shaped marker 1973 and these measurements may be used (e.g., via a controller described herein) to determine a position of and/or track movement of the plunger based on the detected light.

In some variations, magnetic sensors may be used to detect the movement and/or position of the plunger. The magnetic sensor may comprise a magnetic reader that may detect changes in magnetic fluxes. The magnetic sensor may be attached and/or coupled to the plunger. When the plunger moves, the magnetic reader may detect a change in the magnetic flux. This change may be processed by a controller (e.g., system controller and/or device controller) to determine a position and/or movement of the plunger.

In some variations, a sensor configured to detect the movement and/or position of the plunger may incorporate a roller or secondary gear. The roller or secondary gear may be configured to contact the plunger. This roller or secondary gear may have a higher ratio than the circular (pinion) gear, so a very small change in the position of the circular gear will result in a large rotation of the roller or secondary gear. The rotation of the roller or secondary gear may be detected for example, using magnetic, optical, and/or capacitive sensors. The amount of rotation of the roller or secondary gear may be processed by a controller (e.g., system controller and/or device controller) to determine a position and/or movement of the plunger.

As discussed above, the pump devices described herein may include sensors configured to detect the movement and/or position of the plunger. The plungers used in the syringe pumps described herein may be of various sizes, depending on the application, and the sensors may be configured to detect the movement and/or position of the plunger across the various potential sizes. The sensors may be configured to provide confirmation on whether the plunger has moved an intended amount. For example, as discussed above, the syringe pumps may include optical sensors such as optical encoders, magnetic sensors such as magnetic encoders, contact sensors such as linear potentiometer, etc. to detect movement and/or position of a plunger.

In some variations, the devices and systems described herein may include one or more sensors configured to detect a position and/or movement of a component other than the plunger and may utilize that position and/or movement as a corollary for the position and/or movement of the plunger, or may otherwise utilize the position and/or movement of that component to inform a determination of the position and/or movement of the plunger, an amount of fluid transferred (delivered or received), and/or size of an expandable member. For example, the blood flow control devices and systems described herein may include optical sensors such as optical encoders and/or magnetic sensors, such as magnetic encoders to detect a position and/or movement of an actuation mechanism (e.g., a motor), which in turn may, in some variations, be used to determine movement and/or position of the plunger. In other variations, the devices described herein may utilize the position and/or movement of the actuation mechanism (e.g., motor) to control or otherwise inform fluid transport without determining a particular position and/or movement of the plunger associated with that actuation mechanism's position and/or movement respectively. Sensors configured to detect the position and/or movement of the actuation mechanism may be included in the controller (system controller and/or device controller). For example, these sensors may be coupled (e.g., mechanically coupled and/or optically coupled, or magnetically coupled) to the actuation mechanism. The sensors may detect a change in reflected light (e.g., optical sensors) or a change in magnetic fluxes (e.g., magnetic sensors) due to movement of the actuation mechanism. This change may be analyzed by the processor of the controller (e.g., device controller, system controller). The processor may determine an amount of actuation mechanism movement (e.g., for a stepper motor, a number of steps the motor took) based on these changes. In some variations, the sensors may detect an amount of movement every certain period of time (e.g., a number of steps taken by the motor every certain period of time). For example, the sensors may detect an amount of movement every 9 seconds, every 8 seconds, every 7 seconds, every 6 seconds, every 5 seconds, every 4 seconds, every 3 seconds, every 2 seconds, or every second. Additionally or alternatively, such sensors may have high resolution relative to the actuation mechanism (e.g., motor). That is, such sensors may be configured to indicate a higher number of steps for every physical movement of the actuation mechanism. For instance, in variations in which the actuation mechanism includes a motor, the sensors may be configured such that the processor may indicate 20 steps for every physical movement of the motor.

As discussed above, the syringe 1308 may be automatically controlled by a controller (e.g., system controller, and/or device controller) via the engagement of the actuator and the actuation element. For example, referring to FIG. 10 specifically, the syringe 1308 may be actuated by engaging the actuator (e.g., linear gear 1358), with the actuation element (e.g., a circular gear) thus forming a rack and pinion mechanism. In contrast to lead-screw drive mechanisms that may extend beyond the length of the plunger 1354, the linear gear 1358, and thus the rack and pinion mechanism, may be incorporated entirely within the length of the plunger 1354. Accordingly, the overall footprint of the system may be reduced.

In some variations, the pump 1308 may include one or more features to control the orientation and the position of the pump 1308. For example, the elongate member 1356 may include a projecting rib 1361 that may be configured to fix an orientation of the linear gear 1358 relative to a flange 1365. The flange 1365 may be coupled to the cylindrical body 1352. The flange 1365 may allow a user to hold the pump 1308 when the pump 1308 is locked/coupled to a controller (e.g., system controller). The elongate member 1356 may also include a channel 1363 that may be configured to constrain a movement of the plunger 1354. For example, the channel 1363 may prevent the plunger 1354 from bending or tilting out of alignment during manual use. As seen in FIG. 10, the projecting rib 1361 may be positioned above the channel 1363. For instance, the projecting rib 1361 may be positioned to interact with the channel 1363.

Figure 11A:
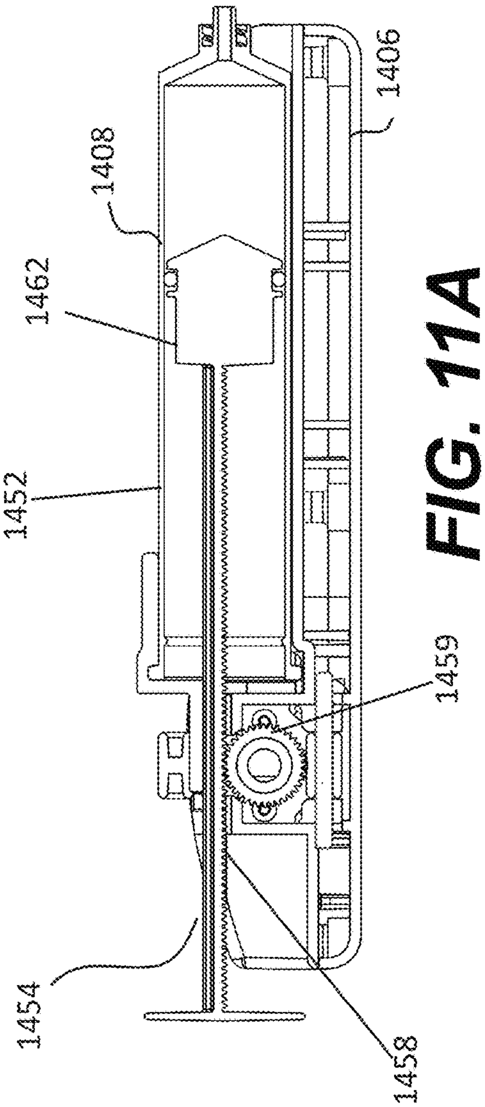
FIGS. 11A and 11B illustrate an exemplary variation of a linear gear engaging with a circular gear to actuate a pump.
Figure 11B:
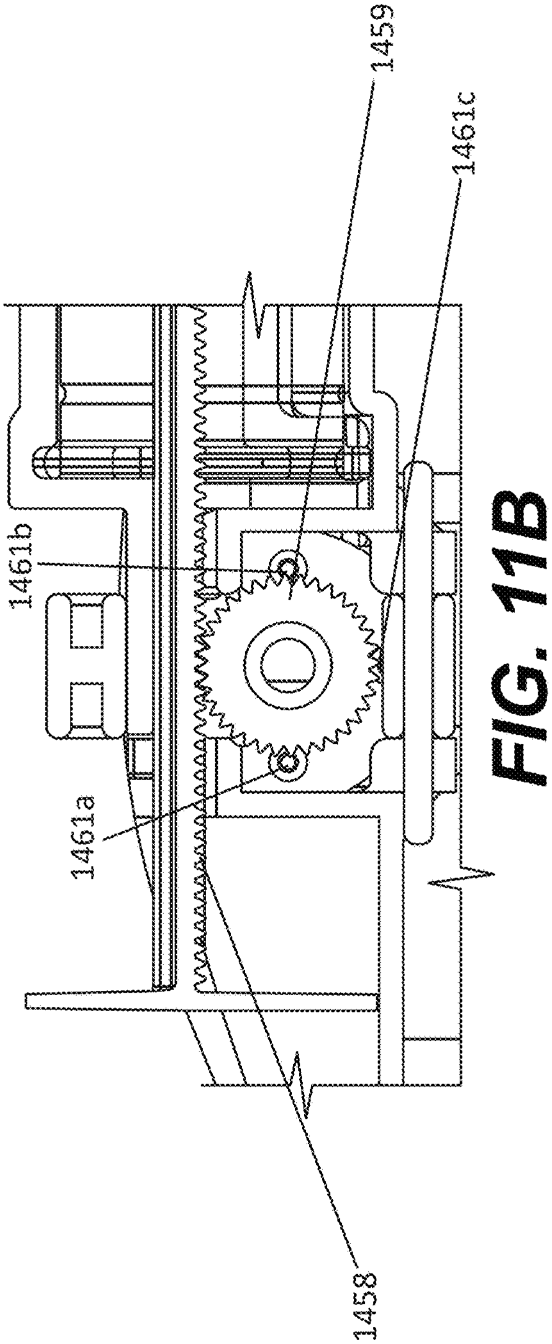

FIGS. 11A and 11B illustrate an exemplary variation of a linear gear 1458 of a pump 1408 engaging a circular gear 1459 of a controller 1406 (e.g., system controller, device controller) to actuate the pump. The system (e.g., system controller, device controller) may comprise a motor coupled to, and configured to move, the circular gear 1459. The circular gear 1459 may engage with the linear gear 1458. Therefore, movement of the circular gear 1459 may translate into movement of the linear gear 1458. As the linear gear 1458 moves, the plunger of the pump 1408 moves within the cylindrical body, thereby transferring fluid in or out of the pump 1408 and to or from the expandable member.

The plunger 1454 may comprise features to aid in achieving precise plunger movements. In some variations, the plunger 1454 make comprise an enlarged end 1462. The enlarged end 1462 may prevent the plunger 1454 from being fully removed from the cylindrical body 1452. In some variations, the enlarged end 1462 of the plunger 1454 may comprise an injection molded tip (e.g., tip of the enlarged end 1462) with minimal volume of compliant material (e.g., polycarbonate (PC), Acrylonitrile butadiene styrene (ABS) or PC/ABS blend, or nylon) to avoid compression, flexing and associated loss of accuracy (e.g., precise movement of the plunger) under high pressure. In some variations, the pump may include a seal between the plunger 1454 and the cylindrical body 1452. The seal may be a soft silicone O-ring in a groove that may be designed to achieve the necessary seal pressures with minimal sliding friction so as to aid to precise plunger movement at low pressure. In some variations, the seal may also be maintained free of leaks at 1.5 times the maximum expandable member pressure.

In some variations, the actuator may be selected for a high gear ratio and fine pitch. This may allow for precise control of the pump, and may provide for more precision than is possible manually. In some variations, the actuator (e.g., a circular gear) may be coupled to a gearbox affixed and/or coupled to a motor, (e.g., a stepper motor) that may actuate the actuator. The gearbox may be mounted on the system controller housing via screws 1461*a*, 1461*b*, and 1461*c*.

In some variations, the gear ratio of the gearbox may be between about 40:1 and about 150:1. In some variations, the gear ratio may be for example between about 130:1 and about 60:1, between about 115:1 and about 75:1, between about 105:1 and about 85:1, between about 97:1 and about 82:1, between about 95:1 and about 85:1, between about 92:1 and about 87:1 (including all values and sub-ranges therein). In some variations, the gear ratio of the gearbox may be about 90:1 In some variations, the ratio of the rotation of the circular gear to the linear translation of the linear gear may depend on the pitch diameter of the circular gear. In some variations, the pitch diameter of the circular gear may be between about 4 mm and about 20 mm, between about 6 mm and about 18 mm, between about 8 mm and about 16 mm, between about 10 mm and about 15 mm (including all values and sub-ranges therein). In some variations, the pitch diameter of the circular gear may be about 14.4 mm. In some variations the module (metric pitch) may be between about 0.4 mm and about 1.0 mm (including all values and sub-ranges therein). In some variations, the module may be 0.4 mm.

In some variations, the blood flow control systems described herein, and more specifically, the actuator and corresponding actuation element (e.g., the rack and pinion mechanism) described herein may be configured to quickly inflate and/or deflate relatively large volume expandable members, as well as provide for small, precise inflation and/or deflation movements. For example, the actuator and actuation element may be configured to operate at high speeds for large volume inflations and deflations, up to a safe limit of, for example, between about 0.3 cc/sec and about 5 cc/sec, between about 0.4 cc/sec and about 4 cc/sec, between about 0.5 cc/sec and about 3 cc/sec, between about 0.6 cc/sec and about 2 cc/sec (including all values and sub-ranges therein). In some variations, the actuator and actuation element may be configured to operate up to a safe limit of 1 cc/sec. The actuator may be configured for rapid full inflation and deflation of a large, compliant expandable member. In some variations, the actuator may be configured for rapid inflation and deflation of an expandable member with a volume of up to between about 20 cc and about 40 cc, between about 25 cc and about 35 cc, between about 28 cc and about 32 cc (including all values and sub-ranges therein). In some variations, the actuator may be configured for rapid inflation and deflation of an expandable member with a volume of up to 30 cc. Additionally or alternatively, the inflation and the deflation of the expandable member may be slow in order to control the occlusion of the blood vessel. Accordingly, the actuator and actuation element may be configured for small 50 μL inflation and deflation movements in predefined time intervals, e.g., in intervals ranging from 2 second to 15 seconds, including all values and sub-ranges therein. The predefined time intervals may be set so that there is sufficient time to see the effects of the inflation/deflation. For example, the time interval may be 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, or 15 seconds. In one variation, an 8 second interval (equivalent to 1800 motor movements over a 4-hour period of use) may be used to control occlusion of a large blood vessel. In some variations, the actuator in combination with the pump design may also maintain performance under expandable member pressures up 1.5 times the anticipated maximum clinical use of 600 mmHg catheter balloon pressure (up to 900 mmHg).

In some variations, one or more sensors may be employed on or used with the plunger to detect the position of the plunger within the cylindrical body and/or track movement of the plunger. In some variations, the system controller and/or the pump may include a motion sensor and/or position sensor that may be communicably coupled to both the pump and the device controller and/or system controller. In some variations, the one or more sensors that may be employed on or used with the plunger to detect the position of the plunger within the cylindrical body and/or track movement of the plunger may be optical sensors. In other variations, the one or more sensors that may be employed on or used with the plunger to detect the position of the plunger within the cylindrical body and/or track movement of the plunger may be magnetic sensors.

System Controller

In some variations, the blood flow control system may comprise a system controller 106 in addition to, or instead of, the device controller 112. While FIG. 1 depicts a cable extending from the system controller 106, it is understood that the cable does not need to be included. The system controller 106 may be coupled to the blood flow control device 104, for example, via the device controller 112, or in variations without a device controller 112, via the elongate body 102 directly. The system controller 106 may be communicably coupled to the sensors in the system. For example, the system controller 106 may be communicably coupled to one or more of the proximal sensors, the distal sensor, the expandable member sensor, the barometer, and the flow sensor (when included), and, in variations comprising more than one controller, may be communicably coupled to the device controller 112. For example, in some variations, the proximal sensor and the distal sensor may be electronically coupled to the device controller 112, which in turn may be communicably coupled to the system controller 106. Sensor readings may be transmitted from the device controller 112 to the system controller 106. As discussed in more detail herein, the device controller 112 may comprise a housing, which may contain a number of electronic components, such as, for example, the biasing circuit, the amplifier, the filter, and the ADC circuit. The sensor readings extracted from the ADC circuit may be transmitted from the device controller 112 to the system controller 106.

The system controller 106 and the device controller 112 may be communicably coupled to each other. In some variations, the blood flow control device 104 (e.g., device controller 112) may be releasably or non-releasably coupled mechanically to the system controller 106. For example, in some variations, a housing of the device controller 116 may be releasably coupled to the housing of the system controller 106. In some variations, the device controller 112 may be mechanically coupled to the system controller 106 in any suitable manner. For instance, the device controller 112 may be mechanically coupled to the system controller 106 via a coupling and/or alignment mechanism, such as, for example, a fastener, a latch, a mount, a joint, one or more magnets, a friction fit, a combination thereof, or the like. In some variations, the device controller 112 may be coupled to the system controller 106 via multiple coupling and/or alignment mechanisms. For example, the device controller 112 may be coupled to the system controller 106 via one or more magnets and via one or more fasteners or mechanical connectors (detents, latches, etc.), or via two or more sets of fasteners or mechanical connectors. Utilizing multiple sets of coupling and/or alignment mechanisms may allow for aligning the blood flow control device 104 (e.g., a device controller 116) with a system controller 116 and additionally locking the relative positions of the two controllers and/or otherwise securely coupling the two together. In some variations, the blood flow control device 104 may be electrically coupled with the system controller 106.

Figure 14B:
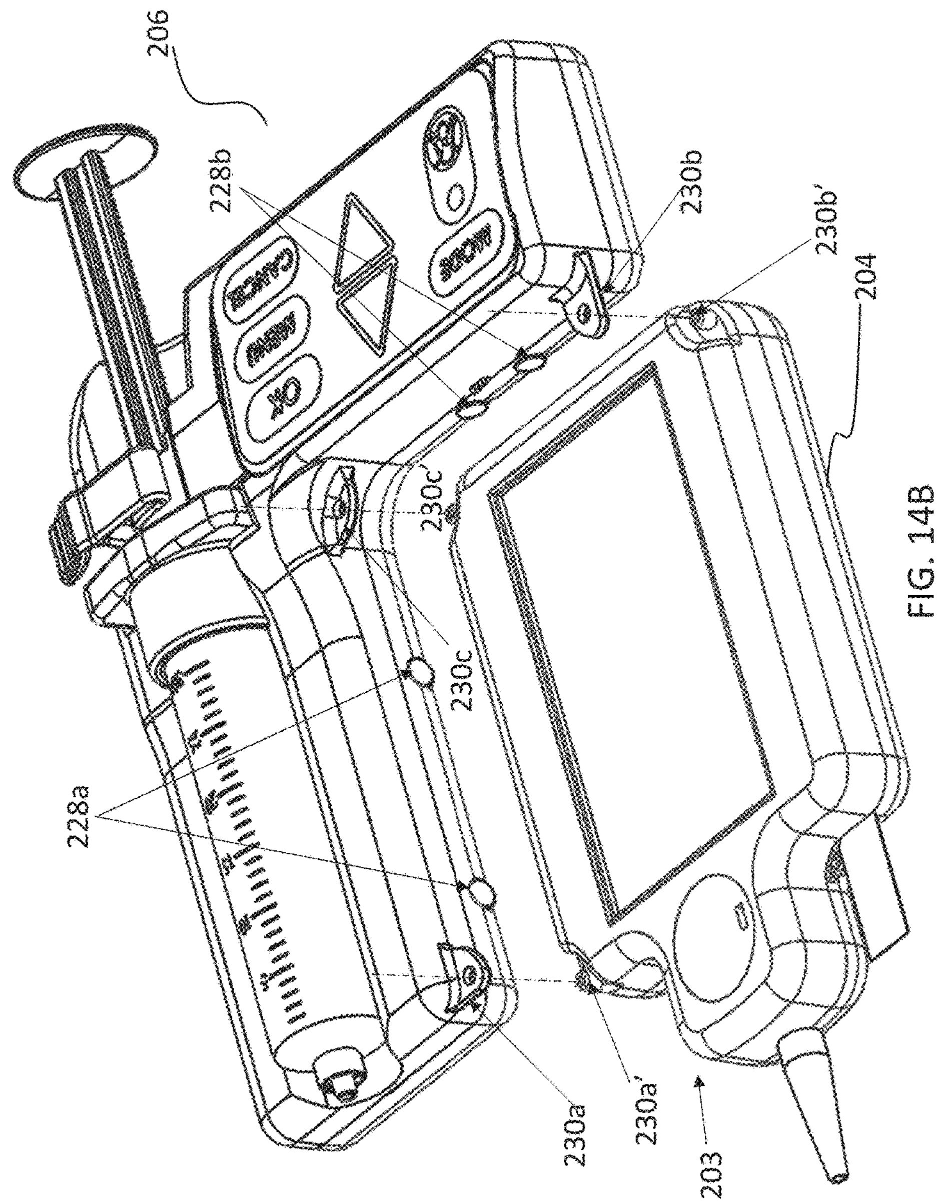
FIGS. 14A-14F illustrate exemplary variations of coupling and alignment mechanisms for releasably coupling a blood flow control device and a system controller.
Figure 14A:
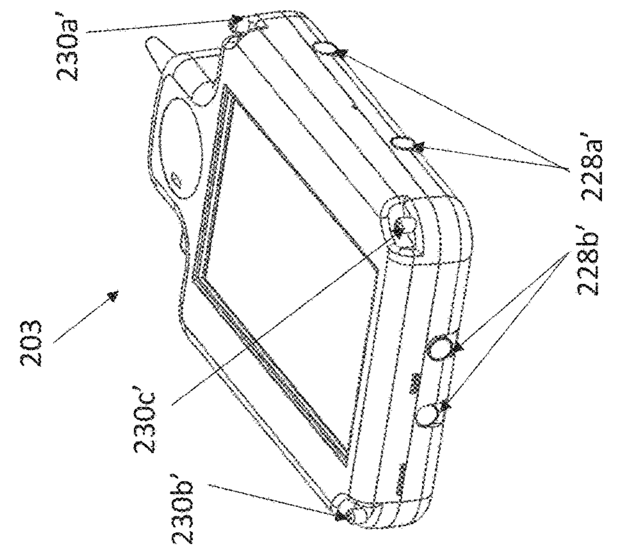
Figure 14C:
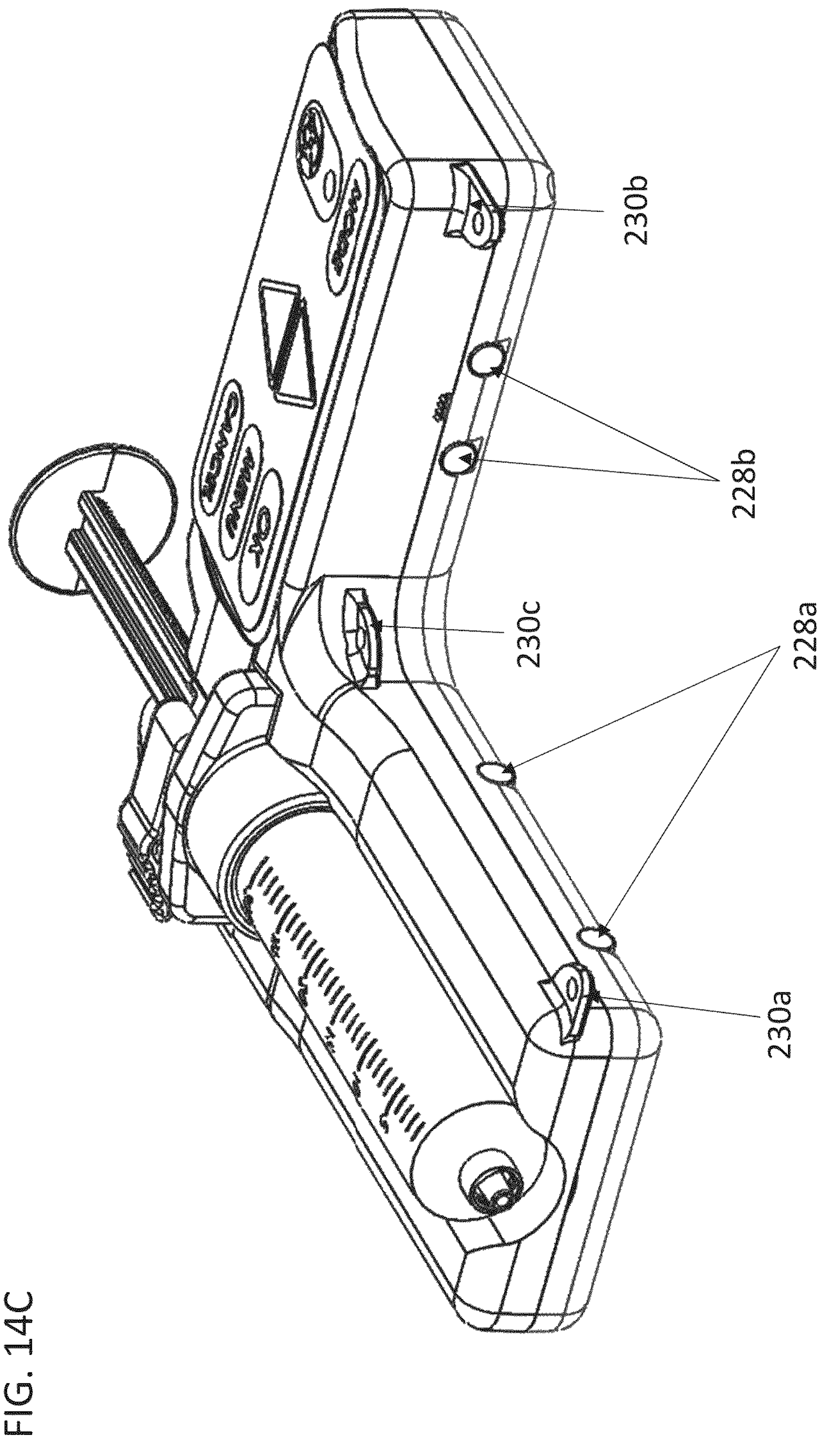

FIGS. 14A-14C illustrate an exemplary variation of a coupling and alignment mechanism comprising one or more magnets for a blood flow control device 203 (e.g., structurally and/or functionally similar to blood flow control device 104 in FIG. 1A and FIG. 1B) and a system controller 206 (e.g., structurally and/or functionally similar to system controller 106 in FIG. 1A and FIG. 1B). In FIG. 14C, the system controller 206 may include magnetic pins **228*a* on a first surface of the housing of the system controller 206 and magnetic pins 228*b* on a second surface of the housing of the system controller 206. The system controller 206 includes a first coupling extension 230*a*, a second coupling extension 230*b*, and a third coupling extension 230*c* to mechanically couple the system controller 206 with the blood flow control device 203**.

As seen in FIG. 14A, a first surface of the housing the system controller 206 may one or more magnets (e.g., two, three, four, five, six or more), such as, for example, magnetic pins **228*a*. The magnetic pins 228*a* may magnetically couple with magnetic pins 228*a*' (as seen in FIG. 14B) on a first surface of the housing of the device controller 204 of the blood flow control device 203 (only partially depicted). Similarly, a second surface of the system controller 206 may include magnetic pins 228*b*. The magnetic pins 228*b* may couple with magnetic pins 228*b*' (as seen in FIG. 14B) on a second surface of the housing of the device controller 204 of the blood flow control device 203. The magnetic pins 228***a* on the system controller 206 with their corresponding counterpart magnetic pins 228*a*' on the device controller 204 and the magnetic pins 228*b* on the system controller 206 with their corresponding counterpart magnetic pins 228*b*' on the device controller 204 may releasably couple the blood flow control device 203 with the system controller 206, and may align the controllers.

In some variations, a housing of the system controller 206 may comprise coupling extensions to hold the magnetic coupling in place. For example, the magnetic coupling may be held in place by a first coupling extension 230*a* on the system controller 206 that may be coupled to a pin 230*a*' on the blood flow control device 204, a second coupling extension 230*b* on the system controller 206 that may be coupled to a pin 230*b*' on the device controller 204 of the blood flow control device 203, and a third coupling extension 230*c* on the system controller 206 that may be coupled to a pin 230*c*' on the device controller 204. The first coupling extension 230*a*, the second coupling extension 230*b*, and the third coupling extension 230*c* may each include an opening or cavity. The pins 230*a*', 230*b*', and 230*c*' may fit into the respective openings, thereby locking the blood flow control device 203 to the system controller 206.

In some variations, the device controller 204 and the system controller 206 may be aligned such that the magnetic pins 228*a* magnetically couple with magnetic pins 228*a*' and magnetic pins 228*b* magnetically couple with magnetic pins 228*b*'. The magnetic coupling may be held in place by mechanically coupling the first coupling extension 230*a* with pin 230*a*', the second coupling extension 230*b* with pin 230*b*', and the third coupling extension 230*c* with pin 230*c*'. In some instances, the device controller 204 and the system controller 206 may be aligned such that the first coupling extension 230*a* mechanically couple with pin 230*a*', the second coupling extension 230*b* mechanically couple with pin 230*b*', and the third coupling extension 230*c* mechanically couple with pin 230*c*'. This alignment may cause the magnetic pins 228*a* to magnetically couple with 228*a*' and magnetic pins 228*b* to magnetically couple with 228*b*'. In this manner, the blood flow control device 203 may be operably coupled to the system controller 206 by a combination of magnetic coupling and mechanical coupling.

Figure 14E:
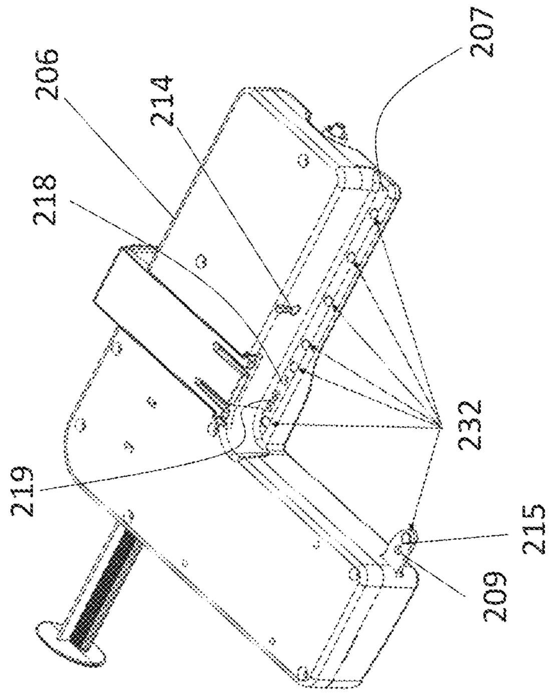
Figure 14D:
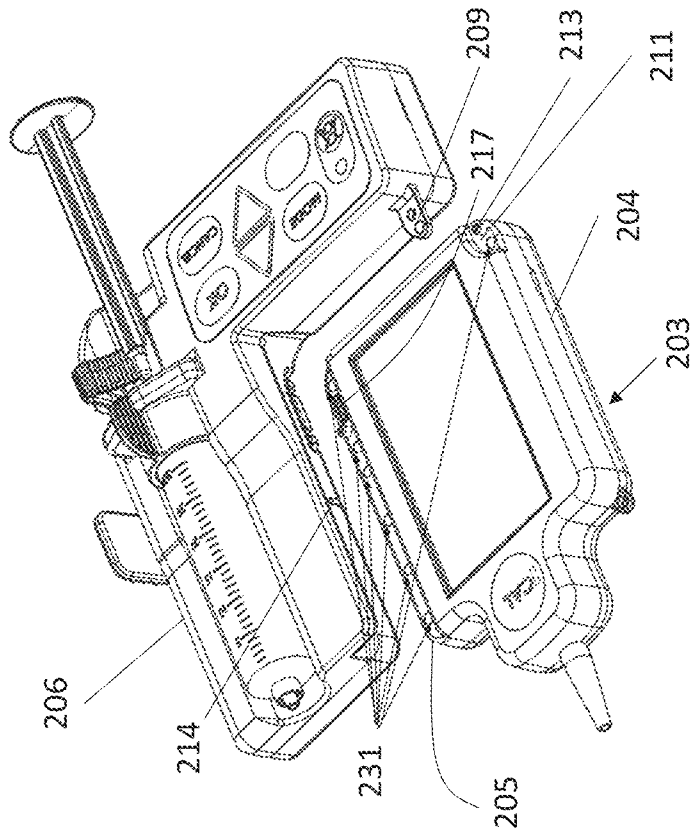
Figure 14F:
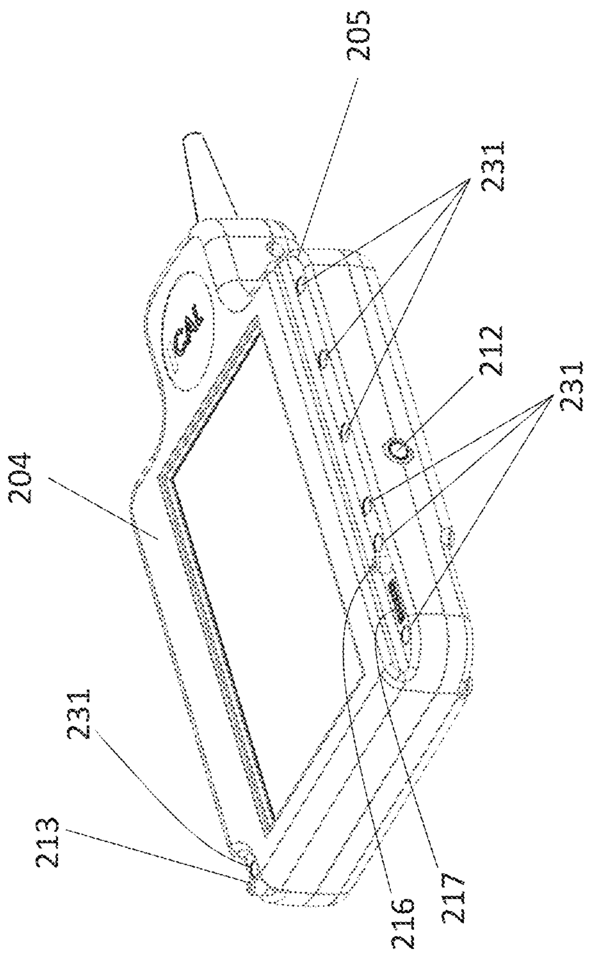

The magnets (e.g., magnetic pins) may have any suitable size and shape, and may be disposed on the blood flow control device 203 and system controller 206 in various ways. For example, in addition to having a size and arrangement as described above, the magnets 231, 232 may have a smaller size so that they may be placed on the device controller 204 and system controller 206 such that they face North (N) or South (S), as shown in FIGS. 14D and 14E, instead of East (E) or West (W), as illustrated in FIGS. 14A-14C. Referring to FIGS. 14D and 14E, magnets 231 may be placed on a ledge 205 of the device controller 204 of the blood flow control device 203, and a corresponding set of magnets 232 may be placed on a corresponding ledge 207 of the system controller 206. The spacing between the magnets 231, 232 may be the same or different. Although four magnets are shown in FIGS. 14A-14C, and seven magnets are shown in FIGS. 14D and 14E, any number of magnets may be used to magnetically couple the device controller 204 to the system controller 206. In addition to magnets, alignment and coupling of the device controller 204 and the system controller 206 may be enhanced using a mechanical connector, such as a ball detent 212 (shown in FIG. 14F), disposed on a side (inside surface) of the device controller 204. The mechanical connector may be configured to be releasably received within or otherwise engage with a corresponding connector or other corresponding component on the side (e.g., inside surface) of the system controller 206. For example, the ball detent 212 on the device controller 204 may fit into a corresponding groove and/or opening 214 on the system controller 206. The system controller 206 may have an extended portion 209 that may be configured for receipt in a corresponding recess 211 in the device controller 204, and corresponding magnets may be positioned on each structure. To further help secure the device controller 204 and thus the blood flow control device 203 to the system controller 206, the recess 211 may include a post 213 that fits within a corresponding opening 215 within the extended portion 209. An additional post 216 may be provided on the ledge 205 of the device controller 204 that fits within a corresponding opening 218 within the ledge 207 of the system controller 206. The ledge 205 of the device controller 204 may also include an electrical connector 217 that is configured to connect with a complementary electrical connector (e.g., a spring-loaded connector) 219 on the ledge 207 of the system controller 206 to form an electrical circuit therebetween. Placement of the electrical connectors 217, 219 on the ledges 205, 207 may help protect the electrical connection from, for example, the fluid being delivered when the device controller 204 is coupled to the system controller 206. In some variations, after alignment and coupling with the magnets and posts, a latch may be used to lock the device controller 204 to the system controller 206, as further described below.

Figure 15:
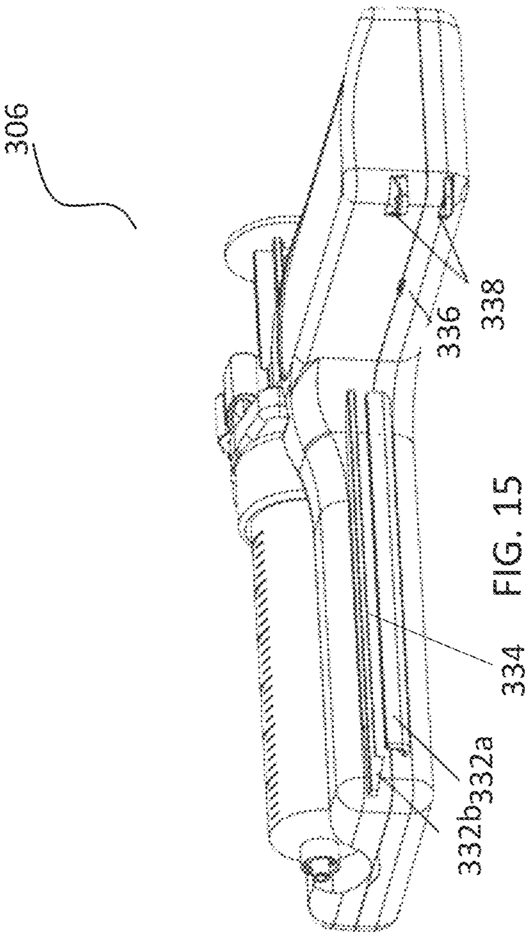
FIG. 15 illustrates another exemplary variation of a coupling and alignment mechanism for releasably coupling a blood flow control device and a system controller.

FIG. 15 illustrates another exemplary variation of a coupling and/or alignment mechanism for a blood flow control device (not shown in FIG. 15) (e.g., structurally and/or functionally similar to blood flow control device 104 in FIG. 1A and FIG. 1B) and a system controller 306 (e.g., structurally and/or functionally similar to system controller 106 in FIG. 1A and FIG. 1B). As seen in FIG. 15, a first side of the housing of the system controller 306 may include a first elongate track portion 332*a* and a second elongate track portion 332*b*. The first elongate track portion 332*a* and the second elongate track portion 332*b* may form an elongate channel 334 that may be configured to receive a portion of the blood flow control device. For example, the first elongate track portion 332*a* may be a slide that couples with a corresponding slide on the blood flow control device. The slide on the blood flow control device may be configured (sized, shaped) to be received between the first and second elongate track portions (332*a*, 332*b*) such that the slide is positioned within the elongate channel 334. The second elongate track portion 332*b* additionally be configured to lock the blood flow control device in position. For example, the elongate track portion 332*b* may comprise a snap that locks the blood flow control device in the elongate channel when the blood flow control device is inserted into the elongate channel 334. Additionally or alternatively, in some variations, the system controller 306 may include one or more extensions to hold the blood flow control device in position. The system controller 306 may include a first coupling extension and a second coupling extension 338 to hold the blood flow control device in position. For example, the first coupling extension and the second coupling extension 338 may be a pair of bosses that may prevent the blood flow control device from rotating out of alignment.

The blood flow control device may also be electrically coupled to the system controller 306. In some variations, the blood flow control device may be electrically coupled to the system controller 306 via an electrical connector 336 on the device controller. The electrical connector may be any suitable electrical connector, such as for example, an electrical port configured to receive a wired connection (e.g., cable). In some variations, the electrical connector 336 may be a spring-based electrical connector, such that the system controller 306 is biased towards the blood flow control device. For instance, the electrodes that electrically couple the blood flow control device with the system controller 306 may be coupled to or otherwise comprise a spring such that they are pushed towards the electrodes in the system controller 306 when the blood flow control device is mechanically coupled to the system controller 306. Physiologic conditions and/or data may be transmitted between the system controller 306 and the blood flow control device via the electrical connector 336.

Figure 33B:
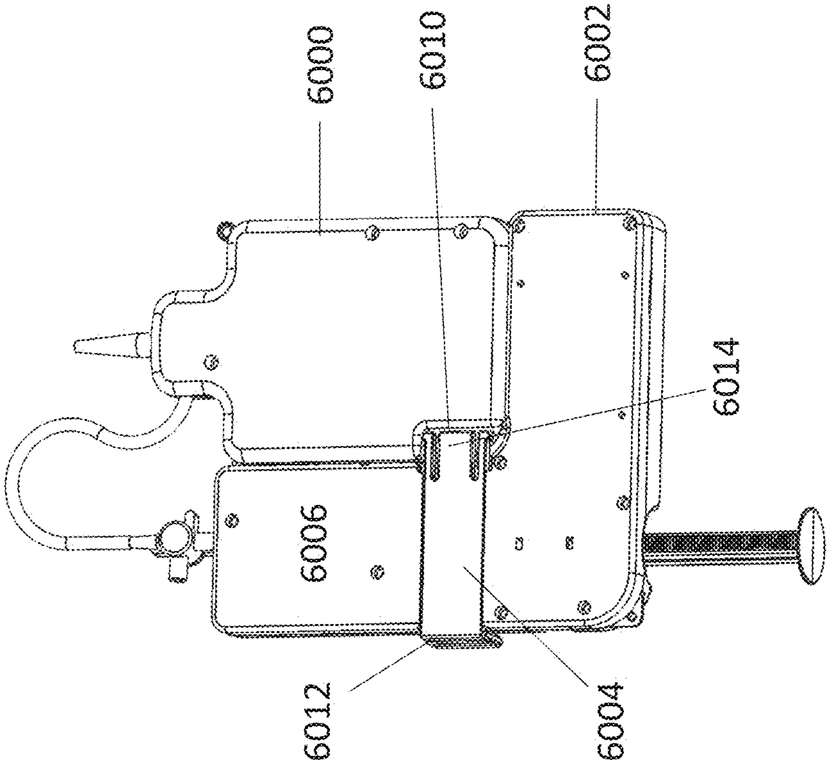
FIGS. 33A and 33B depict another exemplary variation of a coupling and alignment mechanism including a sliding latch for releasably coupling a blood flow control device and a system controller.
Figure 33A:
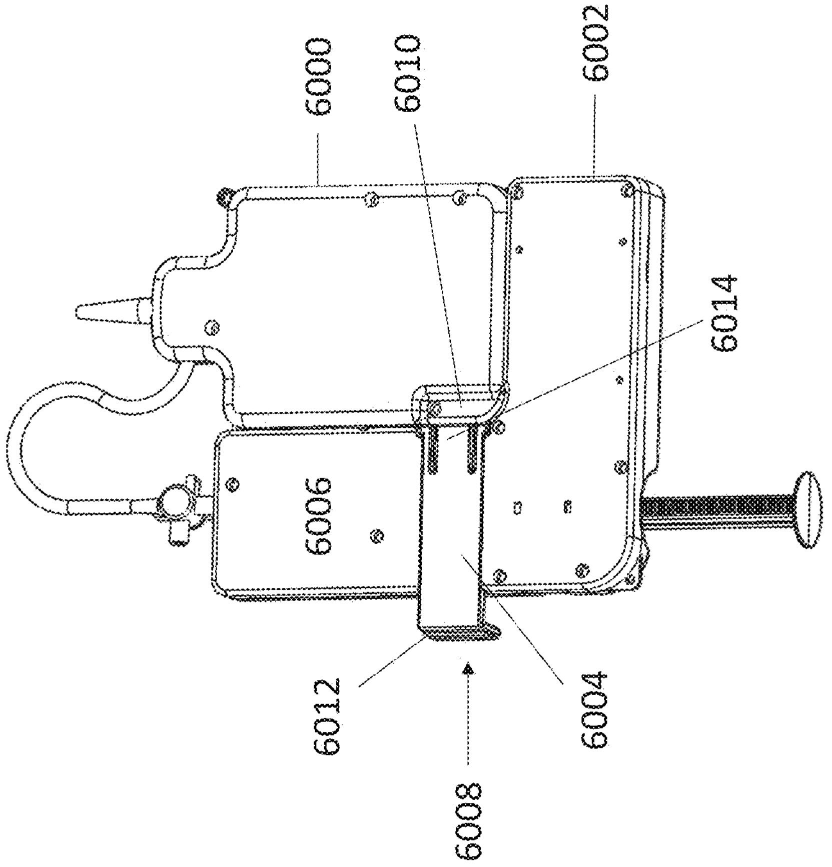

Another exemplary coupling and alignment mechanism for a blood flow control device and system controller may include a latch. The latch 6004 may have an unlocked configuration, as shown in FIG. 33A, and a locked configuration, as shown in FIG. 33B. Referring to FIG. 33A, a blood flow control device 6000 (device controller) is shown aligned with a system controller 6002 that includes a latch 6004 slidingly coupled thereto. Latch 6004 may include a first end 6012 and a second end 6014. A force may be applied on the first end 6012 of the latch 6004 in the direction of arrow 6008 (i.e., toward the blood flow control device 6000) to slide latch 6004 along the back surface 6006 of the housing of the system controller 6002 until the second end 6014 of the latch 6004 engages a cutout or recessed portion 6010 in the controller housing of the blood flow control device 6002. A gap between a portion (e.g., inside surface) of the first end 6012 of the latch 6004 and a portion (e.g., side surface) of the system controller housing 6002 may decrease and the portion of the first end 6012 of the latch 6004 may contact the portion of the system controller 6002 housing. Receipt of the second end 6014 of the latch 6004 in the cutout 6010 and/or contact between the first end 6012 of the latch 6004 and the system controller housing 6002 may then releasably lock the blood flow control device 6000 (via the device controller) to the system controller 6002, as shown in FIG. 33B. Receipt and locking of the second latch end 6014 in the cutout 6010 may also include depressing the second latch end 6014 and/or another part of the latch 6004 such that the second latch end 6014 secures the device controller of the blood flow control device 6000 to the system controller 6002.

The first end of the latch may have any suitable configuration, e.g., length, width, shape, etc., that allows the application of force to slide the latch towards the cutout in the system controller. For example, the first end of the latch may have a square, rectangular, or semi-circular shape. Additionally, the first end of the latch may include a lip or other feature configured to help secure the latch to the system controller when locked to the controller housing of the blood flow control device. The second end of the latch may also have any suitable configuration, e.g., length, width, shape, etc., that allows it to engage the cutout and secure the blood flow control device to the system controller. Similarly, the cutout of the system controller may have any suitable size and shape to receive the first latch end.

Figure 20:
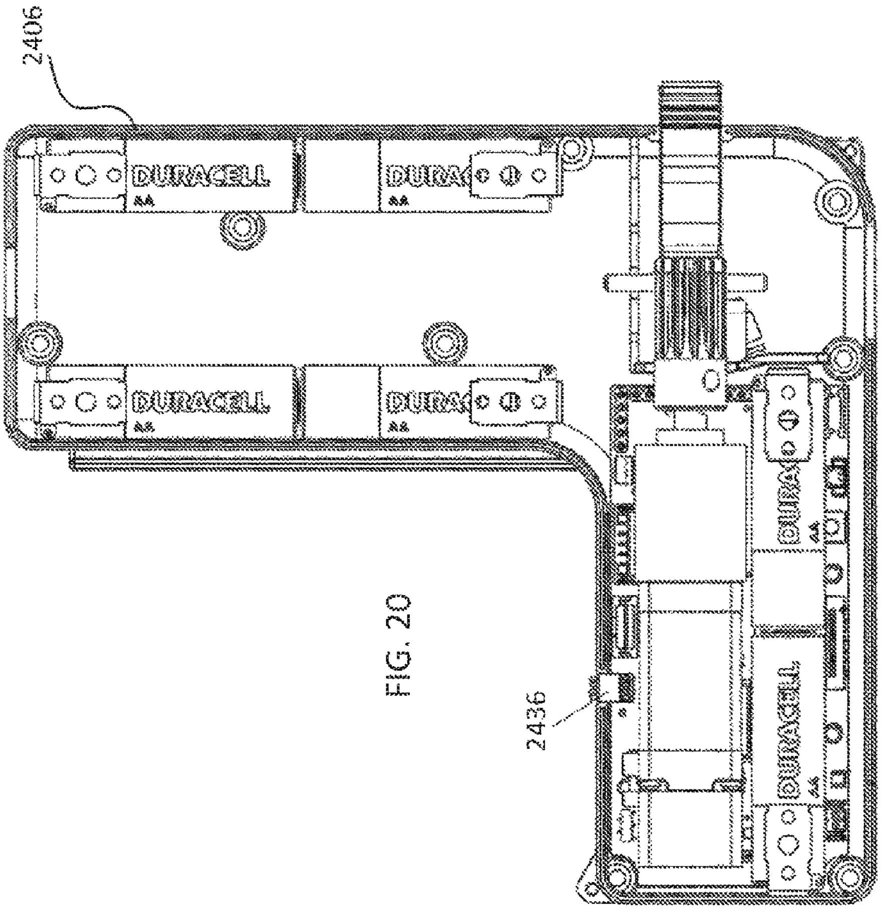
FIG. 20 illustrates a cutaway view of an exemplary variation of a system controller comprising an electrical interface.

FIG. 20 illustrates an exemplary variation of electrical interface for a system controller 2406. As discussed in FIG. 15, the system controller 2406 may be electrically coupled to the blood flow control device. In some variations, the system controller 2406 may be electrically coupled via electrical connection 2436. In some variations, the electrical connection 2436 may be a spring-based electrical connection. In other variations, the electrical connection 2436 may be a wired connection using, for example, a cable. In some variations, the electrical connection 2436 may transfer data from the blood flow control device to a PCB on the system controller 2406.

As mentioned above, the system controller 106 may be configured to control a movement of the pump 108. As described in more detail herein, the system controller 106 may be configured to operate the blood flow control system in a manual mode and an automatic mode. The system controller may include one or more user controls. For instance, the housing of the system controller 106 may include one or more buttons. Additionally or alternatively, a user interface such as a user interface operably coupled to the system controller 106 and/or a user interface communicably coupled to the device controller 112 may be configured to be a touch screen. The touch screen may include one or more buttons. In the manual mode of the controller, a user may press the one or more buttons (e.g., physical buttons on the system controller 106 and/or touchscreen buttons on the user interface) to control the movement of the pump. Pressing the buttons may control the actuator, which may in turn move the plunger of the pump 108, thereby controlling the movement of the pump 108. In the automatic mode of operation, the system controller 106 may automatically control the movement of the pump 108 by controlling the actuator based on measurements of the physiologic condition of the patient. Furthermore, the pump 108 may be releasably coupled to and removed from the system controller 106 so that at any time a user may detach the pump 108 from the system controller 106. After detaching the pump 108 from the system controller 106, the user may manually actuate the pump 108 by moving the plunger of the pump by hand to change a volume of the expandable member.

Figure 16:
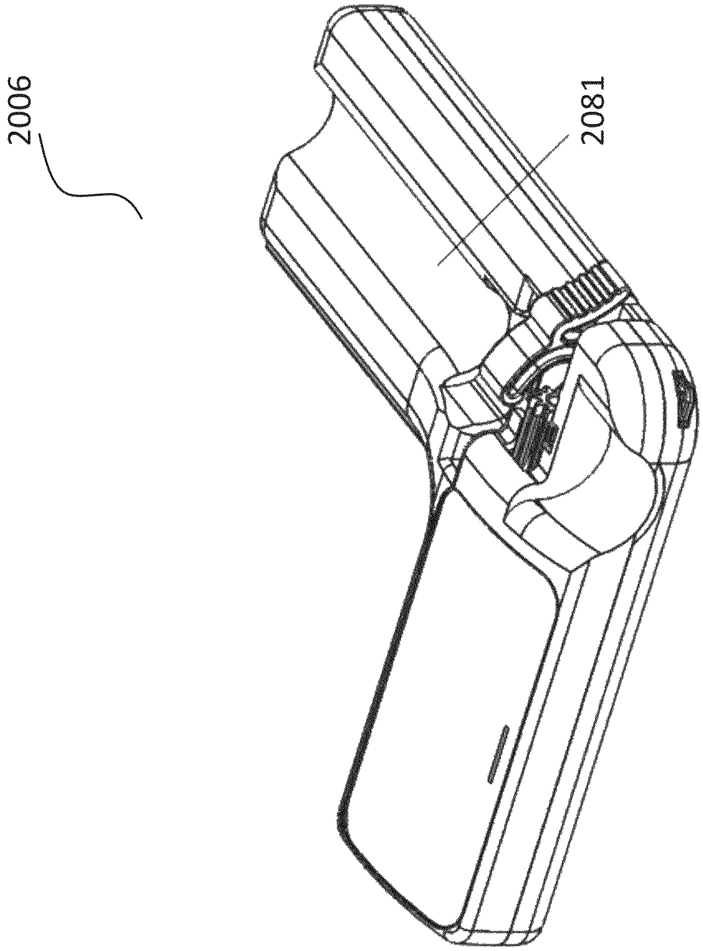
FIG. 16 illustrates an exemplary variation of a system controller of a blood flow control system.

FIG. 16 is an exemplary variation of a system controller 2006 (e.g., structurally and/or functionally similar to system controller 106 in FIG. 1A and FIG. 1B). In some variations, the system controller 2006 may include several hardware components. The components may be capable of meeting performance requirements for an endovascular procedure. For instance, the components of the system controller 2006 may meet the performance requirements for at least 4 hours. In other words, the battery life of the system controller 2006 may be at least 4 hours. In some variations, the system controller 2006 may have a reduced form factor. For example, the system controller 2006 may be designed to have a compact shape. In some variations, the system controller 2006 may be reverse L-shaped. In some variations, the system controller 2006 may have any suitable compact shape such as L-shape, square shape, etc. As discussed in FIG. 15, the system controller 2006 may include features, elongate channels, protrusions, and/or the like to mechanically couple the system controller 2006 to the blood flow control device.

Reverting back to FIG. 16, a housing of the system controller 2006 may include a recessed portion 2081 (e.g., a contoured portion) sized and shaped to receive the pump. For example, in some variations, recessed portion may be or may comprise a cavity or chamber (e.g., a concave cavity formed within the housing) configured to receive the cylindrical body of the syringe. In some variations, the recessed portion may comprise a shape that corresponds to the shape of cylindrical body and/or plunger, such that the cylindrical body and/or plunger are easily received and held within the recessed portion. A portion of the cylindrical body of the pump may be positioned and/or supported by the recessed portion 2081. In some variations, an opening and/or other cavity (not shown in FIG. 16) within the housing of the controller may comprise an actuator (e.g., circular gear). The actuator may engage with an actuating element (e.g., linear gear) on a plunger of the pump. Accordingly, moving the circular gear may cause the linear gear to move, thereby causing the plunger to move within the cylindrical body. In some variations, the circular gear may be actuated by a stepper motor. In some variations, a gearbox may couple the stepper motor to the circular gear.

In some variations, the housing of the system controller 2006 may include a lever for coupling the pump (e.g., locking) to the housing of the system controller 2006. The lever may be configured to maintain an alignment (e.g., center-to-center distance) between the actuator (e.g., circular gear) of the system controller and the actuating element (e.g., linear gear) of the pump and/or may be configured to lock the pump to the housing of the system controller 2006.

Figure 17A:
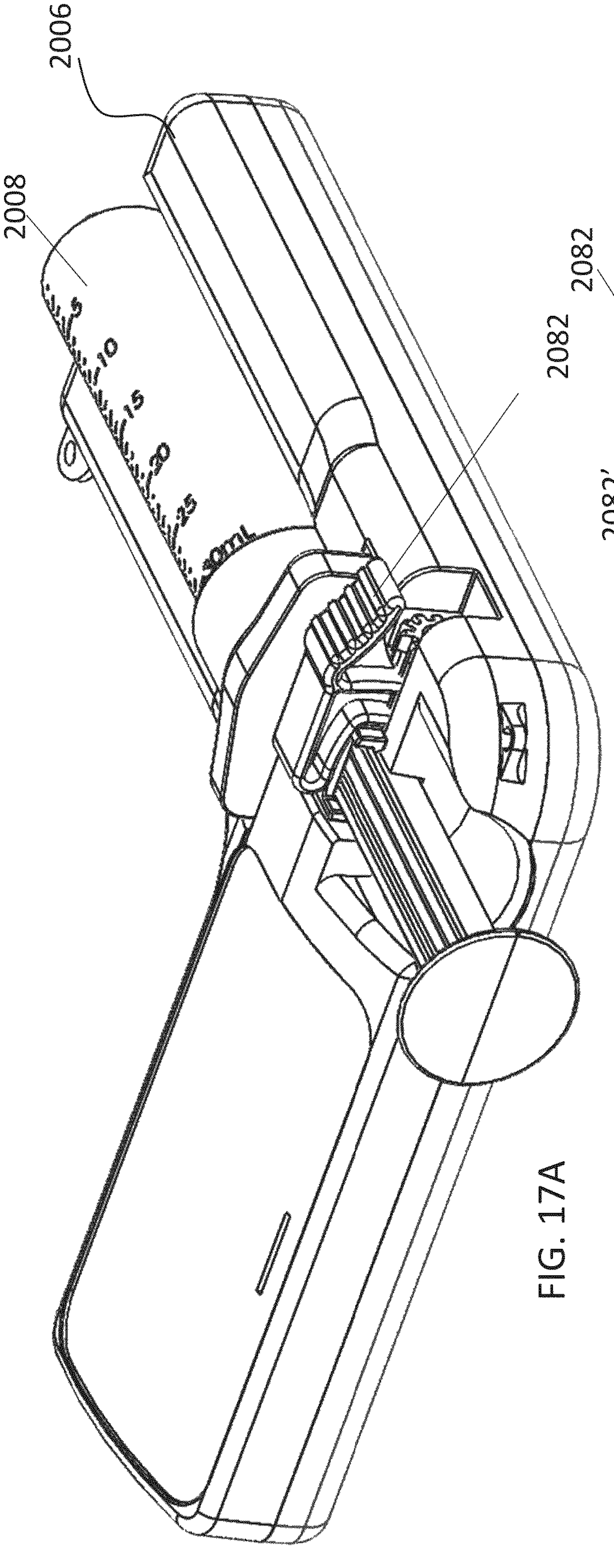
FIG. 17A illustrates a front view of an exemplary variation of a lever of a system controller in a closed configuration.
Figure 17B:
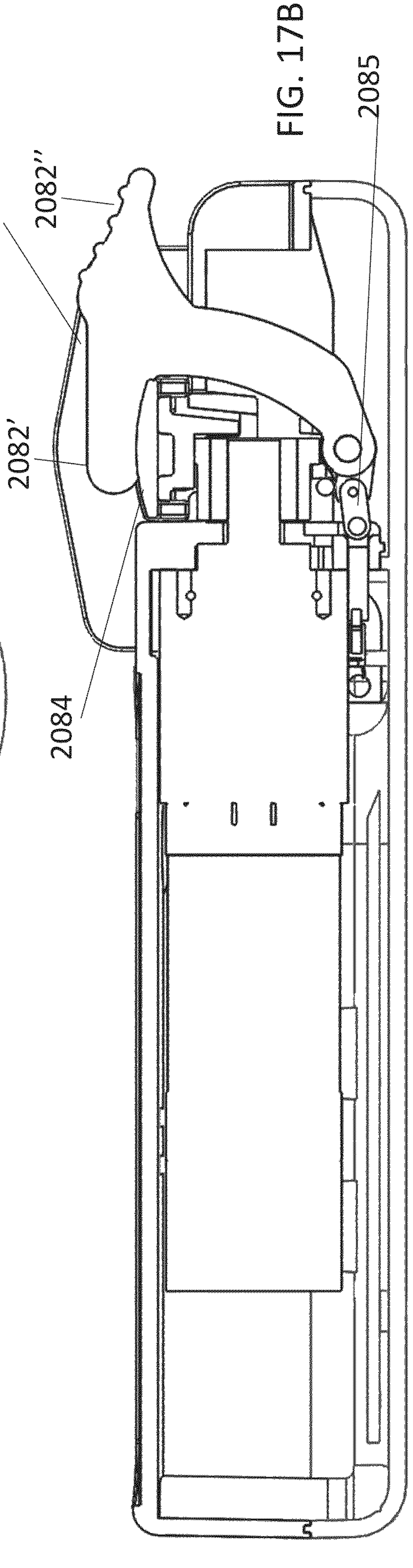
FIG. 17B illustrates a cross-sectional view of an exemplary variation of a lever of a system controller in a closed configuration.

FIG. 17A illustrates a front view and FIG. 17B illustrates a cross-section view of an exemplary variation of a lever 2082 in a closed configuration. As seen in FIG. 17A, the cylindrical body of the pump 2008 fits into the recessed portion of the housing of the system controller 2006 and the pump 2008 may be locked to the system controller 2006 using the lever 2082 (e.g., flip lever). A first end 2082' of the lever 2082 may engage with a mating feature 2084 on the pump 2008. For example, the lever may include indentations 2082' that may latch over an edge feature 2084 on the pump 2008 (e.g., on the elongate member of the pump). This may prevent accidental release of the pump 2008 due to knocking and/or jostling. A second opposite end 2082" may include ridge shaped features to enable gripping the lever. For instance, a user may be able to transition the lever from closed configuration to an open configuration by holding the second end 2082" and applying force on the ridge shaped features. The lever 2082 may be designed to be an over center latch in the closed configuration. Accordingly, any force acting to push the pump 2008 out of the housing of the system controller 2008 may only draw the lever tighter, thereby tightly locking the pump 2008 to the system controller 2006. Additionally, any force acting to push the pump 2008 out of the housing of the system controller 2006 may draw the lever tighter, thereby causing the lever to maintain a position of the pump 2008 relative to the housing of the system controller 2006. In the closed configuration, the lever 2082 maintains an alignment between the linear gear on the pump 2008 and a circular gear positioned at least partially within the housing of the system controller 2006. For example, the lever 2082 may maintain a predetermined distance from a center of the linear gear to a pitch height of the circular gear. As discussed above, maintaining the distance from the pitch height of the linear gear to the center of the circular gear may improve precision. In some variations, the predetermined distance may be between a range of 2 mm and 10 mm. In some variations, the predetermined distance may be 7.2 mm.

Figure 18A:
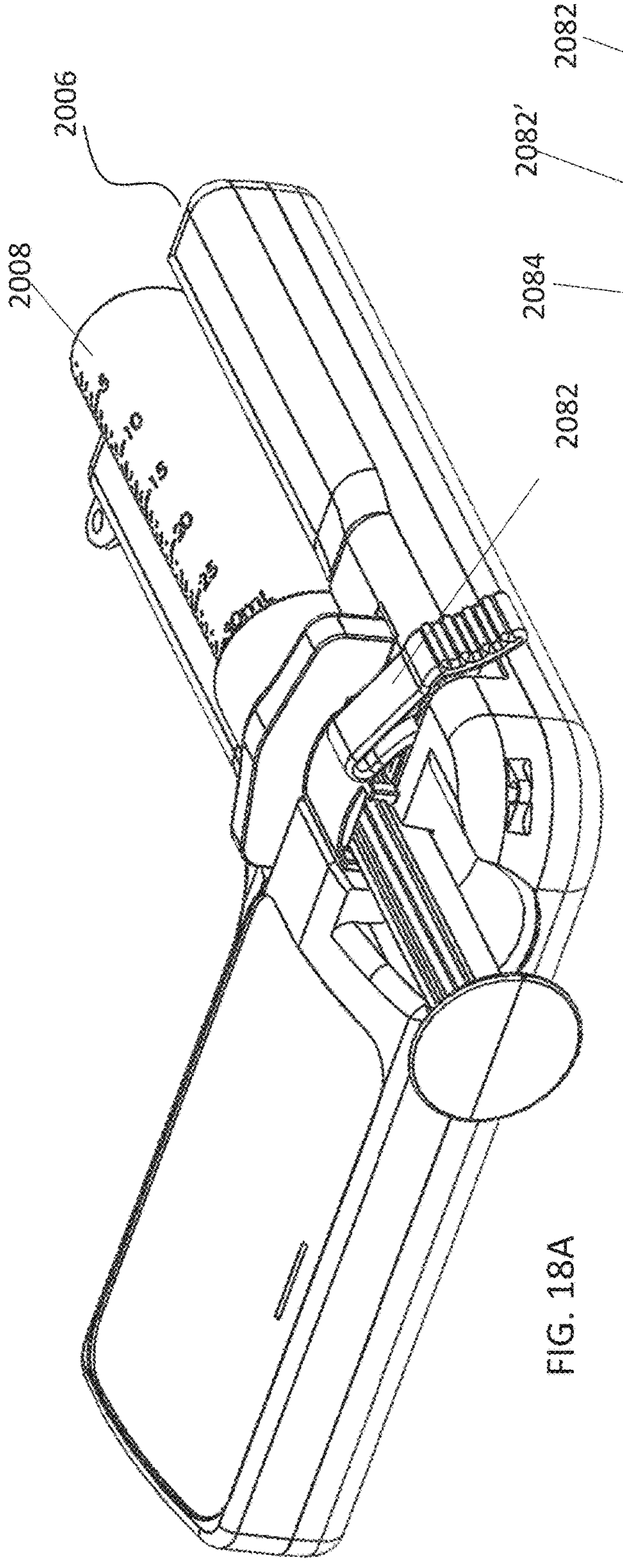
FIG. 18A illustrates a front view of an exemplary variation of a lever of a system controller in an open configuration.
Figure 18B:
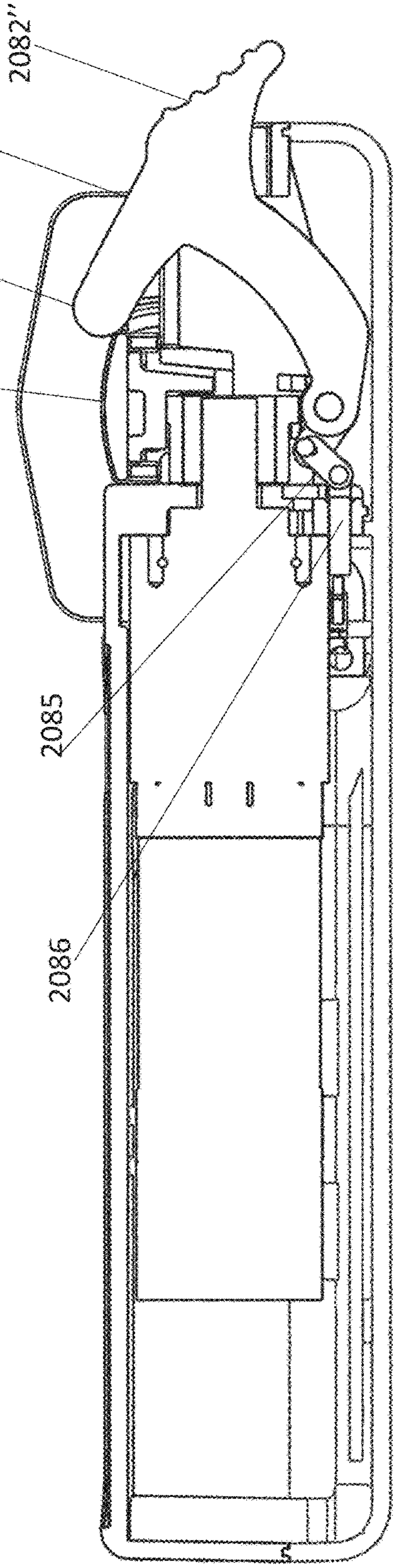
FIG. 18B illustrates a cross-sectional view of an exemplary variation of a system controller in an open configuration.

FIG. 18A illustrates a front view and FIG. 18B illustrates a cross-sectional view of an exemplary variation of a lever 2082 in an open configuration. As discussed above, the lever may transition from the closed configuration to an open configuration, thereby allowing for removal of the pump from the housing of the system controller. In the open configuration, the second end 2082" of the lever may be pulled away from the housing of the controller. In other words, the lever may be positioned away from the housing of the controller. When the lever is pulled away from the housing of the controller, the lever may disengage from the pump. In some variations, the lever 2082 may be biased towards the open configuration. For example, the location of the center of mass of the lever 2082 may bias the lever toward the open configuration. The lever 2082 may be configured to pivot around the linkage pivot point 2085 that couples the lever 2082 to the housing of the system controller 2006. The center of mass of the lever 2082 may have moment about a linkage pivot point 2085 that may bias the lever 2082 open.

Figure 17C:
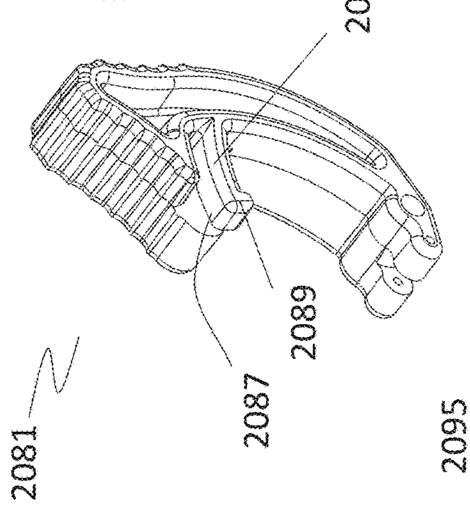
FIGS. 17C-17G illustrate another exemplary variation of a lever including an arm configured to help secure a syringe pump to the system controller.
Figure 17E:
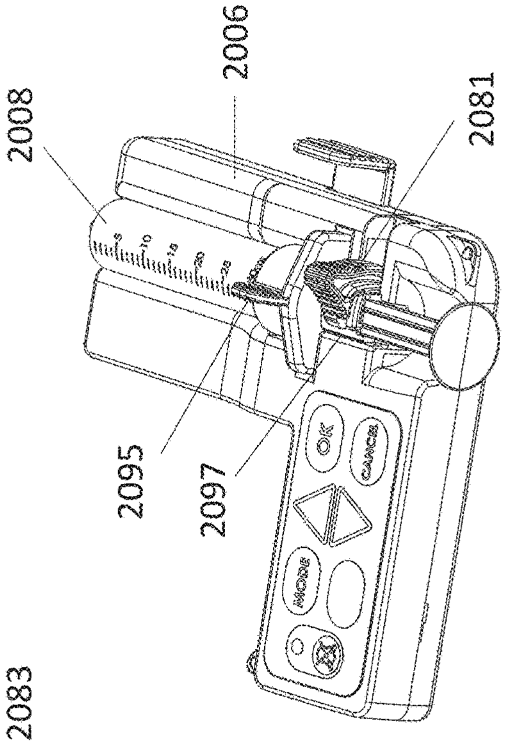
Figure 17D:
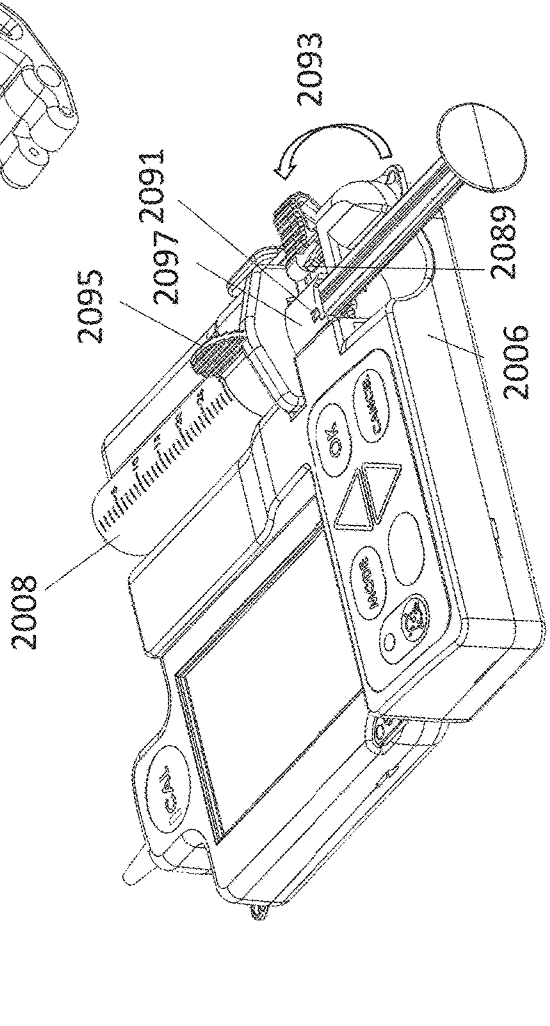
Figure 17F:
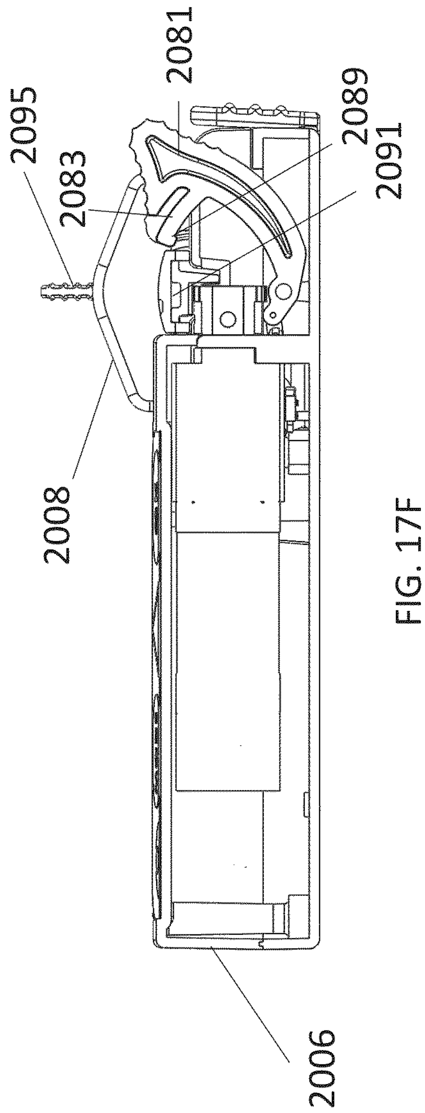
Figure 17G:
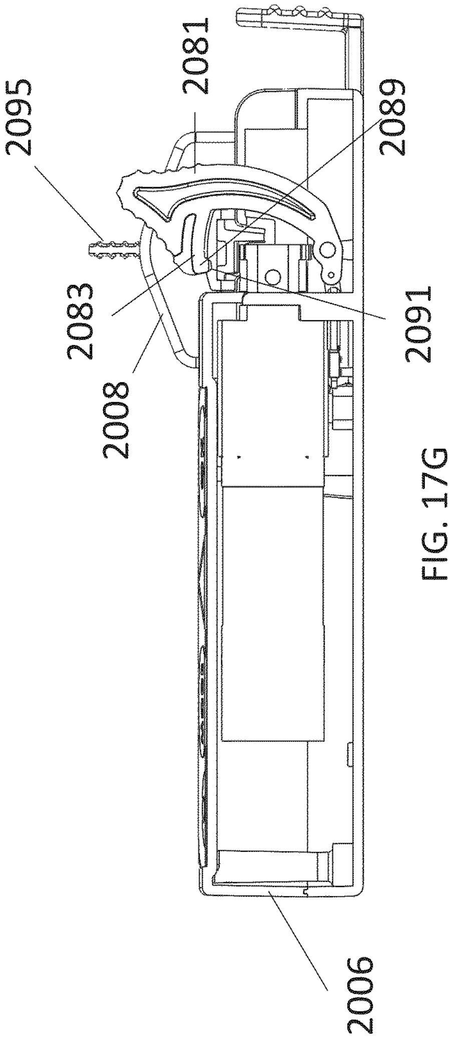

In another variation, the lever 2082 for coupling (e.g., locking) the housing of the system controller 2006 to the pump 2008 may further include an arm 2083, as shown in FIGS. 17C to 17F. The arm 2083 may extend from the inside surface of the lever 2082 and may provide additional resistance to moving the lever 2082 out of the locked position to thus help prevent accidental unlocking of the pump 2008. FIG. 17C provides an enlarged view of the lever 2082 including an arm 2083. The arm 2083 may have a distal end 2087 including a tooth 2089. As shown in FIGS. 17D and 17E, the tooth 2089 may be configured to mate (e.g., snap fit) with a corresponding structure (e.g., opening 2091) on the pump 2008 (e.g., the pump sleeve 2097) when the lever 2082 is rotated (e.g., in the direction of arrow 2093) to the closed position. In some variations, the pump 2008 may also include a fin 2095 to aid removing the pump 2008 from the housing of the system controller 2006. The fin 2095 may or may not have ribs or other texturing that may help increase the grip on the fin 2095 when pulled. FIGS. 17F and 17G provide cross-sectional views of FIGS. 17D and 17E, respectively.

The system may be configured to determine when the pump is positioned within the system controller housing and/or locked within position for use with the system controller. For example, in some variations, the system controller 2802 may be configured to determine that the pump is positioned in the housing of the system controller 2006 and/or locked to the system controller 2006 via the position of the lever 2082. For instance, when the lever 2082 is in a closed configuration, the linkage pivot point 2085 may contact and/or move (e.g., push) a switch 2086 on the system controller. Contacting and/or moving the switch 2086 may alert the system controller 2006 that the pump 2008 is present and is locked to the system controller 2006. Additionally or alternatively, the system controller 2006 may be configured to determine that the pump is positioned in the housing of the system controller 2006 and/or locked to the system controller 2006 via the position of the pump 2082. For instance, when the lever 2082 is in a closed configuration, the cylindrical body of the pump 2008 may contact and/or move (e.g., push) a switch (e.g., switch 2086) to alert the system controller 2006 that the pump is locked to the system controller 2006.

Figure 19:
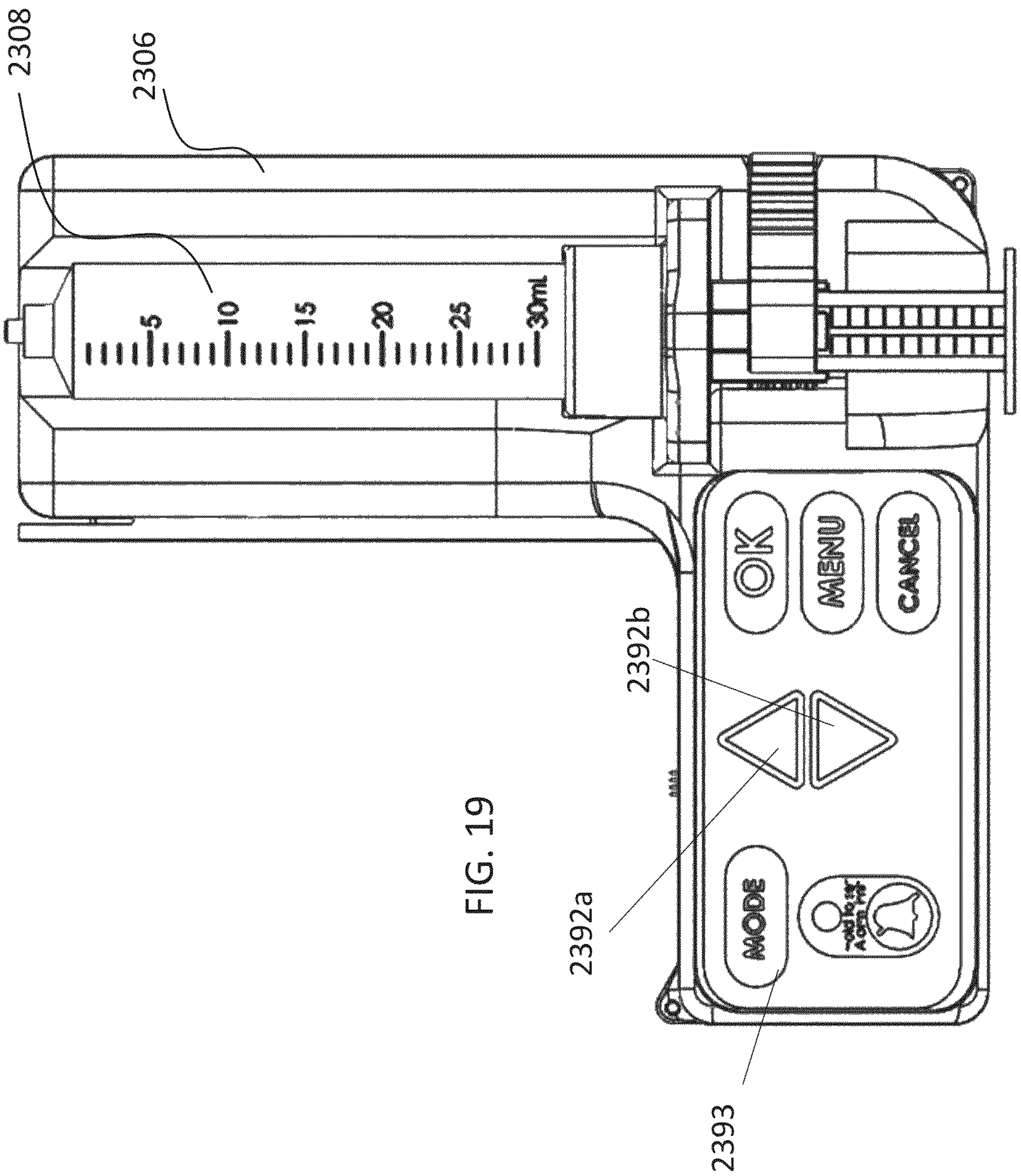
FIG. 19 illustrates an exemplary variation of a system controller comprising buttons.

FIG. 19 illustrates an exemplary variation of a system controller for operating a pump 2308. For example, in the variation depicted in FIG. 19, the user interface of the system controller 2306 may comprise a plurality of buttons. The buttons may be used to operate the pump 2308 when the pump 2308 is coupled to the system controller 2306 and the system controller 2306 is in a manual mode of operation. As discussed above, a user may operate the pump 2308 in a manual mode of operation without decoupling the pump 2308 from the system controller 2306. For example, a user may press the buttons (e.g., 2392*a*, 2392*b*, 2393, etc.) as shown in FIG. 22 to control the pump 2308 in a manual mode of operation. For instance, pressing the buttons 2392*a* and/or 2392*b* may cause an actuator (e.g., circular gear) positioned in the housing of the system controller 2306 to engage with an actuating element (e.g., linear gear) on the plunger. Additionally, pressing the buttons 2392*a* and/or 2392*b* may cause the circular gear to rotate, thereby causing the linear gear to translate. This in turn may cause the plunger to move within the cylindrical body of the pump 2308. In some variations, pressing the button 2392*a* may cause the plunger to transmit fluid out of the cylindrical body, thereby causing an inflation of the expandable member. Similarly, pressing the button 2392*b* may cause the plunger to withdraw fluid into the cylindrical body, thereby causing a deflation of the expandable member. In some variations, a user may press the button 2392*a* to actuate the pump 2008 to inject fluid into an expandable member so that a target physiologic condition may be achieved. Similarly, the user may press the button 2392*b* to reduce a volume of the expandable member. In this way, the pump 2308 may be operated in a manual mode of operation, using the system controller 2308, and without having to decouple the pump 2308 from the system controller 2306. In some variations, the mode button 2393 may allow a user to switch the system controller 2306 from the manual mode to the automatic mode and vice versa.

Although FIG. 19 illustrates "buttons" on the system controller for operating the pump, it should be readily understood that any suitable mechanism may be provided on the system controller for operating the pump. For example, the system controller may instead include a switch that may move from a first position to second position and vice versa. The first position may be indicative of automatic mode of operation and the second position may be indicative of manual mode of operation. Similarly, the system controller may include a dial with an automatic mode position and a manual mode position. As discussed above, additionally or alternatively, the blood flow control system, blood flow control device, and/or the system controller may include a user interface with a touch surface. The user interface may include capacitive buttons and/or resistive buttons for operating the pump.

Figure 21:
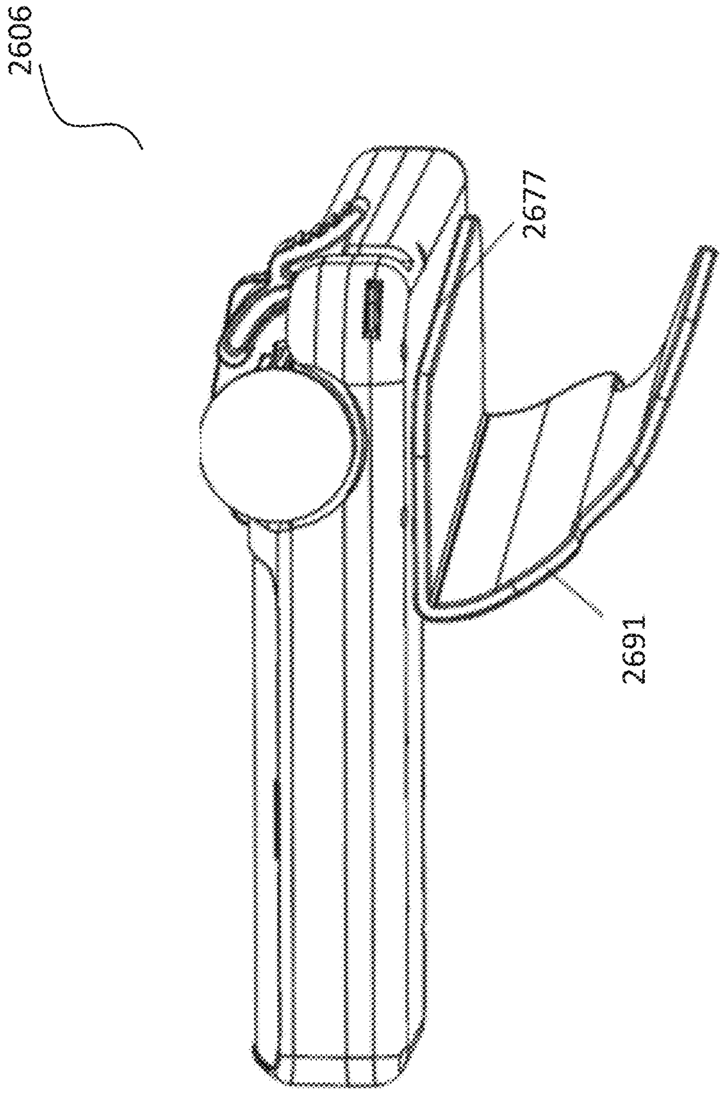
FIG. 21 illustrates an exemplary variation of a system controller including a support element.

FIG. 21 illustrates an exemplary variation of a system controller 2606 including an attachment element to provide additional support and stabilization to the blood flow control device. For example, the attachment element may be configured to couple the system controller 2606 to a patient (e.g., a patient's leg) during use. For example, the attachment element may comprise a support wedge 2691. The support wedge 2691 may include an attachment portion configured to attach the support wedge 2691 to the system controller 2606 and to a patient during use. For example, the support wedge 2691 may include an adhesive face 2677 coupled to the bottom of the system controller 2606.

Referring back to FIG. 1A, as discussed above, the system controller may comprise a motion sensor and/or a position sensor to measure a position of a plunger of a syringe pump and/or a movement of the plunger of the syringe pump (including, but not limited to, an actuation element such as linear gear on an elongate member of the plunger). Additionally or alternatively, the device controller 112 may comprise a motion sensor and/or a position sensor communicably coupled to the pump 108. The position sensor may measure a position of the plunger of a syringe pump, while the motion sensor may measure motion of the plunger of the syringe pump. The position and/or motion of the plunger may optionally be used to infer the amount of fluid that has been delivered to and/or removed from the expandable member 110, or may otherwise be used to control actuation of the syringe pump.

Additionally or alternatively, the system and/or device controller 112 may comprise a motion sensor, a position sensor, and/or a contact sensor to measure a position and/or motion of another component of the system, such as, for example, an actuation mechanism for the pump (e.g., a motor configured to actuate the syringe), the actuator (e.g., circular gear), or another gear or component in the system. In some variations, the motion sensors may include encoders, such as, for example, magnetic encoders, optical encoders, etc. In variations comprising encoders, the encoders may monitor movement of the component, e.g., the motor, the circular gear, the linear gear or other portion of the plunger, etc., and the movement may be used to control actuation of the syringe and/or to determine the amount of inflation and/or deflation in the expandable member. More specifically, for example, if the syringe is actuated using a motor, the encoder may monitor movement of the motor, and the motor's movement may be used to determine the amount of inflation and/or deflation in the expandable member 110 and/or may be used to control actuation of the syringe.

As also described above, the blood flow control systems (e.g., the blood flow control device) may comprise proximal and distal sensors, which may be electronically coupled to the system controller 106. The system controller 106 may comprise a housing. The housing may contain a number of electronic components, such as, for example, a biasing circuit, an amplifier, a filter, and an Analog-to-Digital Conversion (ADC) circuit. The ADC circuit may output the readings obtained from the sensors (e.g., the proximal sensor and the distal sensor), thereby indicating a physiologic condition of the patient. For example, in some variations, the proximal sensor and the distal sensor may each include three connection wires—a power wire and two output wires. The output wires may be connected to the biasing circuit and the power wire. The biasing circuit may provide power to the power wire and appropriate resistance to the two output wires. The two output wires may be coupled to the amplifier which may amplify the differential voltage created across the two output wires. The amplifier may be coupled to the filter which may reduce high frequency and/or low frequency noise from the output of the amplifier. The output of the filter may be coupled to the Analog-to-Digital Conversion (ADC). The output of the ADC may be at a variety of rates and sample sizes indicating a physiologic condition of the patient.

Accordingly, the sensor readings from the proximal sensor and the distal sensor may be extracted directly at the system controller 106. In some variations, the expandable member pressure sensor, the barometer, and optionally the flow sensor may transmit sensor data directly to the system controller 106. The data from the sensors in the system may be collected continuously or intermittently and may be collected over a defined period of time. In some variations, the data from the proximal sensor and the distal sensor may be collected continuously, such as for example, every 3 seconds, 4 seconds, 5 seconds, 6 seconds, 7 seconds, 8 seconds, 9 seconds, or 10 seconds (including all values and sub-ranges therein, such as, for example, between about 3 second and about 6 second, about 4 second and about 6 second, or between about 5 second or about 6 second). In some variations, the data from the proximal sensor and the distal sensor may be collected every 5 seconds at 200 Hz.

In some variations, data may be collected from the expandable member sensor continuously such as, for example, every 3 seconds, 4 seconds, 5 seconds, 6 seconds, 7 seconds, 8 seconds, 9 seconds, or 10 seconds (including all values and sub-ranges therein, such as, for example, between about 3 second and about 6 second, about 4 second and about 6 second, or between about 5 second or about 6 second).

In some variations, data from the sensors may be analyzed over a discrete period of time. For instance, the data may be analyzed for example, every 3 seconds, 4 seconds, 5 seconds, 6 seconds, 7 seconds, 8 seconds, 9 seconds, or 10 seconds (including all values and sub-ranges therein, such as, for example, between about 3 seconds and about 6 seconds, about 4 seconds and about 6 seconds, or between about 5 seconds or about 6 seconds). In some variations, the actuation mechanism to the pump 108 may be actuated by a motor, such as a stepper motor (e.g., directly or via an actuator and actuation element as described in more detail herein). In such variations, the data may be analyzed based on the motion of the stepper motor (e.g., 1300 steps per second) and/or based on the sequence of the movement of the motor (e.g., between 25-2000 milliseconds).

The system controller 106 may include one or more processors (e.g., CPU). The processor(s) may be any suitable processing device configured to run and/or execute a set of instructions or code, and may include one or more data processors, image processors, graphics processing units, digital signal processors, and/or central processing units. The processor(s) may be, for example, a general purpose processor, a Field Programmable Gate Array (FPGA), an Application Specific Integrated Circuit (ASIC), and/or the like. The processor(s) may be configured to run and/or execute application processes and/or other modules, processes and/or functions associated with the blood flow control system 100.

In some variations, the system controller 106 may run and/or execute application processes and/or other modules. These processes and/or modules when executed by a processor may be configured to perform a specific task. These specific tasks may collectively enable the system controller 106 to automatically operate and control the blood flow control system 100 while detecting errors and responding to the errors. Specifically, these specific tasks may enable the system controller 106 to detect errors and automatically adjust inflation and/or deflation of the expandable member 110 accordingly.

Generally, the processor (e.g., CPU) described here may process data and/or other signals to control one or more components of the system. The processor may be configured to receive, process, compile, compute, store, access, read, write, and/or transmit data and/or other signals. In some variations, the processor may be configured to access or receive data and/or other signals from one or more of a sensor (e.g., proximal sensor, distal sensor, expandable member sensor, etc.) and a storage medium (e.g., memory, flash drive, memory card). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may be, for example, a general-purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Generally, the blood flow control systems described herein (e.g., the system controller and/or device controller) may comprise a memory configured to store data and/or information. In some variations, the memory may comprise one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with a blood flow control device, such as signal waveform generation, expandable element control, data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. In some variations, the system controller 106 and the device controller 112 may be integrated into a single controller.

Measurements Determined by the System Controller

Below are non-limiting examples of measurements that may be determined by the system controller 106 based on sensor data from one or more of the proximal sensor, the distal sensor, the expandable member sensor, the barometer, and the flow sensor. While described below in relation to the system controller 106, it should be appreciated that one or more of the measurements may be determined by the device controller 112.

Proximal Average Pressure

The proximal average pressure measurement includes one or more of proximal systolic pressure, proximal diastolic pressure, and current proximal mean arterial pressure (PMAP). In some variations, PMAP may be the arithmetic mean of pressure samples received from the proximal sensor over a time window. For instance, as a non-limiting example, if 800 pressure samples were captured at 200 Hz over a 4 second time window, then the PMAP may be the arithmetic mean of the 800 samples. In some variations, proximal systolic pressure may be the average of peaks in pressure samples collected over the time window. For instance, if three full heartbeats appeared in the 4 second time window, the proximal systolic pressure may be the arithmetic mean of the three peak values. In some variations, proximal diastolic pressure may be the average of the valleys in the pressure samples collected over the time window. For instance, the proximal diastolic pressure may be the arithmetic mean of the three valley values that may have appeared in the 4 second time window.

It should be readily apparent that the proximal average pressure may be calculated in any suitable manner. For instance, instead of receiving samples over a time window, the proximal average pressure may be calculated based on samples received for one or more heartbeats, such as each heartbeat, two heartbeats, three heartbeats, etc. Similarly, proximal average pressure may be the median, mode, etc., of pressure samples received over a time window and/or during one or more heartbeats.

Proximal Pressure Pulsatility

Proximal Pressure pulsatility may indicate changes to the proximal systolic pressure, proximal diastolic pressure, and/or PMAP over a defined time window. For example, proximal pressure pulsatility may be an absolute difference of each of/combination of proximal systolic pressure, proximal diastolic pressure, and/or PMAP over a defined period of time. For instance, proximal pressure pulsatility may be the arithmetic difference between the proximal systolic pressure and the proximal diastolic pressure. In some variations, proximal pressure pulsatility may be a ratio of each of/a combination of proximal systolic pressure, proximal diastolic pressure, and/or PMAP over a time window.

Distal Average Pressure

The distal average pressure measurement includes one or more of distal systolic pressure, distal diastolic pressure, and current distal mean arterial pressure (DMAP). In some variations, DMAP may be the arithmetic mean of pressure samples received from the distal sensor over a time window. For instance, as a non-limiting example, if 800 pressure samples were captured at 200 Hz over a 4 second time window, then the DMAP may be the arithmetic mean of the 800 samples. In some variations, distal systolic pressure may be the average of peaks in pressure samples collected over the time window. For instance, if three full heartbeats appeared in the 4 second time window, the distal systolic pressure may be the arithmetic mean of the three peak values. In some variations, distal diastolic pressure may be the average of the valleys in the pressure samples collected over the time window. For instance, the distal diastolic pressure may be the arithmetic mean of the three valley values that may have appeared in the 4 second time window.

It should be readily apparent that the distal average pressure may be calculated in any suitable manner. For instance, instead of receiving samples over a time window, the distal average pressure may be calculated based on samples received for one or more heartbeats, such as each heartbeat, two heartbeats, three heartbeats, etc. Similarly, distal average pressure may be the median, mode, etc., of pressure samples received over a time window and/or during one or more heartbeats.

Distal Pressure Pulsatility

Distal pressure pulsatility may indicate changes to the distal systolic pressure, distal diastolic pressure, and/or DMAP over a defined time window. For example, distal pressure pulsatility may be an absolute difference of each of/combination of distal systolic pressure, distal diastolic pressure, and/or DMAP over a defined period of time. For instance, distal pressure pulsatility may be the arithmetic difference between the distal systolic pressure and the distal diastolic pressure. In some variations, distal pressure pulsatility may be a ratio of each of/a combination of distal systolic pressure, distal diastolic pressure, and/or DMAP over a time window.

It should be readily understood that "blood pressure measurement" as referred to herein may include one or more of, or a combination of one or more of, proximal systolic pressure, proximal diastolic pressure, PMAP, proximal average pressure, proximal pressure pulsatility, distal systolic pressure, distal diastolic pressure, DMAP, distal average pressure, and distal pressure pulsatility.

Expandable Member Pressure

The expandable member pressure measurement may indicate the pressure of fluid and/or compressed gas in the expandable member 110. The expandable member pressure measurement may be determined from the sensor data obtained from the expandable member sensor.

Expandable Member Volume

The expandable member volume measurement may indicate the amount (e.g., a volume) of fluid and/or compressed gas that may have been added or removed from the expandable member 110. In some variations, the expandable member volume may be determined from the encoder data (e.g., magnetic encoder, optical encoder, etc.) that may measure the movement of the actuation mechanism to the pump 108 (e.g., a stepper motor).

Expandable Member Mean Pressure

The Expandable Member Mean Pressure may be the arithmetic mean of pressure samples obtained from the expandable member pressure sensor over a time period. For instance, the expandable member sensor may obtain expandable member pressure samples over a period of time. The expandable member mean pressure may be the arithmetic mean of these pressure samples over that period of time. As a non-limiting example, if 800 pressure samples were captured at 200 Hz over a 4 second time window, then the expandable member mean pressure may be the arithmetic mean of the 800 samples.

Blood Flow Rate

The blood flow rate measurement may indicate the amount or rate of blood flowing past the expandable member 110. In some variations, the blood flow rate may be determined from the sensor data obtained from the flow sensor. Alternatively, the blood flow rate may be determined based on various other measurements such as proximal average pressure, distal average pressure, expandable member pressure, expandable member volume, and loss of pulsatility or change in shape of the waveforms reported by the distal average pressure.

Blood Flow State

The blood flow state may indicate the relative occlusion of the blood vessel provided by the blood flow control device (e.g., expandable member). Put another way, the blood flow state may indicate the level of blood flow in the blood vessel (e.g., high flow or low flow) while the blood flow control device is in use. Thus, the blood flow state may indicate whether there is full occlusion, partial occlusion, or no occlusion in the blood vessel. In some variations, the systems and methods described herein may utilize two blood flow states: occlusion and flow. The blood flow state may be determined based on a combination of sensor data including but not limited to expandable member pressure, a rate of change the expandable member sensor data, the pulsatility or cyclical change in the expandable member pressure, expandable member volume, a comparison of the expandable member volume at various points in time, and loss of pulsatility or change in shape of the waveforms reported by the distal average pressure.

In variations in which an occlusion state and a flow state are utilized, the system may determine which state is applicable by comparing the estimated blood flow rate to a threshold. For instance, when the blood flow rate is below the threshold, the blood flow state may be designated to be occlusion, and when the blood flow rate is above the threshold, the blood flow state may be designated to be Flow. In another variation, the system may determine the blood flow state using a difference between two blood pressure measurements, such as, for example, distal systolic pressure and DMAP. This difference may be compared to one or more threshold values, and the blood flow state may be designated to be occlusion if the pressure difference is below a threshold value and may be designated to be flow if the pressure difference is above the same, or a different, threshold value. For example, in one variation, the blood pressure measurements utilized to determine blood flow state may be distal systolic pressure and DMAP. In this variation, if the difference between distal systolic pressure and DMAP is less than about 2 mm Hg, the blood flow state may be designated as occlusion. However, if the difference between the distal systolic pressure and DMAP is greater than about 4 mm Hg, the blood flow state may be designated as flow. If the difference between the distal systolic pressure and DMAP is between about 2 mm Hg and about 4 mm Hg, the blood flow state may optionally be designated as a third state, such as, for example, low flow. Similarly, the distal blood pressure pulsatility (distal systolic pressure minus distal diastolic pressure) may be divided by the DMAP to create a metric to estimate distal flow, or the distal MAP minus the distal diastolic pressure or the distal MAP divided by the distal diastolic pressure may be used. In another variation, the blood pressure measurements utilized to determine blood flow state may be distal diastolic pressure and DMAP. In this variation, if the difference between DMAP and the distal diastolic pressure is less than a threshold value, the blood flow state may be designated as occlusion. For example, in some variations, if the difference between DMAP and the distal diastolic pressure is between 0.1 and 5 the blood flow state may be designated as occlusion. When the blood flow rate or blood flow state is not determined, the blood flow state may be designated as indeterminate or/or an alert may be provided to a user to check for occlusion.

In some variations, as mentioned above, additional states may be designated for the blood flow state. For example, instead of two states (occlusion and flow) there may be several additional states to indicate different levels of flow, such as, for example, high flow and/or low flow. These additional states may be determined using thresholds as described above with respect to the occlusion and flow states.

In some variations, the blood flow control system 100 may include a timer to determine the elapsed time at different blood flow states. For example, the amount of time in each blood flow state may be measured and/or recorded by the blood flow control system 100 and reported to a user via the user interface.

Total Elapsed Time

The total elapsed time may indicate the elapsed time from the start of use of the blood flow control system 100. For instance, the total elapsed time may indicate the elapsed time from the point at which the blood flow control system 100 is turned on. Alternatively, the total elapsed time may indicate the elapsed time since the start of a therapeutic procedure using the blood flow control system 100. For example, the total elapsed time may indicate the elapsed time from the point at which the expandable member 110 is advanced into a blood vessel of a patient.

Total Time at Occlusion

The total time at occlusion may indicate the amount of time the blood flow state may be designated as occlusion. In some variations, if the blood flow state is designated as occlusion multiple times during a single procedure, the total time at occlusion may be the cumulative total of each time the blood flow state is designated as occlusion. In some variations, each time the blood flow state is designated as occlusion, the total time at occlusion may be indicative of the amount of time spent in the occlusion state. For example, if the system detects a blood flow state of occlusion for 3 minutes, followed by a blood flow state of flow for 3 minutes, followed by a blood flow state of occlusion for 2 minutes, the system will calculate the total time at occlusion to be 5 minutes.

Total Time not at Occlusion

The total time not at occlusion may indicate the amount of time the blood flow state may not be designated as occlusion. In some variations, if the blood flow state is designated as occlusion multiple times during a single procedure, the total time not at occlusion may be the cumulative total of each time the blood flow state is not designated as occlusion. In some variations, each time the blood flow state is not designated as occlusion, the total time spent in that state (i.e., not the occlusion state) may be indicative of the total time not at occlusion. For example, if the system detects a blood flow state of occlusion for 3 minutes, followed by an indeterminate state for 2 minutes, followed by a flow state for 3 minutes, the system will calculate the total time not at occlusion to be 5 minutes.

Communication Device or Module

In some variations, the system controller 106 may include at least one communication device or module (e.g., communication module 126 as shown in FIG. 2), such as a wireless communication module to communicate with one or more other devices. For example, the communication module may be configured to communicate data (e.g., sensor data, target blood pressures, target blood pressure ranges, state of the blood flow control system, such as internal temperature of blood flow control system, battery charge level of the blood flow control system, time of day, and/or properties of the blood flow control system, such as hardware and firmware revision number of the blood flow control system, system capabilities, etc.) and/or determinations or calculations made based on the data (e.g. errors, physiologic states, clinical decision support), to one or more devices, such as, for example, an external computer, a mobile device (e.g., a smartphone), a tablet, or the like. The communication device may comprise a network interface configured to connect the blood flow control device to another device or system (e.g., Internet, remote server, database) by wired or wireless connection. In some variations, the blood flow control device and/or system may be in communication with other devices (e.g., cell phone, tablet, computer, smart watch, and the like) via one or more wired and/or wireless networks. In some variations, the network interface may comprise one or more of a radiofrequency receiver/transmitter, an optical (e.g., infrared) receiver/transmitter, and the like, configured to communicate with one or more devices and/or networks. The network interface may communicate by wires and/or wirelessly with one or more of the blood flow control device, system controller 106, network, database, and server.

The network interface may comprise RF circuitry configured to receive and/or transmit RF signals. The RF circuitry may convert electrical signals to/from electromagnetic signals and communicate with communication networks and other communication devices via the electromagnetic signals. The RF circuitry may comprise well-known circuitry for performing these functions, including but not limited to an antenna system, an RF transceiver, one or more amplifiers, a tuner, one or more oscillators, a mixer, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communication (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

The communication device or module may include a wireless transceiver that is integrated into the system controller 106. However, the blood flow control system may additionally or alternatively include a communication module that is separate from the system controller 106.

User Interface

In some variations, the blood flow control system 100 may include a user interface communicably coupled to the system controller 106 and/or the device controller 112. In some variations, the user interface may be a display on the device controller 112 and/or on the system controller 106, such that the device controller 112 may be communicably coupled to the system controller 106, or vice versa. Additionally or alternatively, the user interface may be a display on any suitable computing device (e.g., computer, smartphone, tablets, etc.) communicably coupled to the system controller 106, via, e.g., the communication device or module described herein.

In some variations, the user interface may comprise an input device (e.g., touch screen) and output device (e.g., display device) and be configured to receive input data from one or more of the blood flow control device 104, communications device, system controller 106, pump 108, and the sensor(s). For example, user control of an input device (e.g., keyboard, buttons, touch screen) may be received by the user interface and may then be processed by the system controller 106 for the user interface to output a control signal to the system controller 106, blood flow control device 104, and/or pump 108. Some variations of an input device may comprise at least one switch configured to generate a control signal. For example, an input device may comprise a touch surface for a user to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio data and recognize a user voice as a control signal.

A haptic device may be incorporated into one or more of the input and output devices to provide additional sensory output (e.g., force feedback) to the user. For example, a haptic device may generate a tactile response (e.g., vibration) to confirm user input to an input device (e.g., touch surface). As another example, haptic feedback may notify that user input is overridden by the pulsed electric field device.

In some variations, a user may input target value, target range, expected value, expected range, threshold value, threshold range and/or the like for various sensor data via the user interface. For instance, a user may input target/expected/threshold values associated with proximal systolic pressure, proximal diastolic pressure, PMAP, distal systolic pressure, distal diastolic pressure, DMAP, expandable member pressure, expandable member volume, etc. via the user interface.

In some variations, the user interface may display to the user blood flow state, graphs of one or more pressure waveforms, proximal pressure, distal pressure, expandable member volume, errors, etc. to the user. In some variations, the user interface may display at least one alert to the user. The alerts may be visual prompts such as text, icons, a combination thereof, etc. Additionally or alternatively, the input data, blood flow state, alert, graphs, etc., may be displayed on the user interface via audio prompts such as tones, spoken words, a combination thereof, etc. In some variations, the user interface may include display, such as a liquid crystal display (LCD) panel, a light emitting diode (LED) array, E-link gateway, or other means for displaying numbers, letters, graphs, and/or icons. In some variations, the user interface may include an audio output such as an audio speaker, that produces single tones, sequences of tones, or enunciated messages.

In some variations, errors detected and alerts transmitted by the system controller (described further below) may be ranked and categorized by level of importance (e.g., how harmful the error may be to the efficacy of the blood flow control system and/or the therapeutic procedure) and/or urgency, such as, for example, as high priority alerts, medium priority alerts, and low priority alerts. In some variations, alerts with different importance levels and/or urgency (e.g., high priority alerts, medium priority alerts, and low priority alerts) may be displayed and/or transmitted via the user interface differently. For instance, a high priority alert may be displayed and/or transmitted via the user interface in a manner so as to catch the attention of the user. For example, an array of red lights may continuously blink via the user interface to indicate a high priority alert. Additionally or alternatively, a loud audio tone, or a sequence of audio tones, may be transmitted via the user interface that may indicate the high priority alert. In contrast, for example, low priority alerts may appear as text on a visual display without an array of colored blinking lights, such as red lights.

In some variations, the syringe pumps described herein may also include a low power display. The low power display may be large enough to allow the user to view information about the state of the system, and to implement changes of settings. Various display techniques may be considered, including LCDs and OLEDs. If an LCD is used, to save power the backlight on the display may be dimmed or shut after a timeout, and the intensity may be adjusted based on the ambient lighting in the vicinity of the pump.

Modes of Operation

Generally, the blood flow control device may be operated in one of three ways: 1) the blood flow control device may be operated manually (e.g., by hand); 2) the blood flow control device may be operated by a controller (e.g., system controller) in an automatic mode of operation; or 3) the blood flow control device may be operated by a controller (e.g., system controller) in a manual mode of operation.

In order to manually (e.g., hand operated) operate the blood flow control device, a user may manually move a pump (e.g., by hand) to inflate and/or deflate an expandable member of the blood flow control device. When manually operating the blood flow control device, the pump may be decoupled from the system controller.

Additionally, a system controller may be used to operate the blood flow control device. The system controller may operate in two modes of operation, for example, an automatic mode and a manual mode. In both of these modes, the pump may be coupled to the system controller.

In the automatic mode of operation, the system controller may receive one or more inputs (e.g., prior to the endovascular procedure and/or during the endovascular procedure) from a user indicating target physiologic conditions for the patient. In some variations, the system controller may analyze historical data of physiologic conditions for various subjects during the endovascular procedure and may automatically identify target physiologic conditions for the patient based on the analysis. The system controller may control a movement of the actuator (e.g., circular gear) based on the target physiologic conditions. More specifically, the system controller may control an actuation mechanism (e.g., a motor) operably coupled to the actuator. The movement of the actuator may cause an actuating element (e.g., a linear gear) on the plunger of the pump to translate, thereby causing the plunger to move within the cylindrical body of the pump. Accordingly, the system controller may inflate and/or deflate an expandable member by controlling the actuator (e.g., via the actuation mechanism) based on the target physiologic conditions. During the endovascular procedure, the system controller may receive data from the sensors that may be indicative of the physiologic condition of the patient. The system controller may compare the sensor data to the target physiologic condition. The system controller may control the movement of the actuator, thereby controlling the movement of the pump based on this comparison. In some variations, one or more of a position sensor, motion sensor, and contact sensor may track a position and/or movement of the pump and/or other component of the system as described in more detail herein. The system controller may consistently monitor these positions and/or movements and may adjust the movement of the actuator (e.g., via movement of the actuation mechanism) accordingly.

In a manual mode of operation, a user may utilize a user interface of the controller (e.g., press one or more buttons) to adjust the volume of the expandable member. For example, a user may press buttons included on the housing of the system controller. In some variations, a user may press buttons on a user interface of the blood flow control device including a touch surface. Pressing the button may cause the actuator to move, thereby causing the actuating element to move. For example, a user may press a first button to translate the actuating element so as to inject fluid out of the pump. Similarly, the user may press a second button to translate the actuating element so as to withdraw fluid into the pump. The user may constantly monitor the physiologic condition of the patient (e.g., by looking at the physiologic conditions displayed on the display device or by manually monitoring the physiologic conditions). Based on this monitoring, the user may push the buttons to actuate the pump to inflate and/or deflate the expandable member. The user may switch between the different operation modalities (i.e., manually (hand-operated), automatic mode using system controller, manual mode using system controller) as desired. For example, during the endovascular procedure, the user may manually (e.g., hand-operated) operate the pump initially during insertion of the elongate body into the blood vessel and may manually inflate the expandable member to a maximum occlusion (as further described below). The user may then couple the pump to the system controller (e.g., place the pump within the recessed portion of the system controller and close the lever) so that the system controller controls the inflation and deflation of the expandable member (e.g., either by manual mode of operation using the system controller or automatic mode of operation using the system controller). Once the user couples the pump to the system controller, the user and/or the system controller may switch between the manual mode of operation using the system controller and the automatic mode of operation using the system controller as desired. For example, if the system controller detects errors such as dampening in a sensor, blood clotting, increase or decrease in expandable member pressure, etc., the system controller may automatically switch the mode of operation from the automatic mode of operation using the system controller to the manual mode of operation using the system controller. In some variations, the user may press a button on the system controller associated with changing the mode of operation. By pressing the button, the user may switch the mode of operation from the automatic mode of operation using the system controller to the manual mode of operation using the system controller. In some variations, a user may be able to temporarily override the automatic mode, by, for example, providing instructions, e.g., via a user interface of the device and/or system controller, to the device and/or system controller to manually adjust fluid transfer. After the manual adjustment, the system may automatically revert to the automatic mode without further user input. For example, when fluid delivery to an expandable member of a blood flow control device is automated, the user may override the automatic mode to manually adjust inflation and/or deflation of the expandable member using the controller (e.g., by pressing a button on the user interface instructing the controller to inflate or deflate the expandable member), after which the controller will automatically resume automated control. In this manner, a user may momentarily and temporarily override automated control in the automatic mode without fully transitioning to the manual mode. Moreover, the user may switch to the manually operated (hand-operated) modality by decoupling the pump from the system controller at any time as desired. It should be readily understood that the user and/or the system controller may switch between the three different ways of operation as desired.

The blood pressure may include any number of blood pressure values, including but not limited to, proximal systolic pressure, proximal diastolic pressure, proximal pressure pulsitility, PMAP, distal systolic pressure, distal diastolic pressure, distal pressure pulsatility, and/or DMAP.

For example, in one variation, the blood pressure used to automatically control the expandable member may be DMAP. In this variation, the system may receive a target DMAP (e.g., a user may set a target DMAP via the user interface) and the system may measure the patient's current DMAP (e.g., based on distal sensor data). If the current DMAP is higher than the target DMAP, the system controller 106 may determine the size of the expandable member 110 that will achieve the desired DMAP. For example, in variations comprising an inflatable balloon, the system controller 106 may determine an amount of fluid and/or compressed gas to be injected into the expandable member 110 to bring the currently measured DMAP to the target DMAP. The system controller 106 may then control the actuation mechanism associated with the pump 108 such that the pump 108 injects the determined amount of fluid and/or compressed gas into the expandable member 110. This inflation of the expandable member 110 may reduce the blood flowing past the expandable member 110, and thus reduce the current DMAP. Conversely, if the current DMAP is lower than the target DMAP, the system controller 106 may determine the amount of fluid and/or compressed gas to be removed from the expandable member 110 so that the current DMAP matches the target DMAP. The system controller 106 then controls the actuation mechanism associated with the pump 108 such that the pump 108 removes the determined amount of fluid and/or compressed gas from the expandable member 110. With the reduced volume of the expandable member 110, more blood may flow past the expandable member 110 and the current DMAP may increase. In this manner, the blood flow control system 100 may activate the pump 108 to adjust the size of the expandable member 110 (e.g., inflate or deflate the expandable member 110) as needed to impede or allow blood flow in the patient such that the current DMAP is increased or decreased until it matches the target DMAP or is within a target DMAP range.

In some variations, the distal sensor may show reduced pulsatility as the expandable member 110 is inflated. The pulsatility may continue to decrease as greater opposition of the expandable member 110 is made against the wall of the vessel. The relationship in loss of pulsatility in distal systolic pressure, distal diastolic pressure, and the change in the rate of increase of pressure in the expandable member 110, and the increase in current PMAP may all independently be predictive of complete vessel occlusion.

Fluid Delivery Systems

The systems for fluid delivery described herein may be used with or otherwise incorporated into the blood flow control systems described above, or used as stand-alone systems for the delivery of fluids. The systems may include various types of pump devices and their corresponding control systems. Syringe pumps, such as the syringe pump described in FIG. 10 and a corresponding controller, (a stand-alone pump controller and/or the device and/or system controllers, which have been described in detail above), may be included in the systems. Alternatively, a pressure differential pump, as further described below may be included. The systems may be used to meter precise and/or small volumes of fluid (e.g., medication and/or fluid to inflate/deflate an expandable member of a blood flow control device), or deliver large volumes of fluid (e.g., infusion of IV fluids). A compressed gas (e.g., carbon dioxide, etc.) may be delivered using the pump devices. As described here and throughout, exemplary fluids that may be delivered include normal saline, lactated ringers solution, D5 W, a medication, blood, or a blood product. A user interface of the system may display information about the fluid being delivered, such the type and volume of medication, medication expiration dates, maximum allowed dispensing rates, and manufacturing authentication to avoid use of unauthorized or counterfeit pumps (e.g., syringe pumps containing medication).

The systems may include one or more pump devices. For example, the systems may include one or more syringe pumps, one or more pressure differential pumps, or a combination of syringe pumps and pressure differential pumps. The pumps may be configured for manual control (e.g., either by hand-operating the pump or the pump controller) and/or for automated control of fluid delivery. In some instances, the pumps may be configured such that automated control of fluid delivery may be switched or transitioned to manual control of fluid delivery, and vice versa.

Pump Devices

Syringe Pumps

The syringe pumps described herein may be used to administer or deliver fluids for various purposes. When used to administer fluids to a patient, the syringe pumps may administer precise dosages of highly concentrated medication, precise dosages of blood products and/or intravenous fluids, etc. In some instances, the fluid may be delivered bidirectionally, for example, when the syringe pumps are used to control a volume of an expandable member, such as a balloon, included in blood flow control devices (e.g., balloon catheters), as described in detail above.

The syringe pumps described herein may be useful in prolonged field care (PFC) settings as they are generally capable of administering highly concentrated medications at very low infusion rates. In PFC settings, the ability to use high concentrations of medications to limit weight and bulk may be useful. For example, intravenous administration of vasopressor medications, or continuous subcutaneous or intravenous administration of pain medications may be useful. In settings with limited advanced providers but with multiple wounded war fighters, continuous subcutaneous administration of pain medications offers simplified methods of pain control that may be administered with no advanced training.

When used to precisely deliver fluids to a blood flow control device, the syringe pumps described herein may be used to automatically control a size (e.g., volume) of an expandable member (e.g., balloon) of a blood flow control device. More specifically, the syringe pumps may control the delivery and removal of fluid from an expandable member in a more accurate manner, especially when small volumes of fluid are needed to effectuate the desired change in expandable member size. For example, in some instances, it may be desirable to inflate or deflate in an amount as small as $1/1000^{th}$ of the total volume of the expandable member. In these instances, if expandable member can hold 25 milliliters of fluid, the syringe pumps may be used to deliver a minimum bolus of 25 microliters. The syringe pumps may be configured to transfer fluid to and from the expandable member at a flow rate of about 1 milliliter per second over a pressure range from 0 to about 1000 mmHg. In other variations, the syringe pumps may be used to deliver fluids (e.g., intravenous or subcutaneous fluids including medications such as vasopressor and pain medications) to a patient.

In some instances, the systems and methods described herein may utilize more than one syringe pump (e.g., two, three, four, or more), one or more of which may be used to automatically control the size of an expandable member and one or more other of which may be used to deliver (e.g., automatically) fluid to a patient. In some instances, the systems and methods described herein may incorporate two or more syringe pumps each configured to deliver fluid to a patient (e.g., in addition to a syringe pump used to automatically control the size of an expandable member, or in a system without a blood flow control device), each of which may deliver the same, or a different, fluid.

As previously described herein, the syringe pumps may comprise a syringe having a cylindrical body configured to contain fluid for delivery and a plunger at least partially positioned within the cylindrical body. The syringe pumps may also comprise a pump controller comprising a housing configured to removably receive the cylindrical body. The pump controller may further comprise a circular gear configured to engage a linear gear formed from or otherwise coupled to the plunger, a motor operably coupled to the linear gear to advance and/or retract the plunger, a gearbox to mechanically couple the motor to the circular gear, a processor, a memory, a communication module or device, a user interface, and a power source. In some variations, the pump controller may further comprise a medication recognition interface, a sensor to detect the presence of the syringe, and/or a sensor to detect the movement and/or position of the plunger and/or other component of the syringe pump (e.g., an actuator, an actuation mechanism (e.g., motor). In variations described herein where the syringe pump is part of a blood flow control system (e.g., to deliver fluid to and remove fluid from an expandable member and/or to deliver fluids (e.g., intravenous fluids, medication, etc.) to a patient), the pump controller may be part of, or may be replaced by, a device and/or system controller that has some or all of the features and capabilities described herein with respect to the pump controller. In some variations, the system may comprise a device and/or system controller and the syringe pumps may comprise separate pump controllers. Put differently, in variations in which syringe pumps configured to deliver fluid to a patient are used with the blood flow control systems described in more detail herein, the syringe pumps configured to deliver fluid to the patient may or may not comprise a dedicated pump controller, and in variations in which a dedicated pump controller is utilized, that pump controller may be separate from or integrated into the device and/or system controllers described herein. When a dedicated pump controller is not used, the device and/or system controllers described herein may control the syringe pumps.

Cylindrical Body and Plunger

In some variations, the syringe pumps used to deliver fluids to a patient may be configured as previously described herein and may have any of the components and/or features previously described. For example, referring to FIG. 10, an exemplary variation of a syringe 1308 is provided that may be configured for both manual usage and for engagement with an actuator (e.g., circular gear) for automatic control. The syringe 1308 may comprise a cylindrical body 1352 and a plunger 1354. The plunger 1354 may comprise an enlarged end or head (not shown in FIG. 10) and an elongate member 1356 coupled to and extending from the enlarged end. The enlarged end may be slidably positioned within the cylindrical body 1352, and both the enlarged end and the elongate member 1356 may be configured to move linearly within and/or relative to the cylindrical body 1352. The plunger 1354, and more specifically, the elongate member 1356, may comprise an actuation element configured to engage with an actuator of a controller (e.g., system controller, device controller, pump controller). For example, in some variations, the elongate member 1356 may comprise a linear gear 1358. The linear gear 1358 may be configured to engage with a circular gear (not shown in FIG. 10) partially or fully positioned within a housing of the pump controller, a housing of a system controller, and/or a housing of a device controller so as to actuate the syringe 1308. In some variations, the syringe 1308 may be coupled to and/or integrated with one or more sensors to identify and track a position of the plunger 1354 and/or other pump component (as described in detail above).

As also discussed above, the syringe 1308 may be automatically controlled by a controller (e.g., pump controller, system controller, and/or device controller) via the engagement of the actuator and the actuation element. For example, referring to FIG. 10 specifically, the syringe 1308 may be actuated by engaging the actuator (e.g., linear gear 1358), with the actuation element (e.g., a circular gear) thus forming a rack and pinion mechanism. In contrast to lead-screw drive mechanisms that may extend beyond the length of the plunger 1354, the linear gear 1358, and thus the rack and pinion mechanism, may be incorporated entirely within the length of the plunger 1354. Accordingly, the overall footprint of the system may be reduced.

Figure 25A:
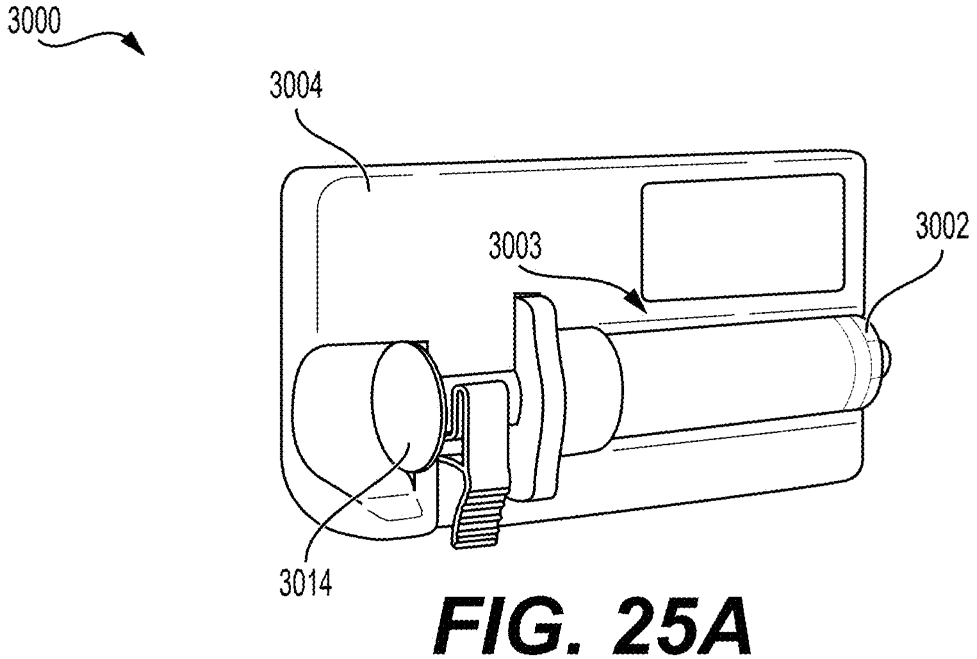
FIGS. 25A-25C depict an exemplary variation of a syringe pump.
Figure 25B:
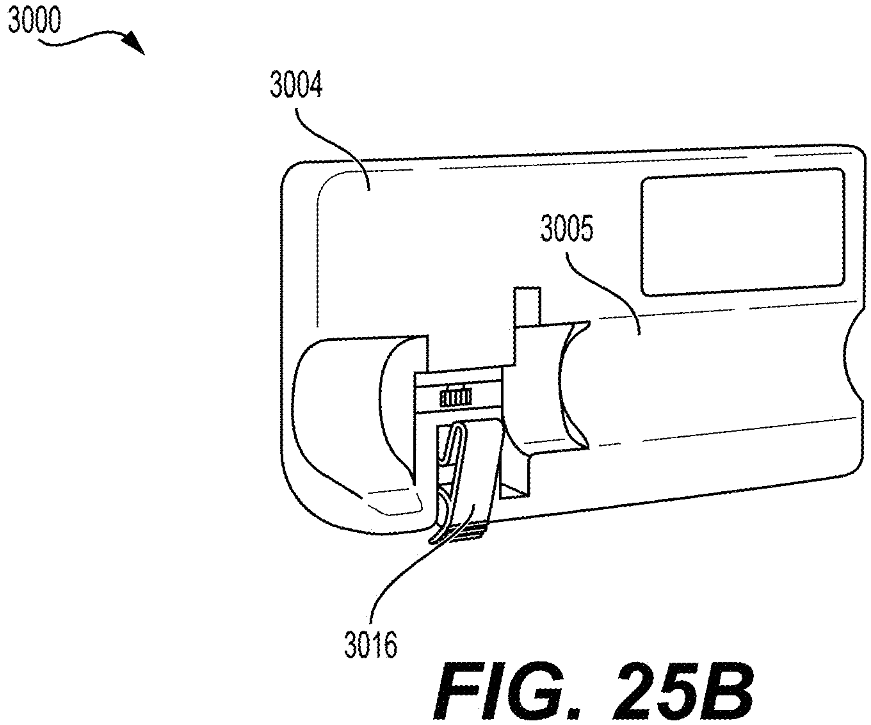
Figure 25C:
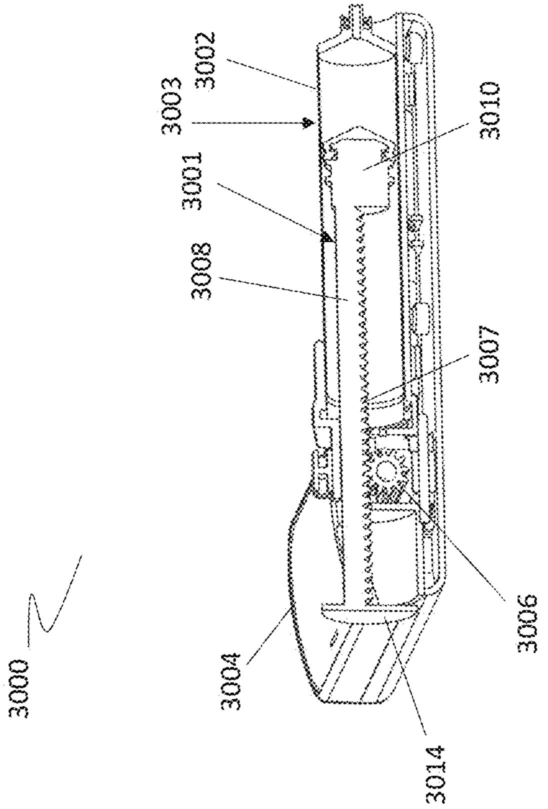

Another exemplary syringe pump is illustrated in FIGS. 25A-25C. In FIGS. 25A-25C, the syringe pump 3000 may comprise a syringe 3003 having a cylindrical body 3002 and a plunger 3001 partially disposed within the cylindrical body 3002. The cylindrical body 3002 may be releasably mounted into a housing 3004 of a pump controller. The plunger 3001 may comprise an enlarged first end 3010 positioned within the cylindrical body 3002 and an elongate member (e.g., comprising linear gear 3008) extending from the enlarged first end 3010. The plunger 3001 may further comprise a flange or handle 3014 coupled to the end of the elongate member 3008. The plunger 2001 may be linearly advanceable and retractable relative to the cylindrical body 3002 to deliver a fluid.

The plunger, and more specifically, the elongate member, may comprise an actuation element (e.g., a linear gear) configured to engage with an actuator (e.g., a circular gear) of a controller (e.g., pump controller, system controller, device controller). For example, in some variations, the elongate member itself may be configured to be a linear gear (e.g., linear gear 3008) or may otherwise comprise a linear gear. For example, the linear gear may be part of or integrally formed with the elongate member. The linear gear 3008 may include a plurality of teeth 3007 configured to engage a circular gear 3006 so as to actuate the syringe pump 3000. The pump controller housing 3004 may contain at least partially therein the circular gear 3006 and may be configured to receive the cylindrical body 3002 and provide mating between the circular gear 3006 and teeth 3007 of the linear gear 3008. For example, in some variations, the pump controller housing 3004 may comprise a cavity or chamber 3005 (e.g., a concave cavity formed within the housing) configured to receive the cylindrical body 3002. In some variations, the cavity or chamber 3005 may comprise a shape that corresponds to the shape of cylindrical body and/or plunger, such that the cylindrical body and/or plunger are easily received and held within the chamber and or cavity 3005.

Syringe Pump Controller

The syringe pump may comprise a pump controller configured to control automated actuation of the pump and delivery of fluid therefrom (or reception therein). The pump controller may further comprise an actuator (e.g., a circular gear) configured to engage an actuation element (e.g., linear gear), an actuation mechanism (e.g., a motor) operably coupled to the actuation element (e.g., the linear gear) to advance and/or retract the plunger, a gearbox to mechanically couple the actuation mechanism to the actuator (e.g., the circular gear), a processor (e.g., microprocessor), a memory, communication module or device, a user interface, and a power source. In some variations, the pump controller may further comprise a medication recognition interface, a sensor to detect the presence of the syringe, a sensor to detect the movement and/or position of the plunger or other component of the syringe pump (e.g., motor of pump controller), and a lock.

The pump controller may comprise a housing configured to receive the cylindrical body and plunger therein. For example, in some variations, the housing may comprise a cavity, chamber (open or closed) or other opening configured to receive the cylindrical body and plunger and to hold the cylindrical body in place relative to the controller housing. The pump controller may further comprise a lock (e.g., a latch) coupled to the pump controller housing, and the lock may be configured to releasably couple the cylindrical body and/or the plunger (e.g., the elongate member of the plunger) to the housing to maintain the position of the cylindrical body relative to the controller housing. The lock may also assist in aligning the actuator (e.g., the circular gear) and the actuating element (e.g., the linear gear).

The controller housing may at least partially house an actuator, which may comprise a circular gear (pinion gear), configured to engage an actuation element of the plunger, and the actuation mechanism (e.g., motor) operably coupled to the actuator, such as, for example, via a gearbox. As described in more detail herein, the actuation element may comprise a linear gear (rack) and may be coupled to or integral with the plunger. The actuator may be configured to engage with the actuation element, such that rotational movement of the actuator may be translated to linear movement via the actuation element. In this manner, rotation of the actuator may linearly advance the plunger. The processor/memory of the pump controller may be configured to control actuation of the actuator (e.g., circular gear) based on the position and/or movement of one or more components of the syringe pump, such as, for example, the position and/or movement of the actuation mechanism (e.g., motor), the actuator, and/or the plunger detected by one or more sensors.

The pump controller may comprise one or more processors. Generally, the one or more processors (e.g., CPU) may process data and/or other signals to control one or more components of the pump. The processor may be configured to receive, process, compile, compute, store, access, read, write, and/or transmit data and/or other signals. In some variations, the processor may be configured to access or receive data and/or other signals from one or more of a sensor and a storage medium (e.g., memory, flash drive, memory card). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may be, for example, a general-purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Generally, the pump controllers described herein may comprise a memory configured to store data and/or information. In some variations, the memory may comprise one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with an external device, such as, for example, a blood flow control device, such as signal waveform generation, expandable member control, data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

The pump controller may further comprise an actuator (e.g., circular gear) and an actuation mechanism, each of which may be at least partially positioned within the pump controller housing. The actuation mechanism may be operably coupled to the actuator (e.g., the circular gear). In some variations, the actuation mechanism may be directly coupled to the actuator, while in other variations, the pump controller may further comprise a gearbox containing one or more gears, through which the actuation mechanism may be coupled to the actuator. Put differently, in some variations, the actuation mechanism may be operably coupled to the circular gear via the gearbox. In some variations, the actuation mechanism may be or may otherwise comprise a motor. The motor may be any suitable motor, such as, for example, a stepper motor. The gearbox may be contained within the controller housing or mounted on the controller housing via, for example, mechanical connectors such as screws. The pitch diameter of the actuator (e.g., the circular gear) and the gear ratio of the gearbox may be the same as that described in detail above.

The pump controller may also include a wired or wireless communication module or device configured to communicate with another device, e.g., a tablet, a smart phone, etc., that may control the pump. In some variations, the communication module or device may be configured to communicate with external devices, such as, for example other treatment devices like a blood flow control device, and/or the communication module or device may be configured to communicate with a main network or hub via which the pump (and optionally other treatment devices) may be controlled. The communication module may be configured to communicate via wireless protocols such as Bluetooth, Wi-Fi, and/or a cellular network and/or via wired protocols such as UART, RS232, Ethernet, etc. The communication interface includes the ability to connect to other devices for conveying system state and reporting of data, as well as getting input for changing state or configuration.

The pump controller may also comprise a user interface communicably coupled to the processor and/or memory such that the processor may receive data related to the pump (e.g., position of the plunger, displacement of the plunger, volume of fluid inside the cylindrical body, volume of fluid delivered, volume of fluid received, a combination thereof, and/or the like) and the user interface may display data. The user interface may include a display, such as an LCD or OLED panel, one or more LEDs, and/or an audio output, such as an audio speaker. It may also include haptic output. The user interface may also be configured to receive user input, such as from physical buttons and/or a touchscreen of the user interface. The user interface (e.g., buttons or touchscreen of the user interface) may be used to provide information to the pump, such as, for example, a desired volume of fluid to be delivered and/or a type of fluid to be delivered (e.g., a type of medication).

The pump controller (e.g., the processor of the pump controller) may instruct or otherwise activate the actuation mechanism to deliver fluid from the pump and/or, in some variations, draw fluid into the pump. For example, the processor may be configured to activate the actuation mechanism for a desired duty cycle and period. For example, in variations comprising a stepper motor, the processor may be configured to activate the motor to perform a specified number of steps every certain period of time (e.g., 1 step every 10 milliseconds), and/or to perform a specified number of steps during a certain period of time (e.g., 10 steps during the course of 10 milliseconds), and/or to delay a certain period of time before performing a specified number of steps (e.g., wait 500 milliseconds before preforming another 10 steps).

The pump controller may further comprise a power source. The power source may be housed within the pump controller housing. The power source may comprise an integrated battery pack and/or a connection to an external battery pack. In some variations, the pump controller may further comprise an AC-to-DC converter. In some variations, the pump controller may be electrically coupled to an external power source. In variations comprising a battery pack, the batteries may or may not be rechargeable.

As discussed above, the pump controller may include a sensor configured to detect a presence of the syringe pump. In some variations, the sensor may comprise a syringe recognition circuit. In some variations, in addition to detecting the presence of the syringe pump, the syringe recognition circuit may also be configured to detect the type of syringe pump that is being used and/or identify details on medication that may be contained within (e.g., prefilled in) the cylindrical body. In variations comprising a syringe recognition circuit, the pump controller may comprise a mechanical switch that may be electrically coupled to the processor of the pump controller. When the syringe pump is inserted into the cavity, chamber (open or closed) or otherwise coupled to the controller housing, the mechanical switch may close an electrical path. The processor may therefore detect that the syringe pump has been properly inserted into the cavity, chamber (open or closed) or otherwise coupled to the controller housing. The processor may also detect the type of syringe pump and the amount of medication based on an output voltage from the syringe recognition circuit. In some variations, the recognition circuit may include optical recognition of a barcode or QR code, or an electronic circuit to read a memory chip positioned to the side of the syringe.

The pump controller may also be operably coupled to a medication recognition device or interface that may be configured to provide information to the processor about the fluid (e.g., medication) within the cylindrical body. This information may include the type of fluid (e.g., medication), the concentration of the fluid (e.g., medication), the maximum flow rate for the fluid (e.g., medication). In some variations, this information may also include the expiration data for the medication, and/or authentication codes for the medication. Some or all of these parameters may be presented to the user via the user interface. If the user attempts to set a flow rate for the medication delivery that is greater than the maximum flow rate, the processor may notify the user, refuse that setting, and/or require a secondary user authentication. Similarly, if the medication is beyond the expiration date or the authentication codes do not show it to be from a valid manufacturing lot, the processor may notify the user, refuse that setting, and/or require a secondary user authentication.

In some variations, the syringe pumps described herein may include one or more sensors configured to detect a position and/or movement of a component other than the plunger. For example, the syringe pumps described herein may include optical sensors such as optical encoders and/or magnetic sensors, such as magnetic encoders to detect the position and/or movement of an actuation mechanism such as a motor, which in turn may, in some variations, be used to determine movement and/or position of the plunger. In other variations, the syringe pumps described herein may utilize the position and/or movement of the motor to control or otherwise inform fluid transport without determining a particular position and/or movement of the plunger associated with that motor's position and/or movement respectively. Sensors configured to detect the position and/or movement of the motor may be included in the controller (pump controller, system controller, device controller). For example, these sensors may be coupled (e.g., mechanically coupled and/or optically coupled, or magnetically coupled) to the motor. The sensors may detect a change in reflected or transmitted light (e.g., optical sensors) or a change in magnetic fluxes (e.g., magnetic sensors) due to movement of the motor. This change may be analyzed by the processor of the controller (e.g., pump controller, device controller, system controller). The processor may determine an amount of motor movement (e.g., for a stepper motor, a number of steps the motor took) based on these changes. In some variations, the sensors may detect an amount of movement every certain period of time (e.g., a number of steps taken by the motor every certain period of time). For example, the sensors may detect an amount of movement every 10 seconds, every 9 seconds, every 8 seconds, every 7 seconds, every 6 seconds, every 5 seconds, every 4 seconds, every 3 seconds, every 2 seconds, every second, every 0.5 seconds, every 0.1 seconds, every 0.05 seconds, every 0.01 seconds, every 0.005 seconds, every 0.001 seconds, every 0.0005 seconds, or 0.0001 seconds. Additionally or alternatively, such sensors may have high resolution relative to the motor. That is, such sensors may be configured to indicate a higher number of steps for every physical movement of the motor. As discussed above, the sensors may generate pulses and/or encoder steps that may be indicative of the movement of the motor. As a non-limiting example, encoder steps may be generated such that one physical step of the motor may be indicated by 20 encoder steps. For instance, the sensors may be configured such that the processor may indicate 20 steps for every physical movement of the motor. It should be appreciated that in variations in which the syringe pumps described herein are operably coupled to or otherwise part of a blood flow control device or system, that the one or more sensors configured to detect a position and/or movement of a component other than the plunger may be part of a blood flow control device controller and/or a system controller.

The pump controller may also comprise or be operably coupled to a medication recognition device or interface that may be configured to provide information to the processor about the fluid (e.g., medication) within the cylindrical body. This information may include the type of fluid (e.g., medication), the concentration of the fluid (e.g., medication), the maximum flow rate for the fluid (e.g., medication). In some variations, this information may also include the expiration data for the medication, and/or authentication codes for the medication. Some or all of these parameters may be presented to the user via the user interface. If the user attempts to set a flow rate for the medication delivery that is greater than the maximum flow rate, the processor may notify the user, refuse that setting, and/or require a secondary user authentication. Similarly, if the medication is beyond the expiration date or the authentication codes don't show it to be from a valid manufacturing lot, the processor may notify the user, refuse that setting, and/or require a secondary user authentication.

The syringe pump may further comprise various safety mechanisms. For example, the syringe pump may include one or more of: encryption and authentication on communication between the syringe pump and other devices and/or a network (e.g., any remote data logging and control services), redundant processors and/or redundant algorithms, redundant sensors to detect the presence of the syringe, and/or the position and/or movement of the plunger or other syringe pump components such as the motor or actuator, detection of a state of the syringe pump (e.g., cylindrical body empty, full, partially full), and detection of a fault in the syringe pump (e.g., pump controller), such as, for example, a fault in the motor.

Pressure Differential Pumps

The fluid delivery systems described herein may include one or more pressure differential pumps to deliver or administer fluids to a patient. The pressure differential pumps may deliver precise dosages of highly concentrated medication, precise dosages of blood products, and/or intravenous fluids, etc. In contrast to the peristaltic rack mechanism used by commercially available infusion pumps that both pumps and meters fluid simultaneously, and which are typically complex, heavy, and require continuous power to operate, the pressure differential pumps described herein generally harness the power of differential pressures that can be created between a fluid reservoir (e.g., a bag holding medication, blood, a blood product, or IV fluid) and the patient to power fluid delivery.

In general, the pressure differential pumps described herein may include a disposable unit, a durable (e.g., reusable) unit, and a pressure mechanism (e.g., a positive-pressure device such as a pressure bag or pressure cuff). Various types of valves and pressure sensors may be included with the disposable unit, durable unit, and/or pressure mechanism to create the pressure differential and/or control the flow of fluid. Furthermore, any number of valves and pressure sensors may be employed, and they may be configured in various ways in the pump. In some variations, as further described below, a flow restrictor may be used to control metering of fluid from the pump.

Additionally, when a medication is to be delivered, the pressure differential pumps may be configured to use electronically readable prefilled medication bags to partially automate the programming of the pump. Through the electronic reading, the pump may automatically identify the medication, the concentration of the medication, expected doses or rates of infusion, and the expiration date, thus reducing the number of errors that may occur with medication administration. Cryptographic signatures on the data may further be included to confirm authenticity of the medication.

Pressure Mechanisms

The differential pressure in the pump may be created by a pressure mechanism. The pressure mechanism may be manually or automatically controlled. When manually controlled, the pressure differential may be created by manually increasing the pressure around a fluid reservoir (e.g., a bag or container holding medication, blood, a blood product, or IV fluid) with a pressure mechanism, or by compressing or squeezing the fluid reservoir by hand. In other variations, the pressure mechanism may be automated to create the pressure differential using a pump-driven device. The pumps may monitor the pressure differential and subsequently meter the fluid delivery via small sequential boluses.

In some variations, the pressure mechanism may be a positive-pressure device configured to apply pressure to the fluid reservoir. The positive-pressure device may be a pressure bag or a pressure cuff that may be placed around a fluid reservoir and inflated to increase pressure within the fluid reservoir. Inflation of the pressure bag or pressure cuff may be accomplished by squeezing a hand-operated pump (e.g., a bulb pump) that has a one-way valve or by an associated electrically driven pump. To illustrate, when a fluid reservoir such as a medication bag is placed at a higher elevation than the patient, the pressure in the medication bag will naturally be higher than the pressure in the patient's vein. However, to achieve higher flow rates, a higher pressure may be needed in the medication bag. In this case, the pressure cuff can be placed around the medication bag and inflated to compress the bag, which then creates the higher pressure in the bag and higher overall differential pressure between the medication bag and the patient.

Disposable Unit

The disposable unit of the pressure differential pump may comprise a housing, where the housing may include the one or more valves and one or more pressure sensors. The disposable unit may be placed between the fluid reservoir and the patient, and thus may include a first connector to connect the fluid reservoir with the disposable unit, and a second connector to connect the disposable unit with the patient. More specifically, at the inlet side of the disposable unit, there may be a first connector for tubing to the reservoir that contains the fluid. At the outlet side of the disposable unit, there may be a second connector for tubing to the percutaneous access device (e.g., IV needle) inserted into the patient. The number of connectors will typically vary with the number fluid reservoirs being used.

The disposable unit may include one or more valves configured to control the flow of fluid from the inlet to the outlet, and one or more sensors configured to measure the pressure of the fluid, e.g., on the inlet and outlet sides of the valve. The valves and sensors may be operably coupled to a processor and electronically readable memory for storing data (e.g., calibration data associated with the disposable part) in the durable unit, as further described below. A filter may also be provided in the disposable unit to prevent air bubbles from passing into the patient.

The valves included in the disposable unit may be any type of valve suitable for regulating fluid flow using a pressure differential pump. In some variations, the valve may be a solenoid valve. The solenoid valve may be a non-latching type valve. Although power consumption is high, non-latching valves may be beneficial since they have some inherent safety advantages. For example, non-latching valves close when no power is present, such as in the case of a catastrophic power failure. In other variations, the valve may be a motorized valve (e.g., a motorized ball valve, pinch valve, solenoid valve, or diaphragm valve). Accordingly, the disposable unit may also include circuitry or one or more motors (e.g., a stepper motor) to actuate the valves. Other types of valves may include without limitation, check valves, pinch valves, needle valves, or any other type of valve that has on/off properties.

The valves arranged in the disposable unit may have different diameters and may serve different purposes. In one variation, a single on/off valve may be used. In another variation, two valves may be employed, one as an on/off control and the other as a flow restrictor configured for proportional control of fluid flow, or put differently, configured for partial restriction of fluid flow. In this variation, the flow restrictor might be set to restrict 0% to about 95% of the fluid flow. For example, the fluid restrictor may be set to restrict 0%, 5%, 10%, 15%, 20%, 25%, 30%, 35%, 40%, 45%, 50%, 55%, 60%, 65%, 70%, 75%, 80%, 85%, 90%, or 95% of the fluid flow. The 0% restriction setting may allow for a very large flow rate without needing to keep the first valve open all the time (which would use a lot of power). The combination of the two valves may allow for a very large dynamic range of flow. For example, a maximum flow may be a 0% restriction by the flow restrictor and 50% duty cycle on a solenoid valve, and a minimum flow may be a 95% restriction by the flow restrictor and 2% duty cycle on the solenoid valve. In this instance, the dynamic range would be 500:1. In this manner, small boluses of fluid may be delivered through the duty cycle control of a flow restrictor.

A further variation may use two or more move valves, where each is an on/off valve but with different diameters. Here, when higher flow rates are desired, a valve with a larger diameter may be used, and when lower flow rates are desired, a valve with a smaller diameter may be used. Valve diameters may depend on the pressurization of the fluid. For example, at 5 psi, the valve diameter may range from about 0.3 mm (0.12 inch) and about 1.0 mm (0.40 inch), including all values and sub-ranges therein.

The valves may be arranged in any suitable manner in the disposable unit (or in other parts of the pressure differential pump). In some variations, the valve arrangement may include a single solenoid valve having an on-off control, with one state being "flow through" and another state being "no flow." The solenoid valve may be set to the "flow through" position for a specific duty cycle and period. For example, for a particular set of pressures and desired flow rate, the valve may be opened for 83 milliseconds every 1 second. Due to the precise measurement of the pressures and the precise control over the valve timings, during the subsequent 1 second period, the valve may be opened for some other amount of time, such as 84 or 82 milliseconds. With each opening of the valve, the pressure in the fluid reservoir changes so that the next time the valve is opened, the valve may need to be open for a different duration, e.g., an increased duration unless the pressure in the patient's vein changes. The duration of valve opening may be orders of magnitude in either direction based on such factors as fluid reservoir pressures, desired flow rates, etc.

In some variations of the valve arrangement, two or more valves may be placed in parallel. The valves may have different diameters. The smallest diameter valve may be opened for the lowest flow rates and the larger diameter valve(s) may be opened for higher flow rates. Independent of the above control valve arrangements, check valves may be included in the path between the control valve and the patient. The check valves may prevent accidental reverse flow, such as if the fluid reservoir were to be removed and the pump fell to a height lower than the patient.

One or a plurality of pressure sensors may be disposed on or within any portion of the disposable unit. Any suitable type of pressure sensor may be used. For example, differential pressure sensors, gauge pressure sensors, piezoelectric sensors, capacitance sensors, or membrane pressure sensors may be employed.

When a plurality of pressure sensors are used, two pressure sensors, for example, may be included in the disposable unit (or pressure differential pump) to monitor the pressure differential. The sensors may be configured such that a pressure sensor is positioned on either side of the flow restrictor. Other sensor configurations may be used. For example, the pressure measurement may be performed by embedding the pressure sensor(s) directly within the disposable unit, with at least one pressure sensor configured to measure the pressure on the inlet side of the valve (e.g., using a first gauge pressure sensor) and another pressure sensor (e.g., a second gauge pressure sensor) configured to measure the pressure on the outlet side of the valve. In a further variation, three pressure sensors may be included in the disposable unit. In addition to the two sensors described above, a third sensor (e.g., a differential pressure sensor) may be added to measure the differential pressure between the inlet side of the valve and the outlet side of the valve. This third sensor may provide additional safety checks and possibly a higher accuracy in determining the pressure difference across the valve. In other variations, the pressure sensors may be distributed across the disposable and durable units. For example, the two gauge pressure sensors may be in the durable unit and the differential sensor in the disposable unit. In another variation, the fluid within the disposable unit may be coupled to a membrane sensor, and displacement of the membrane measured by another sensor located in the durable unit.

Durable (Reusable) Unit

The durable (e.g., reusable) unit may comprise a housing, where the housing includes a controller, a user interface, a communication module or device, and a power source. The controller may include one or more processors operable to process data and/or other signals to control one or more components (e.g., valves) of the pressure differential pump. The durable unit is generally coupled to the disposable unit. While part of the connection may be mechanical, there may also be an electrical connection to a memory chip built into the disposable unit. That memory chip may be an EEPROM or any other type of non-volatile memory. At manufacturing, calibration data related to the disposable unit may be stored in the memory. The calibration data may include the equations or coefficients for the required valve timings to achieved desired flow rates at various pressures. In other variations, rather than equations or coefficients, the memory may include lookup tables.

Although the valves and/or motors for controlling the valves have been primarily described as being included within the disposable unit, they may also be located in the durable unit. In this case, the solenoid valve may move a pin or rod into a physical opening on the disposable unit, and that rod or pin extend to contact a valve or tubing (e.g., to create a pinch valve) within the durable part. Similarly, one or more pressure sensors may be disposed on or within the durable unit.

The controller of the pressure differential pump may include one or more processors, as previously mentioned. Generally, the processor (e.g., CPU) may process data and/or other signals to control one or more components of the pump. For example, the processor may be configured to read the pressures from two or more pressure sensors, compute the required solenoid and/or stepper motor timings, drive the control signals to the one or more solenoids and/or stepper motor, and/or control the user interface.

The processor may be configured to receive, process, compile, compute, store, access, read, write, and/or transmit data and/or other signals. In some variations, the processor may be configured to access or receive data and/or other signals from one or more of a sensor and a storage medium (e.g., memory, flash drive, memory card). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may be, for example, a general-purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like.

In one variation, the pressure sensors may have an analog style output, and may be connected to an analog-to-digital converter (ADC). In this case the processor may be configured to connect to the ADC pressure sensors via an interface such as SPI or I2C. In other variations, the pressure sensors may have the ADC built in, in which case the processor may be configured to connect directly to the pressure sensor using an interface such as SPI or I2C. The processor may be coupled to the solenoids and/or stepper motor using, for example, a driver circuit. This driver circuit may boost the voltage and/or current to the levels required for the solenoid or stepper motor. The processor may be operably coupled to the memory in the disposable unit via a bus such as I2C.

The algorithms for controlling fluid delivery may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The processor may also have an associated memory (e.g., integrated therewith or a separate memory) configured to store data. The memory may include volatile memory for storing data and intermediate calculations, as well as non-volatile storage for the program and lookup tables. In some variations, the memory may comprise one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium)

is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

The controller of the pressure differential pump may include a wired or wireless communication module or device configured to communicate with another device, e.g., a tablet, a smart phone, etc., that may, in some variations, control the pump. In some variations, the communication module or device may be configured to communicate with other treatment devices, such as, for example, a blood flow control device as described herein, and/or the communication module or device may be configured to communicate with a main network or hub via which the pump (and optionally other treatment devices) may be controlled. The communication module may be configured to communicate via wireless protocols such as Bluetooth, WiFi, and/or a cellular network, and/or via wired protocols such as UART, RS232, Ethernet, etc. The communication interface includes the ability to connect to other devices for conveying system state and reporting of data, as well as getting input for changing state or configuration.

The pressure differential pump may further comprise a power source. The power source may be housed within the durable unit or may be located elsewhere. The power source may comprise an integrated battery pack and/or a connection to an external battery pack. The batteries may or may not be rechargeable. A battery subsystem of the pressure differential pump may be designed to allow for both wired and wireless recharge, as well as rapid physical replacement. In some variations, the pressure differential pump may further comprise an AC-to-DC converter.

A variety of techniques may be employed to minimize the power consumed by the pressure differential pump. In some variations, state-of-the-art low voltage controllers and voltage regulators may be used. In other variations, selective power down of idle subsystems may be employed. In further variations, high-efficiency solenoid valves may be employed. In yet further variations, power consumption may be minimized using all three techniques.

In some variations, a bubble detector may be disposed on a side of the durable unit. IV tubing may be positioned by the user to pass through the bubble detector, which may use either ultrasound or light to detect when a bubble has come into the tubing. The processor may be coupled to the bubble detector via a bus such as SPI or I2C, or via direct signal indications (GPIO). Upon detection of a bubble by the bubble detector, the processor may signal to the user via a user interface that a bubble is present and it will halt the flow until the bubble is cleared. In one variation, the processor may be configured to activate a bubble clearing control mechanism that may automatically clear the bubble.

The housing and associated printed circuit boards, connectors, and mountings of the durable unit may be optimized to withstand the moisture, dust, altitudes, vibrations and any temperature extremes where the pump may need to be used. 3D printing and other rapid part fabrication techniques may allow for quick and efficient iteration on the enclosure design. The tolerances may be verified using environment chambers and industry standard tests for fluid and particulate matter ingress. Pressure transfer membranes may also be included that may allow for isolating the pressure sensors from the fluid (e.g., medication) being delivered. This may help avoid cross-contamination between patients to thus allow the pressure sensors to be in a reusable (e.g., non-disposable) part of the pump.

User Interface

The pressure differential pumps described herein may include a user interface communicably coupled to the processor and/or memory such that the processor may receive data and/or display data. The user interface may also be configured to adjust one or more parameters of the pump controller. The user interface may include a display, such as an LCD or OLED panel, one or more LEDs, and/or an audio output, such as an audio speaker. It may also include haptic output. The user interface may also be configured to receive user input, such as from physical buttons and/or a touchscreen of the user interface. The user interface (e.g., buttons or touchscreen of the user interface) may be used to provide information to the pump, such as, for example, a desired flow rate and/or the type of fluid (e.g., the type of medication, blood, or blood product).

In some variations, a processor may be coupled to the user interface to provide information about a medication to be delivered. This medication recognition interface may provide the processor with information about the fluid contained in the fluid reservoir. This information may include one or more of the type of medication, its concentration, the maximum flow rate, the expiration data, and authentication codes. Some or all of these parameters may be presented to the user via the display of the interface. In some instances, if the user attempts to set a flow rate greater than the amount read by the medication recognition interface, the processor may notify the user and refuse that setting or require a secondary user authentication. Similarly, if the medication is beyond the expiration date or the authentication codes do not show it to be from a valid manufacturing lot, the processor may notify the user and refuse that setting or require a secondary user authentication.

In variations where a the pressure cuff is used, the pressure cuff may have an associated hand-operated air pump that may be activated by the user. In this case, the processor in the durable unit may use the user interface to instruct the user to inflate the cuff, typically by squeezing a bulb pump that has an associated one-way valve. In other variations, the pressure cuff may have an associated electrically driven pump and the communication interface, and the processor in the durable unit may provide a command, e.g., via the communication module, to activate the air pump. In this case, the communication module may be configured to utilize Bluetooth or another short-range wireless or wired means.

Exemplary Pressure Differential Pumps

In some variations, the pressure differential pumps may comprise a reservoir containing a fluid, a housing coupled to the fluid reservoir and comprising a flow restrictor and a first pressure sensor, and a pump controller configured to control opening of the flow restrictor based on a pressure measured by the first pressure sensor. An EEPROM memory chip or other type of non-volatile memory may be provided in the pump controller. At manufacturing, calibration data related may be stored in the memory. The calibration data may include the equations or coefficients for the required valve timings to achieved desired flow rates at various pressures. The EEPROM memory chip may also allow a user to know what size flow restrictor has been placed in the pump.

Figure 28C:
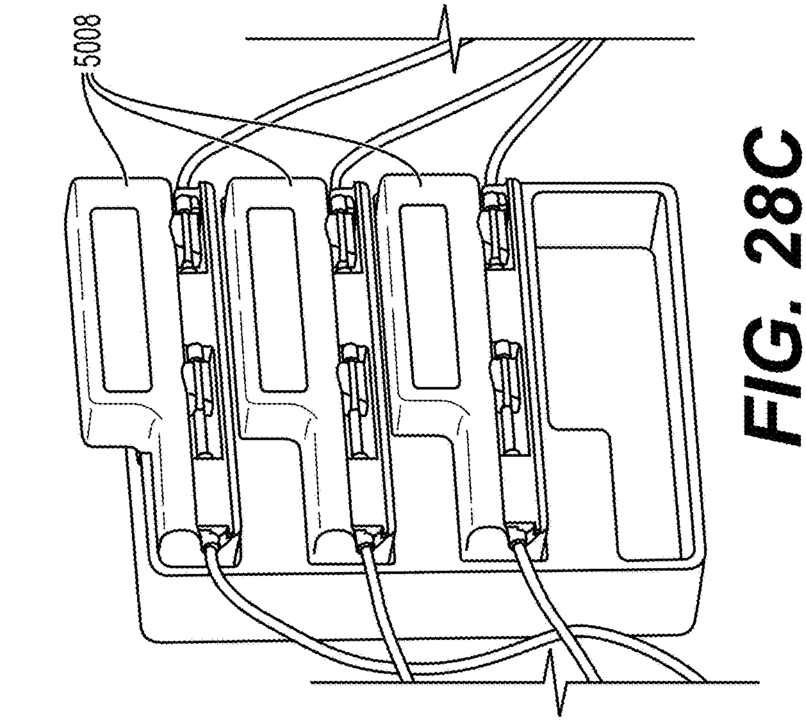
FIG. 28 illustrates exemplary variations of a pressure differential pump.
Figure 28A:
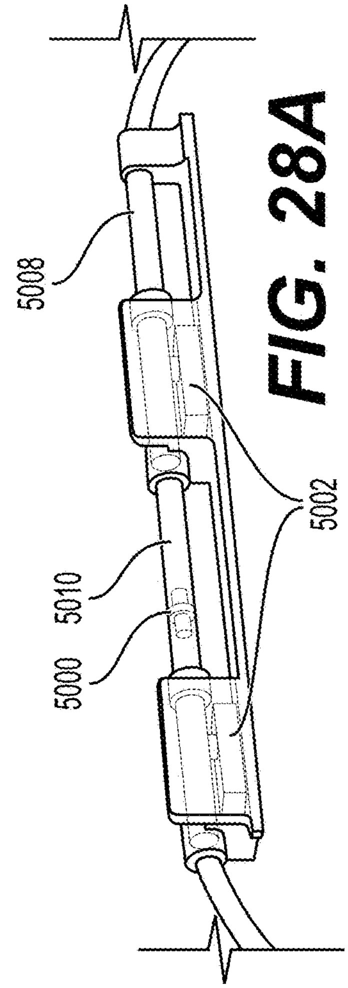
Figure 28B:
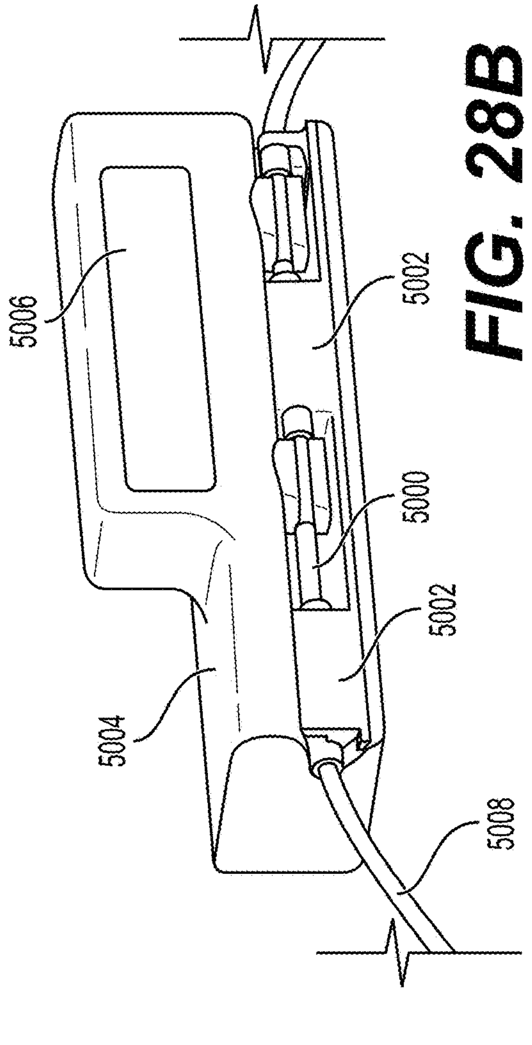
Figure 31:
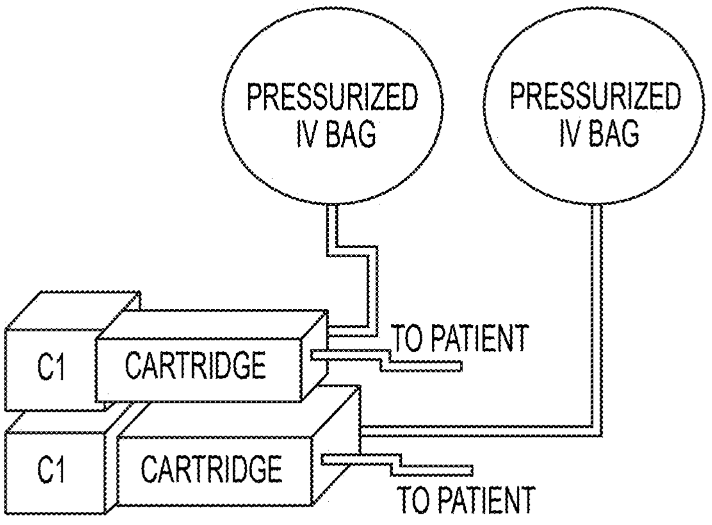
FIG. 31 depicts an exemplary variation of a reusable single channel controller for use with a pressure differential pump.
Figure 32:
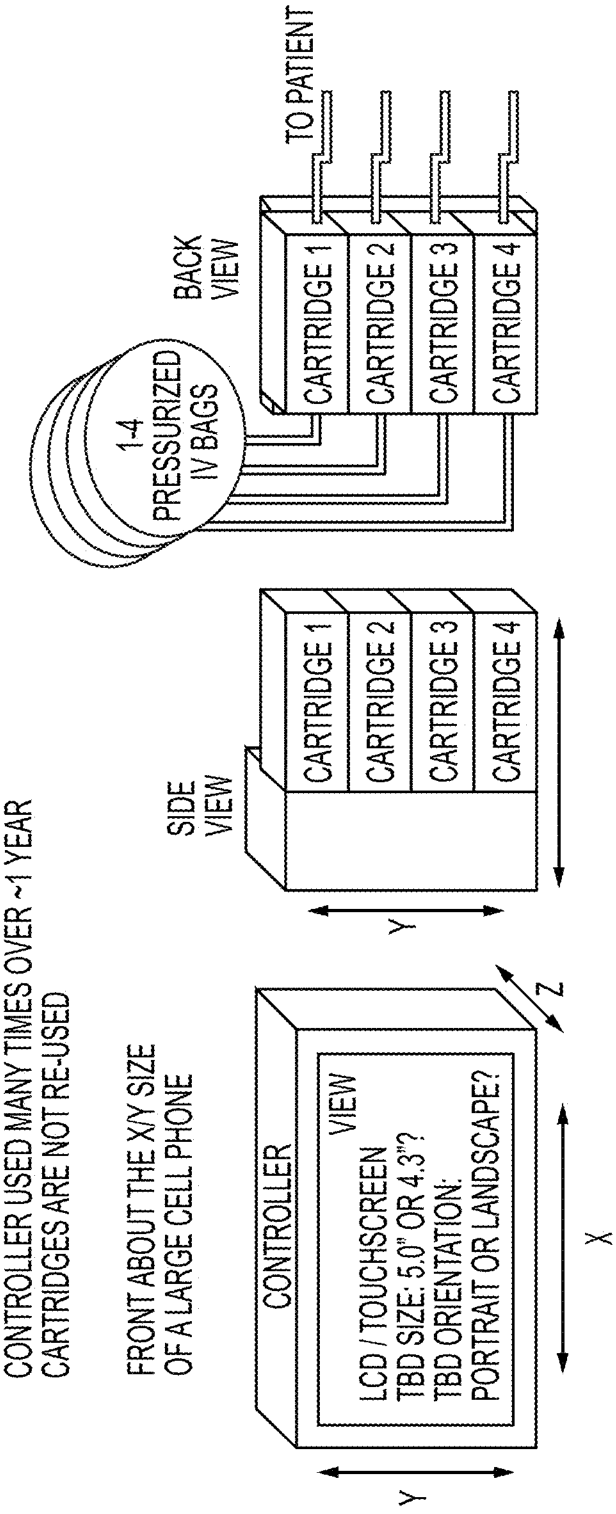
FIG. 32 depicts an exemplary variation of a disposable multi-channel controller for use with a pressure differential pump.

For example, as shown in FIG. 28 (blocks A and B), pressure differential pump includes a flow restrictor 5000 positioned between two piezoelectric sensors 5002 coupled to the tubing 5010. The flow restrictor 5000 and piezoelectric sensors may be enclosed within a housing 5004. Housing 5004 may also contain the pump controller (not shown) and a display 5006. As illustrated in block C of FIG. 28, multiple pressure differential pumps 5008 may be combined to deliver different fluids to the same patient. In further variations, as illustrated in FIGS. 31 and 32, multiple controllers may be used when multiple pressure differential pumps are employed (FIG. 31) or when a single controller with multiple channels (FIG. 32) are employed. The controllers may be reusable or disposable (i.e., not reusable). In FIG. 31, the reusable controllers (C1, C2) may attach to a single pump housing (e.g., cartridge). If more than one channel is needed, then the controllers may be stacked. Each controller may have its own wireless communication capability. In FIG. 32, a single controller may be re-used with single pumps (e.g., cartridges 1, 2, 3, or 4). In this variation, the controller may generally be a multi-channel controller capable of delivering fluid from a plurality of pressurized IV bags. The re-usable controller may include a touchscreen display.

Figure 29B:
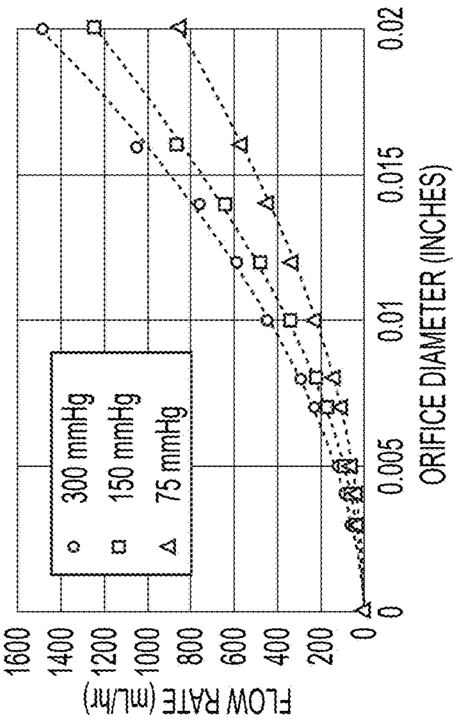
FIGS. 29A-29C provide data relating to various tests run on an exemplary pressure differential pump.
Figure 29A:
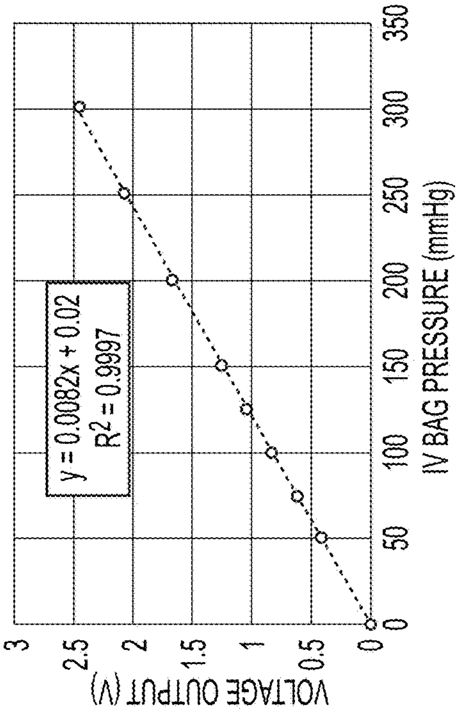
Figure 29C:
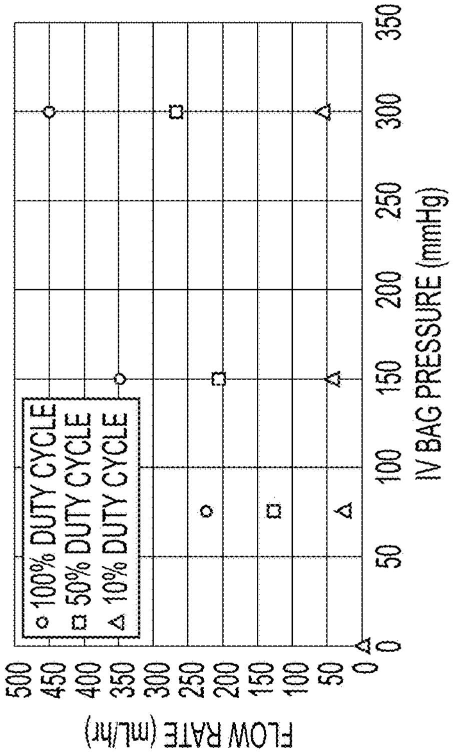

The pumps may monitor the pressure differential and subsequently meter fluid delivery via small sequential boluses, as previously stated. These small boluses may be delivered through the duty cycle control of a flow restrictor. Precise control over the flow rate may include continuously monitoring the pressure drop across the flow restrictor. In some variations, given a known pressure drop and orifice diameter, if the pressure on either side of a flow restrictor is known and the size of the orifice is known, then flow can be approximated using Bernoulli's principle. Testing confirming that sensors of the pressure differential pumps were capable of accurately detecting pressures is shown in FIG. 29A and described in Example 1. Additionally, testing confirming that pressure differential pumps are capable of delivering a range of flow rates commonly used during medical care is shown in FIG. 29B and described in Example 2. Duty cycle testing was also carried out as described in Example 3 to examine the pump's ability to create a broader range of flow rates by duty cycling a solenoid valve with a single sized fixed orifice. Resultant flow rates based on the duty cycle are shown in FIG. 29C.

Figure 30:
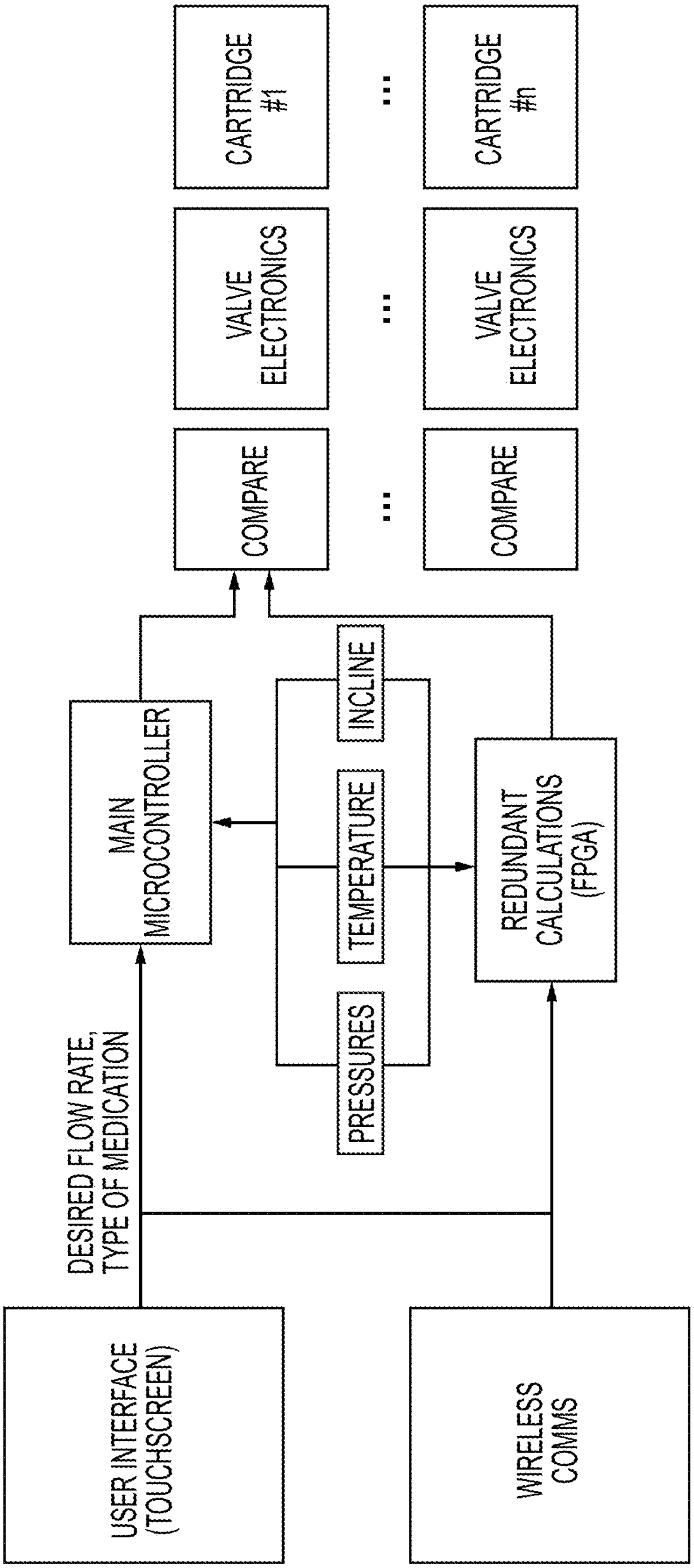
FIG. 30 is a schematic representation of an exemplary pump controller of a pressure differential pump.

Some variations of the differential pressure pump may be configured as shown in the schematic presented in FIG. 30. In this variation, the pump may be a low power pump utilizing pressure bags to create the proximal pressure differential to drive fluid administration. The pump may be configured to fit between the pressurized medication bag and an IV tubing extension connected to a central venous catheter or an IV. The pump may generally include all of the pressure sensors, flow restrictors (e.g., solenoid valves), and control electronics. Instructions for operating the pump may be received wirelessly from the main controller. A disposable cassette may contain a bubble filter, check valves, membranes for pressure sensors, and the flow restrictor. A low power pump controller (main controller, e.g., from the STM32 series of ARM microcontrollers from STMicro) may be used for calculations and control functions.

Similar to the pump controller for the syringe pump, the pump controller for the pressure differential pump may also have an accompanying wireless interface that allows export of data as well as two-way communication for programming of the pump. The pump controller may contain cryptographic and authentication functions to ensure the integrity and security of communication with other elements of the system, and data exported to back-end services.

The various measurements that may be required to calculate flow outside of the pressure differential, such as ambient pressure, temperature, and incline, may be read from integrated sensors by both the pump controller and an independent redundant circuit. The incline angle may be measured by an accelerometer included as part of the pump controller. The pump controller may also include the temperature sensor. Temperature may be measured to calculate the viscosity of temperature-sensitive fluids in the pump. An exemplary medication sensitive to temperature is propofol since it comprises an emulsion of egg lecithin and soybean oil. Both sensors may perform calculations to determine the timing on the solenoids which subsequently control the valve. A comparator may be included that checks the outputs from both independent methods, and if they match, the solenoids are opened for the appropriate time. An additional circuit in the solenoid electronics may regulate the maximum open time for the valve.

The pressure differential pump may further comprise various safety mechanisms. For example, the pressure differential pump may include one or more of: encryption and authentication on communication between the pressure differential pump and other devices and/or a network (e.g., any remote data logging and control services), redundant processors and/or redundant algorithms, and/or redundant sensors to detect the presence of the fluid reservoir.

Methods

Methods for Controlling Blood Flow

Generally, methods for controlling blood flow in a patient may include advancing a portion of the blood flow control device (e.g., the distal end of the elongate body and expandable member) to a target location in a blood vessel of a patient, manually inflating the expandable member via the pump (e.g., hand-operated) to an initial level, coupling the pump to a controller, and automatically controlling the volume of the expandable member via automated control of the pump with the controller, thereby controlling blood flow through the blood vessel. In some variations, the patient may be suffering from shock such as neurogenic, hemorrhagic, hypovolemic, and/or septic shock, and the methods may control blood flow thereby addressing the shock in the patient. For example, the methods described herein may utilize the expandable member to partially occlude the blood vessel of a patient, which may provide blood pressure support to vascular beds above the expandable member while permitting continued perfusion distal to the expandable member. Thus, methods described herein may result in a more physiologic augmentation of proximal blood pressure, while also reducing ischemic injury to distal tissues by permitting continued perfusion distal to the expandable member.

Figure 23:
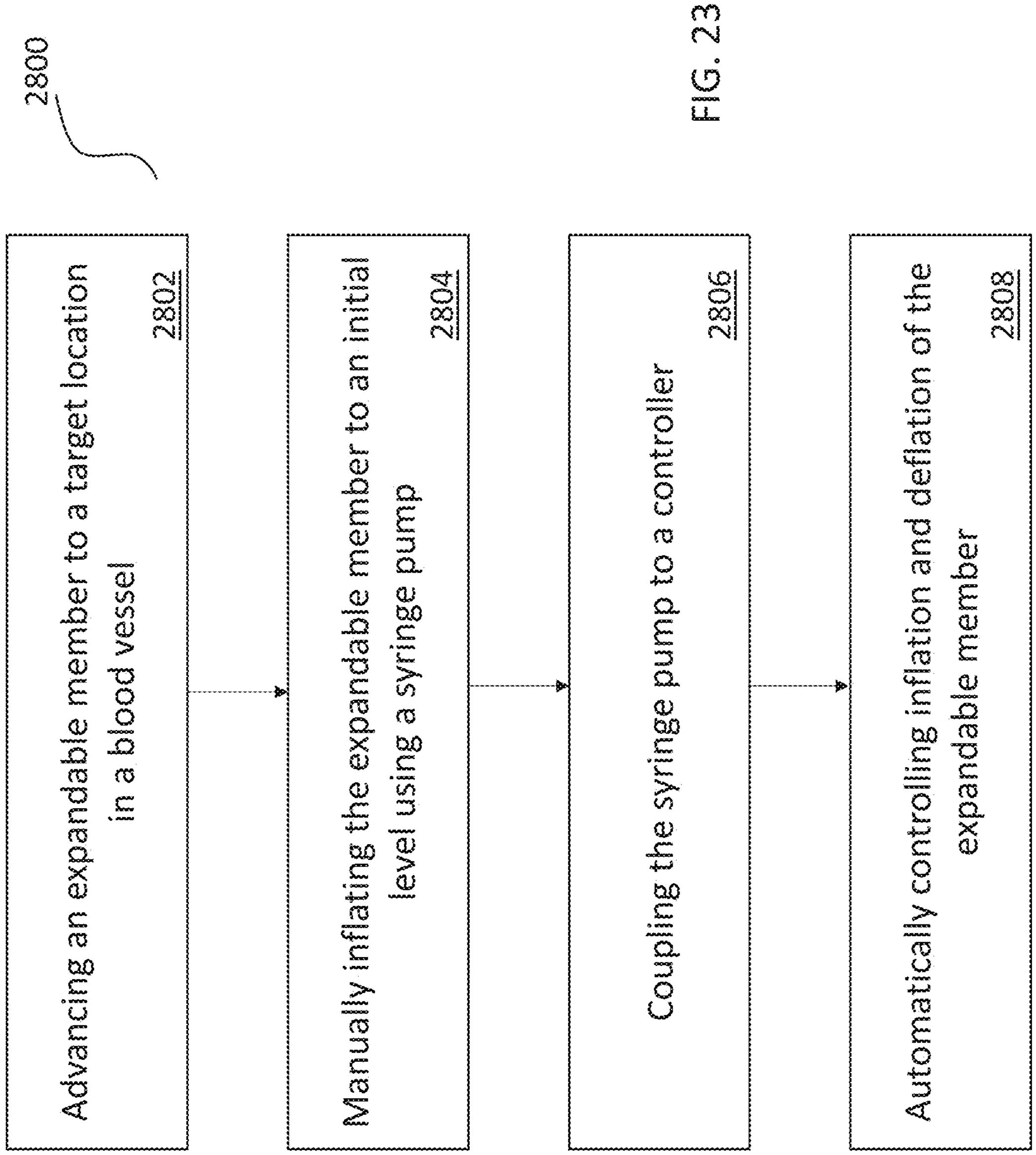
FIG. 23 is a flowchart illustrating an exemplary variation of a method for adjusting a volume of an expandable member.

FIG. 23 is a flowchart illustrating an exemplary variation of a method 2800 for controlling an expandable member. The method includes at 2802 advancing an expandable member to a target location in a blood vessel. In some variations, the elongate body or a portion thereof (e.g., a tip or end portion) may be advanced to and inserted into a target blood vessel (e.g., the aorta) via a suitable endovascular route. For example, in variations in which the target blood vessel is the aorta, the method may include inserting the end portion of the elongate body into the aorta through the femoral artery. In some variations, the elongate body may be inserted into the aorta through radial or brachial access. The elongate body may be advanced such that the expandable member is positioned at a desired location in the aorta. For example, the elongate body may be advanced until the expandable member is positioned in zone 1 of the aorta, zone 2 of the aorta, or zone 3 of the aorta. Alternatively, the blood flow control device may be inserted into the iliac arteries and not advanced into the aorta.

Once the expandable member has been positioned in the desired location, at 2804, the expandable member may be manually inflated using a pump (e.g., a syringe pump as described in more detail herein). For example, a user may detach the syringe pump from the controller (e.g., system controller), and/or the syringe pump may not yet have been coupled to the controller and thus may be held in the hand of a user and operated without using the controller. The method may include manually operating the syringe pump by applying a force to the plunger such that the plunger moves linearly relative to a cylindrical body of the syringe and a fluid is delivered to the expandable member. For example, a fluid (e.g., saline, etc.) and/or a compressed gas (e.g., carbon dioxide, etc.) may be introduced into the expandable member by manually moving the plunger of the syringe pump until the expandable member is inflated to an initial level. In some variations, the initial level may be a volume corresponding to maximum occlusion for the patient. Put another way, in some variations, after advancement of the expandable member to a target location in a blood vessel (e.g., the aorta), the method may include manually actuating the syringe pump until maximum occlusion is reached. This state may be indicated by the expandable member pressure and the loss of a pulsatile blood pressure waveform in the sensor downstream from the expandable member as indicated on the graphical user interface.

When the pump is coupled (or recoupled) to the system controller (as further described below), the method may include registering this initial inflation level as the maximum allowable inflation level for the particular patient and/or the particular procedure. For example, a position of a component of the pump (e.g., actuation mechanism such as motor, actuator such as a circular gear, actuation element such as the linear gear and/or another portion of the plunger) may be recorded when the pump is coupled to the controller after initial inflation. This position may be correlated to a maximum allowable inflation level for the blood flow control system. During subsequent automatic operation, if the movement and/or position of the pump indicates an inflation level nearing or exceeding the maximum allowable inflation level, the method may include transitioning the blood flow control device from an automatic mode of operation using the system controller to a manual mode of operation using the system controller. Additionally or alternatively, an alert may be transmitted simultaneously or substantially simultaneously to a user indicating that the maximum allowable inflation level has been reached and/or is close to being reached. In some variations, the position of a component of the pump (e.g., actuation mechanism such as a motor, actuator such as a circular gear, actuation element such as the linear gear and/or another portion of the plunger) that is recorded when the pump is coupled to the controller after initial inflation is used as a reference value for initial inflation volume. For example, when deflating a balloon of a blood flow control system, the user may use the reference value to return to the initial inflation volume. In other variations, the positions of a component of the pump (e.g., actuation mechanism such as a motor, actuator such as a circular gear, actuation element such as the linear gear and/or another portion of the plunger) that are recorded may be used to track volumes of the balloon.

Once the expandable member reaches an initial level of inflation, at 2806, the method may include coupling the syringe pump to a controller (e.g., the system controller). For example, the syringe pump may be placed in a recessed portion of the housing of the system controller. A user may then close the lever to lock the syringe pump to the system controller. In some variations, the method may also include detecting that the pump has been coupled to and/or locked to the system controller, and/or alerting the user that the pump is properly coupled to and/or locked to the system controller. For example, methods may comprise pushing, activating, or otherwise engaging a switch on the housing of the controller, using, e.g., the lever and/or a portion of the pump (e.g., cylindrical body). In some variations, the method may also include aligning an actuator (e.g., circular gear) included in the system controller and an actuation element (e.g., linear gear) on the syringe pump. For example, aligning the actuator and the actuation element may comprise engaging (e.g., closing) the lever and attaching the end of the lever to the system controller housing. While the initial inflation step is described above as completed by hand, it should be appreciated that in some variations the initial inflation step may be completed using the system controller in the manual or automatic mode.

Methods may also comprise coupling the blood flow control device and the system controller, such as, for example, operably coupling, electrically coupling, and/or mechanically coupling the blood flow control device (e.g., the device controller) and the system controller. For example, operably coupling the blood flow control device to the system controller may comprise communicably coupling the device controller and the system controller via a wired or wireless connection. Electrically coupling the blood flow control device and the system controller may comprise electrically coupling the device controller and the system controller via an electrical connector and/or a cable. Additionally or alternatively, mechanically coupling the blood flow control device and the system controller may comprise magnetically coupling the device controller and the system controller via magnets, fasteners, mechanical connectors, and/or the like. For example, in some variations, mechanically coupling the device controller and the system controller may comprise aligning one or more magnetic pins on a first surface of the device controller housing with one or more corresponding magnetic pins on a surface of the system controller housing. Mechanically coupling the blood flow control device and the system controller may additionally or alternatively comprise positioning a slide on the device controller housing within an elongate channel on the system controller housing and/or receiving a ball detent on the device controller housing within an opening on the system controller housing. After advancement of the expandable member of a blood flow control device to a target location, some variations of the method may include mechanically coupling the device controller to the system controller using one or more, including a combination of, any of the coupling and alignment mechanisms described herein. For example, the device controller may be coupled to the system controller using a combination of two or more coupling and alignment mechanisms including, but not limited to, magnets, posts, a ball detent, and a latch.

At 2808, methods may include operating the blood flow control device in any of the aforementioned operation modalities. For example, the blood flow control device may be operated in an automatic mode of operation based at least in part on target data that may be representative of target physiologic conditions for the patient. In some variations, methods may include receiving the target data, e.g., from a user via a user interface, and/or predicting the target data based on analysis of prior data. In some variations, the target data may include threshold values. For example, the target data may include any of the threshold values described herein, such as, for example, threshold values for proximal systolic pressure, proximal diastolic pressure, proximal mean arterial pressure (PMAP), distal systolic pressure, distal diastolic pressure, distal mean arterial pressure (DMAP), expandable member pressure, expandable member volume, total time at occlusion, etc. In some variations, the target data may include any of the expected and/or predicted values, such as, for example, expected and/or predicted values for proximal systolic pressure, proximal diastolic pressure, PMAP, proximal pressure pulsatility, distal systolic pressure, distal diastolic pressure, DMAP, distal pressure pulsatility, expandable member pressure, expandable member volume, total time at occlusion, etc.

The method may include receiving data (e.g., at the system controller) from one or more sensors during the endovascular procedure. In some variations, the blood flow control device may include at least one sensor. The at least one sensor may be any of the sensors described herein, such as, for example, one or more of a proximal pressure sensor, a distal pressure sensor, a flow sensor, an expandable member sensor, a barometer, and a position sensor (e.g., a magnetic encoder). In some variations, the housing of the system controller may include one or more sensors to detect a movement and/or position of the pump. For example, the housing of the system controller may include an optical sensor, and/or the like.

The system controller may receive the sensor data from the one or more sensors. The sensor data may be received after the blood flow control device has been powered on prior to advancing the blood flow control device through the vasculature, while inserting the blood flow control device, and/or during use of the blood flow control device. The sensor data may include data indicative of a physiologic condition or expandable member pressure. Physiologic conditions may include, but are not limited to, one of and/or a combination of one or more of proximal systolic pressure, proximal diastolic pressure, PMAP, proximal pressure pulsatility, distal systolic pressure, distal diastolic pressure, DMAP, and distal pressure pulsatility. The expandable member pressure may be received from an expandable member sensor. In some variations, an expandable member volume may be derived from the expandable member pressure.

When operating the blood flow control device in an automatic mode of operation, the method may further include comparing the received sensor data to the target data. The expandable member may be inflated and/or deflated based on this comparison. For example, the system controller may inflate and/or deflate the expandable member based on a comparison of the blood pressure of the patient to a target blood pressure. For instance, the system controller may receive a target blood pressure or target blood pressure range. In some variations, the target blood pressure and/or target blood pressure range may be provided to the system controller by a user via a user interface. Additionally or alternatively, the system controller may automatically predict a target blood pressure and/or target blood pressure range based on analysis of prior data. For instance, the system controller may determine a pressure range during which a patient was previously stable. The target ranges may be determined based on this determination. For instance, in a non-limiting example, if the distal pressure was determined to be 25 mmHg the last time that the proximal average pressure was stable, then the distal target pressure may be determined to be and/or set to be 25 mmHg and/or the proximal average pressure range at which the stability was exhibited may be determined as the target pressure range for the proximal average pressure. The target blood pressure or target blood pressure range may indicate the blood pressure(s) to be achieved in the blood vessel by therapeutic intervention of the expandable member. The target blood pressure can be a blood pressure either proximal to the expandable member or distal to the expandable member or any combination of the two. The method may include measuring or determining the patient's current blood pressure and comparing the measured or determined blood pressure to the target blood pressure or range. If the measured blood pressure is higher or lower than the target blood pressure, or outside the target blood pressure range, the size of the expandable member, or how to adjust the size of the expandable member may be determined so as to achieve the target blood pressure or a value within the target blood pressure range.

In order to stay within a target range or to achieve the target value by adjusting the expandable member, methods may comprise moving an actuator (e.g., circular gear) positioned in the system controller that engages with an actuating element (e.g., linear gear) on a plunger of the pump, thereby moving the plunger of the pump and adjusting the volume of the expandable member. Moving the actuator may be achieved by moving or otherwise controlling an actuation mechanism (e.g., a motor) coupled to the actuator. Put another way, methods may comprise moving the motor, thus moving the actuator, thus moving the actuation element of the pump, thereby moving the plunger of the pump and delivering fluid to, or removing fluid from, the expandable member. In some variations, moving the actuator may comprise rotating a circular gear and moving the actuation element may comprise translating a linear gear relative to a cylindrical body of syringe, thereby translating the plunger of the syringe relative to the cylindrical body of the syringe.

Methods may further comprise determining a position of the plunger and/or a desired amount of movement of the plunger to achieve a target value (e.g., target blood pressure, target volume for the expandable member, etc.), using the system controller. For example, the system controller may receive position and/or movement data indicating the position of the plunger and/or the movement of the plunger from a position sensor, such as for example an optical sensor. Methods may further comprise adjusting the position of the plunger based on the position and/or movement data. Methods may further comprise switching between the different modalities for the blood flow control systems described herein. For example, methods may include switching between manual operation (hand operation) of the pump, manual mode of the controller, and automatic mode of the controller at any desired or necessitated (based on system or patient conditions) time during before and/or during a procedure. In some variations, switching between the manual mode of the controller or the automatic mode of the controller and manual operation may comprise removing or otherwise decoupling the pump from the system controller. Switching between the automatic mode of the controller and the manual mode of the controller may comprise receiving user input, e.g., from a user interface, indicating a switch in mode is desired. Methods may further comprise removing the blood flow control device from the target blood vessel and the patient's body.

Figure 24:
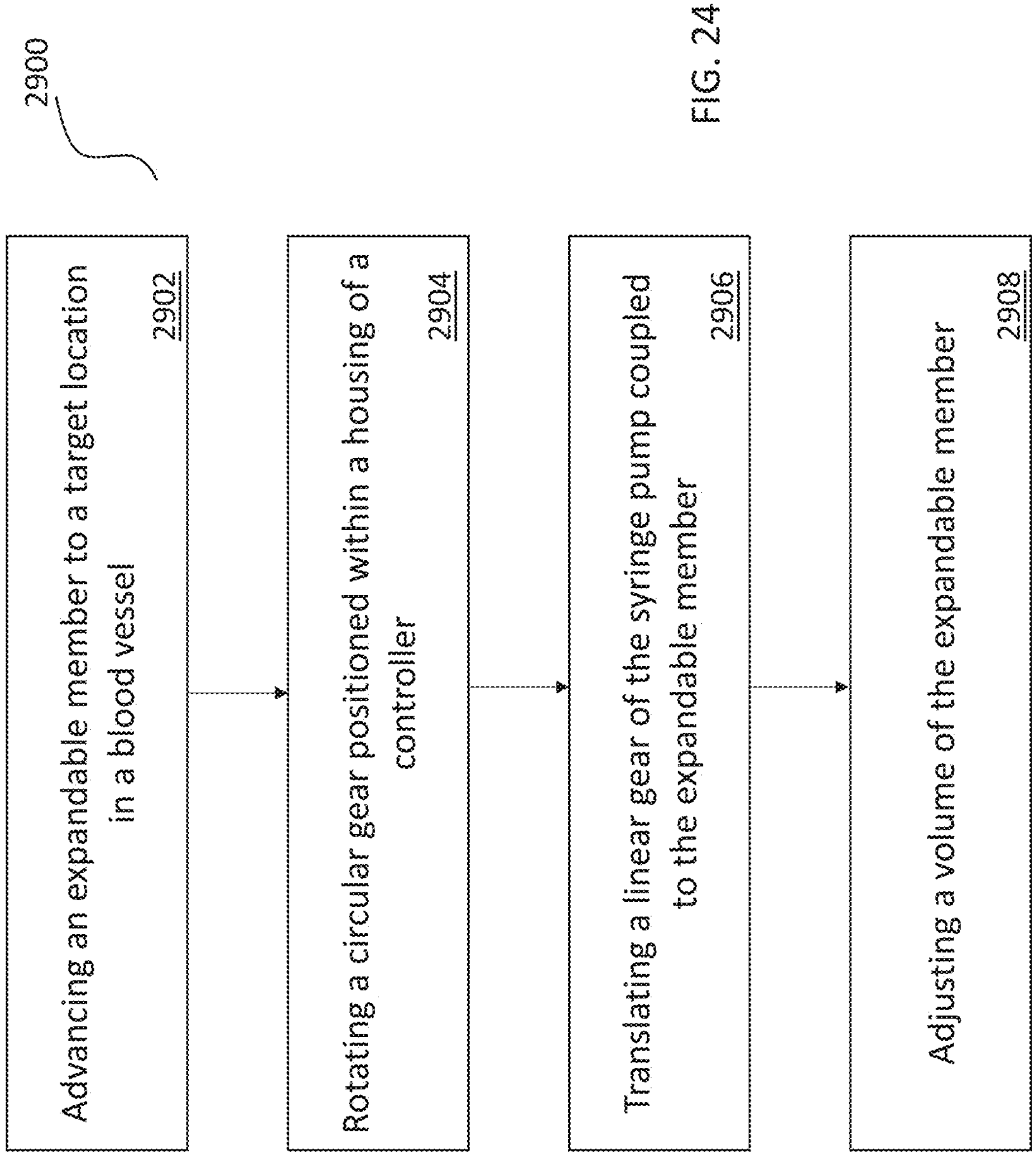
FIG. 24 is a flowchart illustrating another exemplary variation of a method for adjusting a volume of an expandable member.

FIG. 24 is a flowchart illustrating an exemplary variation of a method 2900 for controlling blood flow through a blood vessel in a patient. At 2902, the method may include advancing an expandable member of a blood flow control system to a target location in the blood vessel. The blood flow control system may comprise a system controller, a blood flow control device, and a syringe pump. The blood flow control device may comprise an elongate body and the expandable member at the distal portion of the elongate body. The syringe pump may comprise a cylindrical body and a plunger. The plunger may comprise and enlarged end and an elongate member. The elongate member may include a linear gear. A circular gear may be positioned at least partially in a housing of the system controller. In some variations, the method may include placing the syringe pump into a recessed portion of the system controller. A lever on a housing of the system controller may couple the syringe pump to the system controller, thereby aligning the circular gear to the linear gear.

At 2904, the method may include rotating the circular gear. In some variations, a motor coupled to the circular gear may rotate the circular gear. The circular gear may be rotated based on a target physiologic condition. At 2906, the method may include translating the linear gear based on the rotation of the circular gear. For example, the circular gear may engage with the linear gear such that movement of the circular gear may cause translation of the linear gear. The translation of the linear gear may cause the plunger to move within the cylindrical body. At 2908, the method may include adjusting a volume of the expandable member based on the amount of translation of the linear gear.

As discussed above, feedback on the position of the plunger and/or the movement of the plunger may be received from a position sensor, such as for example, an optical sensor. The position of the plunger and/or the movement of the plunger may be adjusted by adjusting the rotation of the circular gear.

Methods for Fluid Delivery

Methods for fluid delivery are further described herein. When a syringe pump is used, the method may comprise delivering a fluid from the syringe pump, where the syringe pump comprises a cylindrical body, a plunger disposed within the cylindrical body, a sensor, and a controller (e.g., pump controller, device controller, and/or a system controller); and detecting the position of the plunger and/or other component of the syringe pump (e.g., actuation mechanism, actuator, etc.) and/or tracking movement of the plunger and/or other component during delivery of the fluid using the sensor, as described in more detail herein. In some variations, the sensor may be a contact sensor such as a linear potentiometer or an encoder (such as an optical or magnetic encoder). The controller may control actuation of the pump (e.g., actuation mechanism, actuator, plunger) based on the position and/or movement of the component detected by the sensor. Non-limiting examples of fluids that may be delivered using the syringe pump include normal saline, lactated ringers solution, D5 W, a medication, blood, or a blood product. In one variation, normal saline may be used to expand an expandable member of a blood flow control device. In another variation, the method may include delivering a fluid to treat a patient in a hospital or field care setting.

When a pressure differential pump is used, the method may comprise delivering a fluid from the pressure differential pump, where the pump comprises a reservoir containing the fluid, and a housing coupled to the fluid reservoir and including a flow restrictor and a first pressure sensor, and a pump controller; and controlling the opening of the flow restrictor based on a pressure measured by the first pressure sensor. In some variations, the housing may include a second pressure sensor. Non-limiting examples of fluids that may be delivered using the syringe pump include normal saline, lactated ringers solution, D5 W, a medication, blood, or a blood product. In one variation, normal saline may be used to expand an expandable member of a blood flow control device. In another variation, the method may include delivering a fluid to treat a patient in a hospital or field care setting.

Mathematical modeling may be carried out to generate underlying calculations for differential pressure pump use. The calculations may be included in final equations and/or tables that may help determine the required valve open time to achieve any desired flow rate based on the current conditions. From Bernoulli's principle, it may be anticipated that the final equations may require 2nd order polynomials. If no clear equation can be derived, the valve time open requirements may be compiled in a lookup table. Even when equations are derived, lookup tables may still be used as they may be more efficient for use by the controller's firmware.

In one variation, valve timings to meet prespecified flow rates and subsequent medication aliquots may be modeled using the mass flow equation. This may then be compared to initial measurements using prototyped devices. Once consistent results can be achieved across the usable range of pressures and medication doses, the pump may then be further refined through iterative testing using an automated test jig that autonomously varies the IV bag compression, IV bag elevation, venous pressures, and temperatures across all plausible permutations. At each of those permutations, the valve may be opened for various amounts of time to determine the actual volume versus time. The tests may then be repeated with fluids of different densities.

EXAMPLES RELATING TO TESTING OF FLUID DELIVERY SYSTEMS

The following examples describe experiments that were performed to assess the feasibility of using pressure differentials to deliver fluids, and should not be construed in any way as limiting the scope of the pressure differential pumps disclosed herein.

Example 1: Piezoresistive Pressure Measurement Testing

Fluid delivery using pressure differentials was assessed using disposable piezoresistive pressure sensors and determined to provide precise fluid delivery based on IV bag pressure as well as the back pressure from the downstream line. In the experiment, a piezoresistive Wheatstone bridge with silicone diaphragm (MDX-MX950, Medex, N.J., USA) was used to measure the pressures within a section of tubing on either side of a fixed orifice. The diaphragm pressure monitor was connected to an amplifier (AD8420ARMZ-R7, Analog Devices Inc., MA, USA) and the output voltage was measured with a 12-bit ADC. This device was connected to the pressurized IV bag, with the voltage plotted against the measured IV bag pressure (see FIG. 29A). As shown in the figure, the pump provided a linear voltage output for any given pressure.

Example 2: Orifice and Pressure Testing

Orifice and pressure testing was performed on the pressure differential pumps given that the pumps may in some instances depend on the pressurization of the infusion bag. To validate that the pumps are capable of delivering a range of flow rates that are commonly used during medical care, the flow rate over several bag pressures was measured. In addition, varying sizes of fixed orifice fluid resistors were included to establish the feasibility of having color-coded flow capped disposables to improve safety and reduce user error. Using a standard blood pressure cuff that could be found in any advanced medics pack in a PFC setting, we wrapped the pressure cuff around saline filled infusion bags and maintained constant pressure using a pressure regulator as the infusion bag drained. The blood pressure cuff was inflated to 75, 150, and 300 mmHg pressure as measured by the accompanied pressure gauge. To measure flow, a commercial flowmeter (LD20-2600B, Sensirion, Staefa, Switzerland) was used at a sampling frequency of 200 Hz. The mean flow rate was averaged over a 10 second period to determine the steady-state flow. Finally, fixed orifice fluid resistors (OCP-STR-KT, Orange Coast Pneumatics, CA, USA) were added between the pressurized IV bag and flowmeter to establish the relation between pressure drop and flow rate. FIG. 29B shows the results of this experiment. For any pressure, a characteristic curve may be calculated to predict the flow rate based on the orifice size.

Example 3: Duty Cycle Testing

In this test, a 0.01" fixed orifice was used in conjunction with a low power inexpensive solenoid valve (VapLock Solenoid Operated Pinch Valve, Cole-Parmer, IL, USA). The system was tested at IV bag pressures of 75, 150, and 300 mmHg. The valve was then duty cycled with an open position at 100%, 50% and 10% over a time period of six seconds. The flow rate was measured as the volume accumulated in a graduated cylinder in a 30 minute time interval (see FIG. 29C). For any given differential pressure, a characteristic flow rate may be calculated from the known duty cycle. It may thus be possible to create a known range of flow rates based on duty cycle for each orifice size and pressure differential.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A system configured for an endovascular procedure, the system comprising:

a blood flow control device comprising an elongate body and an expandable member positioned at a distal end of the elongate body;

a syringe pump in fluid communication with the expandable member, wherein the syringe pump comprises a cylindrical body and a plunger, the plunger comprising an enlarged first end positioned within the cylindrical body and configured to move linearly therein, and an elongate member extending from the enlarged first end, the elongate member comprising a linear gear; and a controller communicably coupled to the blood flow control device and releasably coupled to the syringe pump, wherein the controller comprises a housing and a circular gear positioned at least partially within the housing, wherein the circular gear is configured to engage the linear gear to actuate the syringe pump and adjust a volume of the expandable member.

2. The system of claim 1, wherein the housing includes a recessed portion configured to receive the syringe pump.

3. The system of claim 1, wherein the controller is configured to automatically control the syringe pump to change a volume of the expandable member based on a target value received from a user.

4. The system of claim 1, wherein the housing of the controller is configured to mechanically couple to a portion of the blood flow control device.

5. The system of claim 4, wherein the portion of the blood flow control device is a device controller housing electronics.

6. The system of claim 1, wherein the controller includes a lever configured to align the linear gear and the circular gear.

7. The system of claim 6, wherein the lever is configured to maintain a predetermined distance from a center of the linear gear to a center of the circular gear, and wherein the predetermined distance is between a range of 2 mm and 10 mm.

8. The system of claim 6, wherein in a closed configuration, the lever is configured to lock the syringe pump to the housing of the controller.

9. The system of claim 6, wherein the lever is biased toward an open configuration.

10. The system of claim 9, wherein a location of a center of mass of the lever biases the lever toward the open configuration.

11. The system of claim 6, wherein a first end of the lever includes a link and a joint configured to couple the lever to the housing of the controller, and wherein the lever is configured to pivot about the joint.

12. The system of claim 11, wherein a second end of the lever includes an indentation configured to mate the lever to a protrusion on the syringe pump.

13. The system of claim 6, wherein in a closed configuration, at least a portion of the lever and/or the cylindrical body pushes a switch on the controller.

14. The system of claim 13, wherein the controller is configured to determine whether the syringe pump is locked to the housing based on a position of the switch.

15. The system of claim 1, wherein the elongate body comprises of an inner layer, an outer layer, a metal alloy core, and a single lumen, wherein the single lumen is formed between the metal alloy core and the inner layer such that the inner layer surrounds the single lumen.

16. The system of claim 15, wherein the elongate body includes at least one sensor and wherein a sensor wire associated with the at least one sensor is routed between the inner layer and the outer layer.

17. The system of claim 1, further comprising a gearbox, wherein the gearbox couples to at least a portion of the circular gear, wherein a gear ratio of the gearbox is between 40:1 and 150:1.

18. The system of claim 17, wherein the gear ratio is 90:1.

19. A system configured for an endovascular procedure, the system comprising:

a blood flow control device comprising an elongate body and an expandable member positioned at a distal end of the elongate body;

a syringe pump in fluid communication with the expandable member, wherein the syringe pump comprises a linear gear and a mating feature; and a controller communicably coupled to the blood flow control device and releasably coupled to the syringe pump, wherein the controller comprises a controller housing, and the controller housing comprises:

a recessed portion configured to receive the syringe pump, and a lever, wherein the lever has an open configuration in which an end of the lever is positioned away from the controller housing and a closed configuration in which the end of the lever engages with the mating feature on the syringe pump, wherein the lever is biased toward the open configuration, and wherein in the closed configuration, the lever maintains an alignment between the linear gear on the syringe pump and a circular gear positioned at least partially within the controller housing and locks the syringe pump to the controller housing.

20. The system of claim 19, wherein the lever maintains alignment of the linear gear and the circular gear by maintaining a predetermined distance from a center of the linear gear to a center of the circular gear, and wherein the predetermined distance is between a range of 2 mm and 10 mm.

21. The system of claim 19, wherein a location of a center of mass of the lever biases the lever toward the open configuration.

22. The system of claim 19, wherein the end of the lever is a first end and wherein a second end of the lever includes a link and a joint configured to couple the lever to the controller housing, and wherein the lever is configured to pivot around the joint.

23. The system of claim 19, wherein in the closed configuration, at least a portion of the lever pushes a switch on the controller, and wherein the controller is configured to determine whether the syringe pump is locked to the controller housing based on a position of the switch.

* * * * *